(12) United States Patent
Zishaan

(10) Patent No.: US 8,674,842 B2
(45) Date of Patent: Mar. 18, 2014

(54) RESPONSIVE UNITS

(76) Inventor: Faiz Zishaan, Hatfield (GB)

( * ) Notice: Subject to any disclaimer, the term of this patent is extended or adjusted under 35 U.S.C. 154(b) by 633 days.

(21) Appl. No.: 12/670,797

(22) PCT Filed: Jul. 25, 2008

(86) PCT No.: PCT/GB2008/002547
§ 371 (c)(1),
(2), (4) Date: Jan. 26, 2010

(87) PCT Pub. No.: WO2009/013508
PCT Pub. Date: Jan. 29, 2009

(65) Prior Publication Data
US 2010/0225493 A1    Sep. 9, 2010

(30) Foreign Application Priority Data

| Jul. 26, 2007 | (GB) | 0714561.8 |
| Jul. 26, 2007 | (GB) | 0714562.6 |
| Apr. 18, 2008 | (GB) | 0807115.1 |

(51) Int. Cl.
G08B 21/00      (2006.01)

(52) U.S. Cl.
USPC ...... 340/627; 340/309.16; 340/628; 340/632; 702/24; 702/188; 431/18; 432/1; 432/37

(58) Field of Classification Search
USPC ........................................................ 340/627
See application file for complete search history.

(56) References Cited

U.S. PATENT DOCUMENTS

| 4,178,592 A | 12/1979 | McKee |
| 4,365,237 A | 12/1982 | Knight |
| 4,968,975 A | 11/1990 | Fritz |
| 5,159,315 A | 10/1992 | Schultz et al. |
| 5,594,422 A | 1/1997 | Huey, Jr. et al. |
| 5,726,634 A | 3/1998 | Hess et al. |
| 5,801,629 A | 9/1998 | Lehmann et al. |
| 5,894,275 A | 4/1999 | Swingle |
| 6,104,288 A | 8/2000 | Hopkins |
| 6,458,080 B1 * | 10/2002 | Brown et al. ............... 600/300 |
| 6,462,660 B1 | 10/2002 | Cannon et al. |
| 7,009,510 B1 * | 3/2006 | Douglass et al. ........... 340/531 |
| 2002/0126016 A1 | 9/2002 | Sipp |
| 2004/0119600 A1 | 6/2004 | Hampton |
| 2006/0217934 A1 * | 9/2006 | Armstrong ................. 702/188 |
| 2006/0258407 A1 * | 11/2006 | Chien ........................ 455/567 |

FOREIGN PATENT DOCUMENTS

| EP | 0995115 | 5/2004 |
| EP | 1441300 | 7/2004 |

(Continued)

*Primary Examiner* — George Bugg
*Assistant Examiner* — Anthony D Afrifa-Kyei
(74) *Attorney, Agent, or Firm* — Thorpe North & Western LLP

(57) ABSTRACT

An electronic communication unit such as a mobile phone comprises a processor for operating said unit; and an ambient air quality monitoring sensor; characterized in that said processor is configured to operate said unit in a first mode of operation during which a) monitoring of said air quality occurs and a level of air quality is assessed against pre-determined levels; and b) ordinary communication routines are activated provided an acceptable category of pre-determined levels is identified; and in a second mode of operation during which a) monitoring of said air quality occurs and a level of air quality is assessed against pre-determined levels; and b) an alarm routine is launched interrupting the ordinary communication routines once a level of ambient air quality is assessed to warrant the user's attention.

24 Claims, 32 Drawing Sheets

(56) References Cited

FOREIGN PATENT DOCUMENTS

| | | |
|---|---|---|
| EP | 1806543 | 7/2007 |
| GB | 2324398 | 10/1998 |
| GB | 2400959 | 10/2004 |
| GB | 2404459 | 2/2005 |
| WO | WO9322752 | 11/1993 |
| WO | WO9902987 | 1/1999 |
| WO | WO0241095 | 5/2002 |

* cited by examiner

RESPONSIVE UNITS

FIELD OF THE INVENTION

The invention relates to improvements to responsive units.

PRIOR ART KNOWN TO THE APPLICANT

The following prior art is acknowledged: U.S. Pat. No. 4,178,592; GB 2404459; U.S. Pat. No. 4,365,237; U.S. Pat. No. 5,594,422; U.S. Pat. No. 4,968,975; U.S. Pat. No. 5,726,634; US 2002/126016; WO 93/22752; GB 2324398; U.S. Pat. No. 5,159,315; U.S. Pat. No. 6,462,660; US 2004/119600; EP 1441300; US 2006/258407; U.S. Pat. No. 5,894,275; U.S. Pat. No. 5,801,629; U.S. Pat. No. 6,104,288; GB 2400959; WO 99/02987; and EP 0995115.

SUMMARY OF THE INVENTION

In a first broad independent aspect, the invention provides an electronic communication unit such as a mobile phone comprising a processor for operating said unit; and an ambient air quality monitoring sensor; characterised in that said processor is configured to operate said unit in a first mode of operation during which a) monitoring of said air quality occurs and a level of air quality is assessed against pre-determined levels; and b) ordinary communication routines are activated provided an acceptable category of pre-determined levels is identified; and in a second mode of operation during which a) monitoring of said air quality occurs and a level of air quality is assessed against pre-determined levels; and b) an alarm routine is launched interrupting the ordinary communication routines once a level of ambient air quality is assessed to warrant the user's attention.

The term "communication" is to be interpreted broadly and would include for example within its scope: communication in the form of a display of a clock face, communication offered through the display screen and audio system of a television, a PC, a laptop or any other similar device, and communication achieved by a GPS unit, a baby monitor, or a home security system.

In a subsidiary aspect, an alarm routine is launched interrupting the ordinary communication routines provided a harmful category of pre-determined levels is identified.

In a further subsidiary aspect, the unit further comprises a communication interface for inputting signals representative of characteristics such as sex, weight, age, physical activity levels and health of an individual; and a plurality of predetermined operational modes corresponding to such characteristics.

In a further subsidiary aspect, the unit further comprises a display for indicating a) a level of sensed air quality and b) a time estimate before a harmful level is reached; whereby a countdown to a harmful level is displayed.

In a further subsidiary aspect, said unit further comprises means for causing said processor to obtain signals representative of said sensed air quality at a plurality of points in time; means for storing a plurality of alarm signals; and means for selecting an indication of level of air quality dependent upon the evolution through time of said signals representative of said sensed air quality.

In a further subsidiary aspect, said unit comprises means for recording a signal representative of an air quality level and a signal representative of the time of monitoring of said air quality level.

In a further subsidiary aspect, said unit further comprises a communication interface for inputting signals for triggering a future mode of operation; and a trigger for triggering a mode of operation dependent upon the reaching of a predetermined time.

In a further subsidiary aspect, said unit further comprises a recorder for recording a period during which exposure to a harmful category of air was sensed and a communication interface for communicating said period to an operator of the unit.

In a further subsidiary aspect, said unit further comprises a recorder for recording signals representative of a change in operational mode during a period of time.

In a further subsidiary aspect, said unit further comprises an indicator for indicating an air quality level, means for causing said processor to obtain signals representative of said sensed air quality at a plurality of points in time, and means for displaying fluctuations in determined air quality levels.

In a further subsidiary aspect, said unit further comprises a vibrator alarm for causing the unit to vibrate provided a harmful category of pre-determined levels is identified.

In a further subsidiary aspect, said unit further incorporates lighting means acting as a visual alarm provided a harmful category of pre-determined levels is identified.

In a further subsidiary aspect, said unit incorporates a wireless transmitter for sending a signal representative of the unit's status to a wireless receiver.

In a further subsidiary aspect, said processor is adapted to trigger a reminder alarm dependent upon the reaching of a predetermined time.

In a further subsidiary aspect, said processor is configured to trigger a reminder alarm for testing and/or calibrating the sensor.

In a further subsidiary aspect, said processor is configured to trigger a reminder alarm for having a proximate/corresponding/relevant fuel burning appliance serviced and/or checked.

In a further subsidiary aspect, said processor is adapted to trigger a vocal alarm.

In a further subsidiary aspect, said unit further comprises a housing incorporating said processor and a sensor holder which allows the sensor to be held at a variable spaced apart distance from said housing.

In a further subsidiary aspect, said unit further comprising a wireless communication interface in communication with one or more remotely located sensors.

In a further subsidiary aspect, said unit incorporates one or more of the following further sensors: altitude, atmospheric, pressure, humidity, and/or temperature sensor; and means for adjusting the assessment of level of air quality in accordance with values derived from said sensor in addition to values derived from said air quality sensor.

In a further subsidiary aspect, said unit incorporates a single microprocessor which incorporates said sensor.

In a further subsidiary aspect, said unit incorporates a calendar function block which stores a date and air quality levels for subsequent retrieval and processing.

In a further subsidiary aspect, said unit incorporates a first alarm routine suitable for triggering an alarm which is perceptible during an operator's sleep when in the vicinity of said unit and a second alarm routine suitable for triggering an alarm which is perceptible whilst the operator is active when in the vicinity of said unit.

In a further subsidiary aspect, said unit incorporates means for transmitting a signal representative of a level of ambient air quality assessed to warrant the user's attention to a remote signal receiver.

In a further subsidiary aspect, said unit further comprises means for communicating a warning signal to a user which is specific to one or more articles to be packed; and a processor which during a period preceding a user's change of location triggers the communication of said signal to a user of said system in order to remind a user to pack an article.

In a further subsidiary aspect, said unit further comprises a detector for detecting that said unit is in a travelling mode of use.

In a further subsidiary aspect, said detector operates in conjunction with means for detecting changes in time zone settings.

In a further subsidiary aspect, said unit incorporates a portable article with means for roaming in wireless networks; and said detector operates in conjunction with means for detecting changes in roaming status.

In a further subsidiary aspect, said unit is suitable for operating with a charger and said unit further incorporates a detector which is configured to detect when a charger is separated from said unit.

In a further subsidiary aspect, said unit incorporates a detector which is configured to detect changes in electrical supply.

In a further subsidiary aspect, said detector is configured to detect changes in information formats.

In a further subsidiary aspect, said detector is configured to detect audible signals such as words and compare said signals against predetermined signals which are stored on a recording medium.

In a further subsidiary aspect, said unit incorporates a light detector.

In a further subsidiary aspect, said unit incorporates a pressure detector.

In a further subsidiary aspect, said system incorporates a button which upon actuation causes or allows the user to set the requirements for a warning signal to be repeated after a predetermined period of time.

In a further subsidiary aspect, said unit incorporates a switch for switching the article ON and/or OFF with powering means for generating a warning signal which operates whilst said unit is not switched on.

In a further subsidiary aspect, said unit incorporates means for detecting the location of the unit and means for controlling the timing of a warning signal generation dependent upon a location.

In a further subsidiary aspect, said unit incorporates means for sending a signal to associated peripheral devices which incorporate a receiver and an alarm for responding to said received signal.

In a further subsidiary aspect, said receiver is configured to instantly respond to said received signal. Optionally, said response is at least one of audible, visual and/or perceptible.

In a further broad aspect, the invention provides an air quality monitoring unit comprising a sensor exposed to air; a processor; a communication channel for communicating signals representative of said sensed air quality from said sensor to said processor; and an alarm which is triggered by said processor dependent upon the signals received from said sensor; wherein the unit further comprises a communication interface for inputting signals representative of characteristics such as sex, weight, age, physical activity levels and health of an individual which would inhabit a monitored space; and a plurality of predetermined operational modes corresponding to such characteristics.

In a further broad aspect, the invention provides an air quality monitoring unit comprising a sensor exposed to air; a processor; a communication channel for communicating signals representative of said sensed air quality from said sensor to said processor; and an alarm which is triggered by said processor dependent upon the signals received from said sensor; wherein the unit comprises a display for indicating a) a level of sensed air quality and b) a time estimate before a harmful level is reached; whereby a countdown to a harmful level is displayed.

In a further broad aspect, the invention provides an air quality monitoring unit comprising a sensor exposed to air; a processor; a communication channel for communicating signals representative of said sensed air quality from said sensor to said processor; and an alarm which is triggered by said processor dependent upon the signals received from said sensor; wherein said unit further comprises a communication interface for inputting signals for triggering a future mode of operation; and a trigger for triggering a mode of operation dependent upon the reaching of a predetermined time.

In a further broad aspect, the invention provides an air quality monitoring unit comprising a sensor exposed to air; a processor; a communication channel for communicating signals representative of said sensed air quality from said sensor to said processor; and an alarm which is triggered by said processor dependent upon the signals received from said sensor; wherein said processor is adapted to trigger a reminder alarm dependent upon the reaching of a predetermined time.

In a further broad aspect, the invention provides an air quality monitoring unit comprising a sensor exposed to air; a processor; a communication channel for communicating signals representative of said sensed air quality from said sensor to said processor; and an alarm which is triggered by said processor dependent upon the signals received from said sensor; wherein said unit incorporates a first alarm routine suitable for triggering an alarm which is perceptible during an operator's sleep when in the vicinity of said unit and a second alarm routine suitable for triggering an alarm which is perceptible whilst the operator is active when in the vicinity of said unit.

In a further broad aspect, the invention provides a mobile phone incorporating an air quality monitoring sensor configured to monitor ambient air.

In a further broad aspect, the invention provides a global positioning unit incorporating an air quality monitoring sensor configured to monitor ambient air.

In a further broad aspect, the invention provides a television incorporating an air quality monitoring sensor configured to monitor ambient air.

In a further broad aspect, the invention provides a portable computer incorporating an air quality monitoring sensor configured to monitor ambient air.

In a further broad aspect, the invention provides a desk top computer incorporating an air quality monitoring sensor configured to monitor ambient air.

In a further broad aspect, the invention provides a baby monitor incorporating an air quality monitoring sensor configured to monitor ambient air.

In a further broad aspect, the invention provides a home security system incorporating an air quality monitoring sensor configured to monitor ambient air.

In a further broad aspect, the invention provides a travel packing assisting system comprising means for communicating a warning signal to a user which is specific to one or more articles to be packed; and a processor which during a period preceding a user's change of location triggers the communication of said signal to a user of said system in order to remind a user to pack said article; wherein said system further comprises a detector for detecting that an article is in a travelling mode of use and said detector operates in conjunction with means for detecting changes in time zone settings.

In a further broad aspect, the invention provides a travel packing assisting system comprising means for communicating a warning signal to a user which is specific to one or more articles to be packed; and a processor which during a period preceding a user's change of location triggers the communication of said signal to a user of said system in order to remind a user to pack said article; wherein said system further comprises a detector for detecting that an article is in a travelling mode of use and said system incorporates a portable article with means for roaming in wireless networks; said detector operating in conjunction with means for detecting changes in roaming status.

In a further broad aspect, the invention provides a travel packing assisting system comprising means for communicating a warning signal to a user which is specific to one or more articles to be packed; and a processor which during a period preceding a user's change of location triggers the communication of said signal to a user of said system in order to remind a user to pack said article; wherein said system further comprises a detector for detecting that an article is in a travelling mode of use; said detector being configured to detect when a charger is separated from a mobile battery powered article.

In a further broad aspect, the invention provides a travel packing assisting system comprising means for communicating a warning signal to a user which is specific to one or more articles to be packed; and a processor which during a period preceding a user's change of location triggers the communication of said signal to a user of said system in order to remind a user to pack said article; wherein said system further comprises a detector for detecting that an article is in a travelling mode of use which incorporates means for activating said system by unplugging said charger.

In a further broad aspect, the invention provides a travel packing assisting system comprising means for communicating a warning signal to a user which is specific to one or more articles to be packed; and a processor which during a period preceding a user's change of location triggers the communication of said signal to a user of said system in order to remind a user to pack said article; wherein said system further comprises a detector for detecting that an article is in a travelling mode of use; said detector being configured to detect changes in electrical supply.

In a further broad aspect, the invention provides a travel packing assisting system comprising means for communicating a warning signal to a user which is specific to one or more articles to be packed; and a processor which during a period preceding a user's change of location triggers the communication of said signal to a user of said system in order to remind a user to pack said article; wherein said system further comprises a detector for detecting that an article is in a travelling mode of use; said detector being configured to detect changes in information formats.

In a further broad aspect, the invention provides a travel packing assisting system comprising means for communicating a warning signal to a user which is specific to one or more articles to be packed; and a processor which during a period preceding a user's change of location triggers the communication of said signal to a user of said system in order to remind a user to pack said article; wherein said system further comprises a detector for detecting that an article is in a travelling mode of use; said detector being configured to detect audible signals such as words and to compare said signals against predetermined signals which are stored on a recording medium.

In a further broad aspect, the invention provides a travel packing assisting system comprising means for communicating a warning signal to a user which is specific to one or more articles to be packed; and a processor which during a period preceding a user's change of location triggers the communication of said signal to a user of said system in order to remind a user to pack said article; wherein said system further comprises a detector for detecting that an article is in a travelling mode of use; said detector being a light detector.

In a further broad aspect, the invention provides a travel packing assisting system comprising means for communicating a warning signal to a user which is specific to one or more articles to be packed; and a processor which during a period preceding a user's change of location triggers the communication of said signal to a user of said system in order to remind a user to pack said article; wherein said system further comprises a detector for detecting that an article is in a travelling mode of use; said detector being a pressure detector.

In a further broad aspect, the invention provides a travel packing assisting system comprising means for communicating a warning signal to a user which is specific to one or more articles to be packed; and a processor which during a period preceding a user's change of location triggers the communication of said signal to a user of said system in order to remind a user to pack said article; wherein said system further comprises a portable article with a button which upon actuation causes a warning signal to be repeated after a predetermined period of time. The warning signal may optionally be at least one of audible, visual and/or perceptible.

In a further broad aspect, the invention provides a travel packing assisting system comprising means for communicating a warning signal to a user which is specific to one or more articles to be packed; and a processor which during a period preceding a user's change of location triggers the communication of said signal to a user of said system in order to remind a user to pack said article; wherein said system further incorporates a powered portable article with a switch for switching the article ON and/or OFF with powering means for generating a warning signal which operates whilst said article is not switched on.

In a further broad aspect, the invention provides a travel packing assisting system comprising means for communicating a warning signal to a user which is specific to one or more articles to be packed; and a processor which during a period preceding a user's change of location triggers the communication of said signal to a user of said system in order to remind a user to pack said article; wherein said system further incorporates a portable article and means for receiving instructions for controlling the timing of the warning signal generation dependent upon a location.

In a further broad aspect, the invention provides a travel packing assisting system substantially as hereinbefore described with reference to any appropriate combination of the accompanying text.

In a further broad aspect, the invention provides a unit substantially as hereinbefore described with reference to any appropriate combination of the accompanying text.

In a further broad independent aspect, the invention provides an air quality monitoring unit comprising a sensor exposed to air; an activator for activating the unit; a controller; a communication channel for communicating signals representative of said sensed air quality from said sensor to said controller; and an alarm which is triggered by said controller dependent upon the signals received from said sensor; wherein the unit further comprises a housing incorporating said alarm, and a sensor holder which allows the sensor to be held at a variable spaced apart distance from said housing.

This feature is particularly advantageous as it allows the unit housing to be placed in a location which may not be exposed to the optimum air flow for detection whilst the sensor may be placed in a location where advantageous sensing may take place. In a subsidiary aspect in accordance with the invention's first broad independent aspect the unit incorporates a holder in the form of a telescopic member. In a further subsidiary aspect, the sensor holder may be provided with a portion which may extend, spring, open, fold or swivel out in order to extend the distance between the housing and the sensor.

This may take the form of foldout/swivel arrangements of the kind employed by some mobile phone providers.

In a further broad independent aspect, the invention provides an air quality monitoring unit comprising a sensor exposed to air; an activator for activating the unit; a controller; a communication channel for communicating signals representative of said sensed air quality from said sensor to said controller; and an alarm which is triggered by said controller dependent upon the signals received from said sensor; wherein the unit further comprises one or more indicators for indicating time and an air quality level.

This feature is particularly advantageous because it increases user interaction and familiarity with units. If the time indicator takes the form of a clock, it will for example be constantly referred to throughout the day by an observer who would therefore detect a potential hazard before any audible alarm would be triggered.

In a further broad independent aspect, the invention provides an air quality monitoring unit comprising a sensor exposed to air; an activator for activating the unit; a controller; a communication channel for communicating signals representative of said sensed air quality from said sensor to said controller; and an alarm which is triggered by said controller dependent upon the signals received from said sensor; wherein said controller incorporates a time keeping device; a communication interface for inputting signals for triggering a future mode of operation; and a trigger for triggering a mode of operation dependent upon the reaching of a predetermined time.

This configuration is particularly advantageous because it allows the unit to potentially function as a calendar, an organiser and a reminder. In this subsidiary aspect, it will allow the unit to inform an observer of the need for an annual appliance (for example a boiler) service. It would also allow the operational mode to be controlled in order to be active during operator selected periods such as during the night. This would be particularly beneficial if the device is used as a travel air quality monitoring unit since it would avoid the batteries being used during transportation.

This configuration is particularly advantageous because it also allows the recording of the date and time of the last time the unit itself was tested whilst allowing a reminder for the next test to be entered.

In a further broad independent aspect, the invention provides an air quality monitoring unit comprising a sensor exposed to air; an activator for activating the unit; a controller; a communication channel for communicating signals representative of said sensed air quality from said sensor to said controller; and an alarm which is triggered by said controller dependent upon the signals received from said sensor; wherein said unit further comprises means for causing said controller to obtain signals representative of said sensed air quality at a plurality of points in time; means for storing a plurality of alarm signals; and means for selecting said alarm signals dependent upon the evolution through time of said signals representative of said sensed air quality.

This configuration is particularly advantageous because it allows intelligent and measured responses. For example, when the sensor is a carbon monoxide sensor, the unit of this configuration can assess whether the exposure to carbon monoxide is severe or moderate. It allows the response of the unit to be tailored to various pre-determined conditions. It also allows the alarm to be selected by the operator for the kind of individual which the air quality monitoring unit is destined to protect. This configuration would for example allow an alarm to be raised inside or outside the room and to be intelligible to children as young as 2 to 3 years with only minimal training. It also allows the operator to select an ascending alarm or a full alarm by pressing an appropriate switch on the unit. In the embodiment where a clock and a monitoring unit are combined, it is likely that the alarm would be sounded in close proximity to a user of the monitoring unit. Therefore, an ascending alarm would be preferred since an immediate alarm blast of a relatively high decibel level would not be sensible or desired. This configuration may be adapted to sound an alarm or a full alarm following a period of critical exposure countdown or during periods where the user was particularly vulnerable or likely to be less alert, such as during sleep.

In a further broad independent aspect, the invention provides an air quality monitoring unit comprising a sensor exposed to air; an activator for activating the unit; a controller; a communication channel for communicating signals representative of said sensed air quality from said sensor to said controller; and an alarm which is triggered by said controller dependent upon the signals received from said sensor; wherein said unit further comprises a recorder for recording signals representative of the time during which a hazard occurred.

This configuration is particularly advantageous because it allows an intermittent fault in a boiler for example to be identified. For example, a boiler may be used for a period of 30 minutes only for the heating of hot water which would not necessarily cause a threshold level of carbon monoxide in a given room which is being monitored to be reached.

In a subsidiary aspect, the unit may also include a means for postponing the triggering of an alarm. This might enable the operator to enter an acceptable exposure time. It would also optionally be able to indicate a recommended evacuation time due to a particular level of detected air quality. This would allow the co-ordination of rescue efforts for workers and military personnel working in known hazardous areas where potentially not being able to operate is not viable, but at the same time, knowledge of the critical exposure levels would facilitate optimal management of the situation.

In a further broad independent aspect, the invention provides an air quality monitoring unit comprising a sensor exposed to air; an activator for activating the unit; a controller; a communication channel for communicating signals representative of said sensed air quality from said sensor to said controller; and an alarm which is triggered by said controller dependent upon the signals received from said sensor; wherein said unit further comprises a recorder for recording signals representative of a change in operational mode during a period of time.

In a further broad independent aspect, the invention provides an air quality monitoring unit comprising a sensor exposed to air; an activator for activating the unit; a controller; a communication channel for communicating signals representative of said sensed air quality from said sensor to said controller; and an alarm which is triggered by said controller dependent upon the signals received from said sensor; wherein said unit further comprises a recorder for recording a period during which exposure to hazardous air was sensed and a communication interface for communicating said period to an operator of the unit.

This configuration is particularly advantageous because it allows the operator to precisely determine the level of exposure. This may for example assist medical staff to determine the best course of treatment to be employed in a given situation.

In a further broad independent aspect, the invention provides an air quality monitoring unit comprising a sensor exposed to air; an activator for activating the unit; a controller; a communication channel for communicating signals representative of said sensed air quality from said sensor to said controller; and an alarm which is triggered by said controller dependent upon the signals received from said sensor; wherein said unit further comprises an indicator for indicating an air quality level, means for causing said controller to obtain signals representative of said sensed air quality at a plurality of points in time, and means for displaying fluctuations in determined air quality levels.

This would allow the user of the unit to immediately identify critical conditions. In a subsidiary aspect in accordance with the eighth broad independent aspect, the means for displaying fluctuations may take the form of an intelligent and constantly changing read out which would provide visual confirmation that the unit is functioning properly.

In a further broad independent aspect, the invention provides an air quality monitoring unit comprising a sensor exposed to air; an activator for activating the unit; a controller; a communication channel for communicating signals representative of said sensed air quality from said sensor to said controller; and an alarm which is triggered by said controller dependent upon the signals received from said sensor; wherein the unit further comprises a communication interface for inputting signals representative of characteristics such as sex, weight, age, and health of an individual which would inhabit a monitored space; and a plurality of predetermined operational modes corresponding to such characteristics. This would allow the alarm to be tailored to the particular needs of an individual in order to improve the efficacy of the unit.

In a further broad independent aspect, the invention provides an air quality monitoring unit comprising a sensor exposed to air; an activator for activating the unit; a controller; a communication channel for communicating signals representative of said sensed air quality from said sensor to said controller; and an alarm which is triggered by said controller dependent upon the signals received from said sensor; wherein said unit further comprises a vibrator alarm for causing the unit to vibrate.

This configuration is particularly advantageous because it would allow the detection of a hazard to be felt; it would be particularly advantageous for the hearing impaired or the partially sighted.

In a further broad independent aspect, the invention provides an air quality monitoring unit comprising a sensor exposed to air; an activator for activating the unit; a controller; a communication channel for communicating signals representative of said sensed air quality from said sensor to said controller; and an alarm which is triggered by said controller dependent upon the signals received from said sensor; wherein said unit incorporates lighting means acting as a visual alarm. This configuration is particularly advantageous because it allows the unit to be effective in communicating the presence of a hazard for the hearing impaired.

In a further broad independent aspect, the invention provides an air quality monitoring unit comprising a sensor exposed to air; an activator for activating the unit; a controller; a communication channel for communicating signals representative of said sensed air quality from said sensor to said controller; and an alarm which is triggered by said controller dependent upon the signals received from said sensor; wherein said unit incorporates a wireless transmitter for sending a signal representative of the unit's status to a wireless receiver.

This configuration is particularly advantageous because it allows remote monitoring to occur. This would particularly be beneficial if the wireless link is to a mobile phone through a mobile network so that for example parents can monitor a room where a child is sleeping without necessarily having to see the monitor or even being in the audible range for the alarm.

The invention also provides a dictation machine incorporating an air quality monitoring unit according to any of the preceding aspects. This combination of features is particularly advantageous because during operation of the dictation machine a user is required to pay particular attention to its display. It also may be configured with only minimal components added to the basic dictation machine structure. For example, the loud speaker of the dictation machine may be used both to listen to the play-back of recordings and for sounding the alarm. In addition, if the dictation machine is configured optionally with a vibrator, it would allow the operator to immediately sense through his/her hand whilst holding the machine that a hazard is present.

The invention also provides a travel alarm incorporating an air quality monitoring unit according to any of the preceding aspects. A number of special advantages arise when incorporating an air quality monitoring unit into a travel alarm. When for example the travel alarm incorporates a loud speaker, the loud speaker may be configured to sound an alarm relating to a hazardous air quality and alternatively sound an alarm for waking the user in conventional fashion. It also allows the air quality monitoring alarm to be naturally positioned in close proximately to a user for example on the top of a bedside cabinet in order to achieve a more efficient form of communication between the unit and its user. In one embodiment, it also allows a user to assess time and the current air quality in a single glance thus improving user awareness and likely response time to any impending hazard.

In a further broad independent aspect, the invention provides a travel packing assisting system comprising means for communicating a warning signal to a user which is specific to one or more articles to be packed; and a controller which during a period preceding a user's change of location triggers the communication of said signal to a user of said system in order to remind a user to pack said article.

In a subsidiary aspect in accordance with the invention's broadest independent aspect, said means for communicating is integrated in a portable article. It allows the article itself to be heard and located prior to for example leaving a hotel room. It also allows the system to operate without any fixed and/or wall mounted components.

In a further subsidiary aspect, the system further comprises a detector for detecting that an article is in a travelling mode of use. This allows the system to be configured or at least partly configured automatically without requiring the user and/or traveler to necessarily initiate the operation of the travel packing assisting system.

In a further subsidiary aspect, said detector operates in conjunction with means for detecting changes in time zone settings. This configuration allows the system to detect a travelling mode when for example a user enters a new time into his or her mobile device such as a mobile phone. This system would also for example notice an automatic clock change which may be facilitated by a wireless network through a control communication channel with a portable article.

The system may for example cause a user interface to be opened up on the screen of a user for a user to confirm whether or not he/she is in a travelling mode. If he/she inputs a signal representative of a travelling mode, the system then asks for inputting hotel room departure dates and times for the alarm signal to be triggered. If the user inputs a signal representative of the user not being in a travelling mode, then the system shuts down until the next change of travelling mode is detected.

In a further subsidiary aspect, said system incorporates a portable article with means for roaming in wireless networks; and said detector operates in conjunction with said means for detecting changes in roaming status. This configuration is particularly advantageous because it allows the system to be readily integrated into existing wireless portable articles such as a mobile phone which already responds to changes in roaming conditions. Once again in this configuration, the system may optionally open up a user interface to allow a user to select the level and times of assistance required.

In a further subsidiary aspect, the invention provides a system which incorporates two portable articles; one of said articles being a mobile battery powered article and the second being a charger for said mobile battery powered article; wherein said detector is configured to detect when said charger is separated from said mobile battery powered article. This form of detection will also allow the system to be configured. It is particularly advantageous because it may operate automatically without requiring the user to drive the system.

In a further subsidiary aspect, said system incorporates a portable article in the form of a charger; and means for activating said system by unplugging said charger. This configuration is particularly advantageous because it allows the initiation of the system to be triggered automatically or at least in part automatically by detecting an action which is typical of the packing process.

In a further subsidiary aspect, said system incorporates a powered article and said detector is configured to detect changes in electrical supply. This configuration is particularly advantageous because it would allow the detection of a change in voltage for example which occurs when a portable article is plugged in during travelling to a destination with a different level of voltage. The system is particularly advantageous because it may be readily incorporated into a mobile device since many already incorporate means for automatically changing between voltages. By monitoring the change in voltage, the system may readily be initiated or may be automatically configured.

In a further subsidiary aspect, such system incorporates a portable article and said detector is configured to detect changes in information formats. The term "information format" is to be interpreted broadly and may for example include changes in formats which have national characteristics such as PAL and/or NTSC.

In a further subsidiary aspect, said system incorporates a portable article and said detector is configured to detect audible signals such as words and compares said signals against pre-determined signals which are stored on a recording medium. This feature is particularly advantageous because it would allow the system to be potentially initiated automatically by detecting key words which are associated with the departure from a particular location. Key words may be for example: translations, depart, arrive, flight, train, taxi etc.

In a further subsidiary aspect, said system incorporates a portable article and said detector is a light detector. This configuration is particularly advantageous because it would allow an article to sense when it is packed. In a subsidiary aspect, the detector may be configured to detect complete darkness or a level of darkness associated with the inside of a packed closed suitcase which would indicate that the article is packed. If a form of light is detected, the system may still trigger the warning signal so that a user remembers to pack the article.

In a further subsidiary aspect, said system incorporates a portable article and said detector is a pressure detector. This may take the form of a compression detector in order to allow the article to sense that it must have been packed. This would therefore allow the automatic warning signal to be switched off in such conditions. Alternatively, if no pressure threshold is reached, the article will assume that it has not been packed and will therefore cause through its controller a warning signal to be sounded.

In a further subsidiary aspect, the invention provides a system which incorporates a portable article with a button which upon actuation causes a warning signal to be repeated after a pre-determined period of time. This would allow the user to select the option of requesting the system to remind him/her again at a later time.

In a further subsidiary aspect, said system incorporates a powered portable article with a switch for switching the article ON and/or OFF with powering means for generating a warning signal which operates when said article is not switched on. This configuration may take the form of an energy backup so that the warning signal may be sounded even if the unit is switched off.

In a further subsidiary aspect, said system incorporates a portable article and means for receiving instructions for controlling the timing of the warning signal generation dependent upon a location. This would allow the system to determine that a user is in a particular hotel which would have a particular check-out time in order to remind the user at the most appropriate moment in order to meet the check-out time having packed the article.

In a further subsidiary aspect the invention provides a database of travel specific information and means to hold the access of check-in/out times, contact numbers, airline confirmation numbers, and/or any other appropriate tourist information.

In a further subsidiary aspect, the system operates at network or satellite level once roaming of a user is detected in which case the network could then send out a signal for example: a text, voice or multimedia message with the appropriate reminder instead of it being generated in the unit itself.

In a further subsidiary aspect, the system operates through networking so that a laptop, for example, can automatically set an alarm on a mobile or watch.

In a further subsidiary aspect, any portable article operating in conjunction with the system incorporates means for receiving alarm instructions from another device such as a PC.

In a further subsidiary aspect, the system operates automatically once a portable article has been switched on.

DETAILED DESCRIPTION OF THE FIGURES

Figure 1:
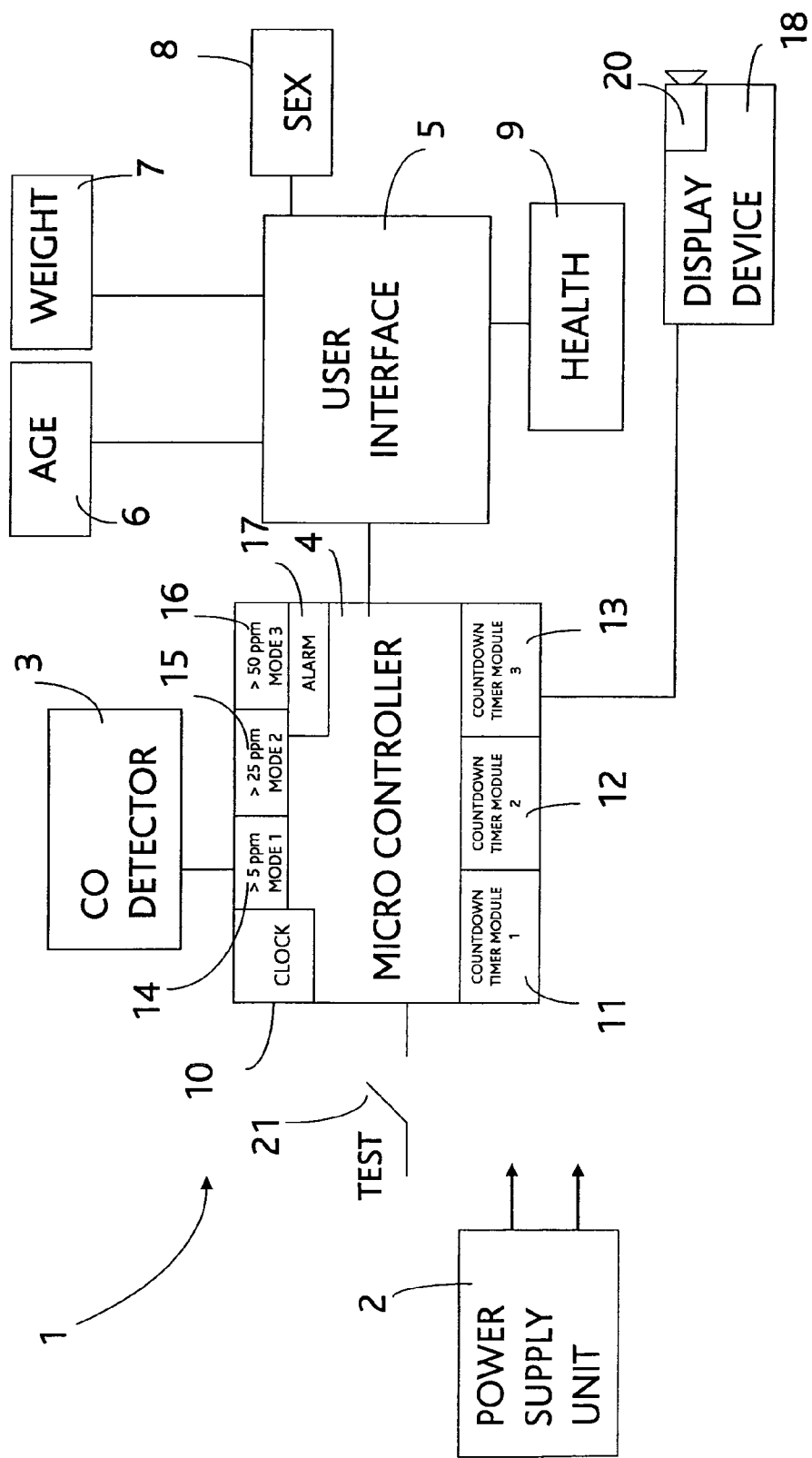
FIG. 1 shows a system block diagram representing the components of an air quality monitoring unit.

FIG. 1 shows a system block diagram of an air quality monitoring unit 1. The air quality monitoring unit 1 incorporates a power supply unit 2, a CO (carbon monoxide) detector 3 and a micro-controller 4.

The power supply unit 2 is powered by a mains voltage source (typical value in the UK is 230 volts AC @ 50 hertz), which produces a stable DC output voltage, that is required for powering all the components within the monitoring unit 1. In a further embodiment, the power supply is a battery or battery bank.

The CO detector 3 would typically be a metal oxide semi-conductor sensor. Metal oxide semi-conductor sensors incorporate thin wires of the semi-conductor of tin dioxide, on an insulating ceramic base, resulting in a sensor which is capable of being monitored by an integrated circuit. CO exposure reduces resistance and so allows a greater current, which if high enough will lead to the monitoring circuit triggering an alarm. In a preferred embodiment, the sensor is adapted to monitor the presence of CO continuously and/or at regular closely spaced intervals. Furthermore, in a further preferred embodiment the sensor is adapted to monitor both the presence and its amount. Furthermore, in a further preferred embodiment the sensor is adapted to monitor both the presence and its amount in a highly linear way. It also evaluates the level of harm of a given exposure and assesses the length of time required to arrive at a critical harm level at said given exposure. An alarm level is therefore potentially never reached if the user changes his/her environment as a reaction to a given exposure level or harm level indication. An alarm mechanism would nevertheless be triggered should the critical exposure level be breached.

In a preferred embodiment, the detector is a sensor array.

In a further preferred embodiment, the system is a single sensor.

An example of a metal oxide semi-conductor sensor which may be adapted to the functionality outlined in this description would be a gated metal oxide sensor, which does not require heating and has a high selectivity and sensitivity to CO. It also has a reliable CO lower detection limit of 2 PPM and operates down to −60° C. No warm up time is required and the sensor is miniaturised and consumes very low power. This type of sensor has an operating temperature range of −60° C. to 180° C., a sensing range of 0 to 1000 PPM, a response time of less than 5 seconds and an accuracy of plus or minus 2 PPM. The response may be adapted to be the display of the CO measurement, the harm level and/or the length of time which this exposure may be tolerated for a given individual prior to reaching a level at which the user may suffer an impairment to physical or cardiovascular performance, symptoms, physical harm, or even death as a result ("Calculated Harm Threshold").

The calculation of Calculated Harm Threshold can be adapted and presented in a similar way for any of the gasses and/or pollutants listed in the detailed description section, along with any number of single or multiple gas/pollutant threats so the Calculated Harm Threshold may relate to either impact on the user's health or that of the ecological environment. For example, a carbon dioxide (CO2) sensor embedded within a device may allow additional inputs relevant to the user's actual, averaged or estimated emissions of CO2 through their various activities (e.g. estimated Carbon Footprint, vehicle details, driving conditions and duration of average commute) their recommended CO2 allowances (or Target Carbon Footprints) local or national environmental conditions, in order to calculate and display the corresponding impact upon the environment of any sensed CO2 in addition to any health related impact such emissions may present. In this instance the countdowns and alarms would relate to reaching the user's quotas of carbon emissions, and the information presented could consist of information and recommendations for offsetting the environmental impact of their activities.

Due to its miniaturisation, the sensor is advantageously suited for integration into many applications, such as household gas alarms, indoor quality monitors, occupational dosimeters, portable gas detectors and monitors, transformer fault detection, aircrafts and automobiles. However, alternative types of CO detector are considered, such as biomimetic and electrochemical. Biomimetic sensors, also known as chem-optical or gel cell, work with a form of synthetic haemoglobin which darkens in the presence of CO, and which lightens with decrease amounts of CO and/or in its absence. This type of sensor can be seen directly or connected to a light sensor or alarm. Electro chemical sensors are a type of fuel cell that instead of being designed to produce power, are designed to produce a current which is precisely related to the amount of the CO in the atmosphere. Essentially the electrochemical sensor may take the form of a cell which consists of a container, two electrodes, connection wires and an electrolyte—typically sulphuric acid. CO is oxidised at one electrode to carbon dioxide whilst oxygen is consumed at the other electrode. For CO detection, the electrochemical cell has advantages in that it has a highly accurate and linear output to CO concentration, it requires minimal power as it functions at room temperature and has an increased longevity of approximately five years or more. Most electrochemical sensors have a limited temperature range and do not show a reliable response below 30 parts per million (PPM). Furthermore, in a further preferred embodiment the electrochemical sensor may be adapted to monitor both the presence of CO and its amount, rather than simply sounding an alarm. Furthermore, in a further preferred embodiment the sensor is adapted to monitor both the presence and its amount in a highly linear way. It also evaluates the level of harm of a given exposure and assesses the length of time required to arrive at a critical harm level at said given exposure. An alarm level is therefore potentially never reached if the user changes his/her environment as a reaction to a given exposure level or harm level indication. An alarm mechanism would nevertheless be triggered should the critical exposure level be breached.

In a preferred embodiment, the detector is a sensor array.

In a further preferred embodiment, the system is a single sensor.

At the heart of the monitoring unit 1 is a microcontroller which may be of a known kind and adapted for the functionality as outlined in this description. It is a derivative of a microprocessor with incorporated high integration, low power consumption, self sufficiency and cost effectiveness, by contrast to a general purpose microprocessor (of the kind used in a PC). In addition to arithmetic and logic elements of a general purpose microprocessor, the microcontroller integrates, in an exemplary embodiment, at least one of the following elements or every single one of the following elements: a read/write memory for data storage, read only memory, such as flash for code storage, EEPROM for permanent data storage, peripheral devices and input/output interfaces. At clock speeds of as little as a few Megahertz (MHz) or even lower, microcontrollers often operate at very low speed compared to modern day microprocessors, but this is adequate for CO detection applications. They consume relatively little power (milliwatts), and have the ability to sleep while waiting for an interesting peripheral event, such as a button press to wake it up again to do something. The microcontroller's power consumption while sleeping may be just nanowatts, making them ideal for low power and long lasting battery applications.

A button may in an optionally advantageous form be a so called soft button or soft switch which could be incorporated to for example a mobile phone screen or tap zones on touch sensitive screens or selection wheels.

Other features integrated within a microcontroller are envisaged:
- Central processing unit—ranging from a small and simple 4-bit processor to complex 32- or 64- or higher bit processors.
- Discrete input and output bits, allowing control or detection of the logic state of an individual package pin.
- Serial input/output such as serial ports (UARTS).
- Other serial communications interfaces like $I^2C$, Serial Peripheral Interface and Controller Area Network for system interconnects of the units components.
- Peripherals such as timers, event counters, Pulse Width Modulators (PWM) and watchdog.
- Volatile memory (RAM) for data storage.
- ROM, EPROM, EEPROM or Flash memory for program and operating parameter storage.
- Clock generator—often an oscillator for a quartz timing crystal, resonator or RC circuit.
- Analogue to digital converters.
- Digital to analogue converters.
- In-circuit programming and debugging support.

A microcontroller facilitates the reduction of size, cost, and power consumption compared to a design using a separate microprocessor, memory, and input/output devices. A microcontroller as envisaged in the invention can make it economical to electronically control many more processes. An embodiment of the invention envisages selecting an existing microprocessor of an electrical device such as a TV, mobile, GPS unit, or a clock and adapting and/or enhancing its capacities in order to achieve the operative control of a CO detector with the functionality of the kind envisaged in this description.

The microcontroller 4 is powered by the power supply unit 2. The power supply may be the power supply of the device in which the monitoring system is incorporated. It may be battery and/or solar powered for example, although any other form of powering is envisaged. The microcontroller is also coupled to the CO detector 3 and user interface 5. The user interface 5 may typically be a keypad on the monitoring unit 1, a menu driven display which incorporates drop down menus for selecting data or a remote device that is remotely connected to the monitoring unit 1. The user interface 5 allows the user to enter personal attributes such as age 6, weight 7, sex 8 and health 9 into the monitoring unit 1. These personal attributes and/or medical conditions are then processed by the microcontroller's application code, which incorporates a functional routine to generate a CO sensitivity profile for the user. The microprocessor may employ mathematical models to increase/decrease the rate at which the monitoring reaches a state of critical harm to a given individual. In ordinary monitoring mode, the display device might display a prediction of the time for a given individual at a given exposure level for reaching the alarm mode. The monitoring mode may distribute instructions to the individual to assist him/her to decrease the CO exposure.

The microcontroller adjusts the monitoring unit's CO detection sensitivity to comply with the user's profile.

The microcontroller 4 incorporates a clock module 10 and three or more timer modules 11 to 13. The timer modules 11 to 13 are driven from the clock cycles originating from clock module 10. The CO sensitivity profile generated by the microcontroller's application code will select the appropriate timer module for the profile generated. The CO sensitivity profiles are based upon the personal data 6 to 9 entered by the user.

The microcontroller's application code incorporates functional routines for determining the CO level thresholds, which effect different categories of users. Therefore, once a user has entered his/her personal data and the microcontroller 4 has created a CO sensitivity profile for the user, the air quality monitoring unit 1 is initiated and ready for use. When the monitoring unit 1 detects the presence of CO, which is beyond the determined threshold for the CO sensitivity profile of the user, the microcontroller 4 will initialise the relevant timer module for that category of CO sensitivity profile. The microcontroller 4 will initially start the counter with a time value representative of safe exposure time. The clock cycles from the clock within the microcontroller 4 will then trigger the timer module. During this countdown period a visual warning message is displayed on the display device 18 warning the user of the time remaining before reaching a critical exposure level. When the initial time value within the clock reaches a level at which symptoms might arise, the indications are tailored to reflect the potential harm. Furthermore instructions may be provided to assist the user to modify his/her exposure.

The system may also operate with a so called 'timed-out' state when an alarm 17 is initialised within the microcontroller 4, which then triggers a visual warning message to be displayed on the display device 18, warning the user to vacate the area immediately as they are now over-exposed to the CO level, for their CO sensitivity profile. This mode of operation would preferably automatically arise when the sensor detects a breach of a user's harm line.

The microcontroller 4 may also incorporate optional audible devices 20 which generate dedicated audible warnings for alerting the user either during the monitor mode of operation or during the alarm mode of operation. In the alarm mode of operation, the audible warning may encourage vacating the exposure location.

The display device 18 will preferably show the Critical Exposure/Evacuation time required for evacuating the area in which the CO threshold level was detected and ensuring the user is unharmed.

The functional threshold routines incorporated within the microcontroller 4 are:
>50 ppm=alarm or monitoring mode 3;
>25 ppm=alarm or monitoring mode 2;
>5 ppm=alarm or monitoring mode 1.

The processor may also be adapted to automatically convert PPM and duration into Carboxyhaemoglobin (COHb) levels. These levels are adjustable to take into account user type as well.

Listed below are some typical user categories, in which the user's CO sensitivity profile may reside:
Children, infants and foetuses;
People who have anaemia;
People who have heart or lung diseases;
People who have a higher rate of metabolism (caused by certain conditions such as hyperthyroidism). These people may be susceptible to a lower threshold such as 5 ppm as opposed to the usual 30-50 ppm, which would cause most alarms to trigger.

The user categories are essential when processing the appropriate critical exposure/evacuation time before symptoms or serious bodily harm occurs within the subject monitored. The microcontroller 4 may also tog the exact time when the CO was detected and the measured changes detected over a period of time, which equates to basic dosimeter functionality.

Alarm requirements are additional to monitoring requirements.

The main alarm requirements taken from EN50291 are:
At 30 ppm CO, the alarm must not activate for at least 120 minutes; (monitoring displays, indications, and actions arise during the entire period whilst a countdown is displayed);
At 50 ppm CO, the alarm must not activate before 60 minutes but must activate before 90 minutes; (monitoring displays, indications, and actions arise during the entire period whilst a countdown is displayed);
At 100 ppm CO, the alarm must not activate before 10 minutes but must activate before 40 minutes; (monitoring displays, indications, and actions arise during the entire period whilst a countdown is displayed);
At 300 ppm CO, the alarm must activate within 30 minutes. (monitoring displays, indications, and actions arise during the entire period whilst a countdown is displayed).

A display unit 18 shows in real time the CO measured within the vicinity. This provides visual confirmation that the unit is functioning properly. In addition to the CO measured display, the predicted time and its countdown before the user would suffer symptoms or harm is displayed. Optionally, the test button 21 on the unit will only test the display circuitry, not the sensor component itself.

Figure 2:
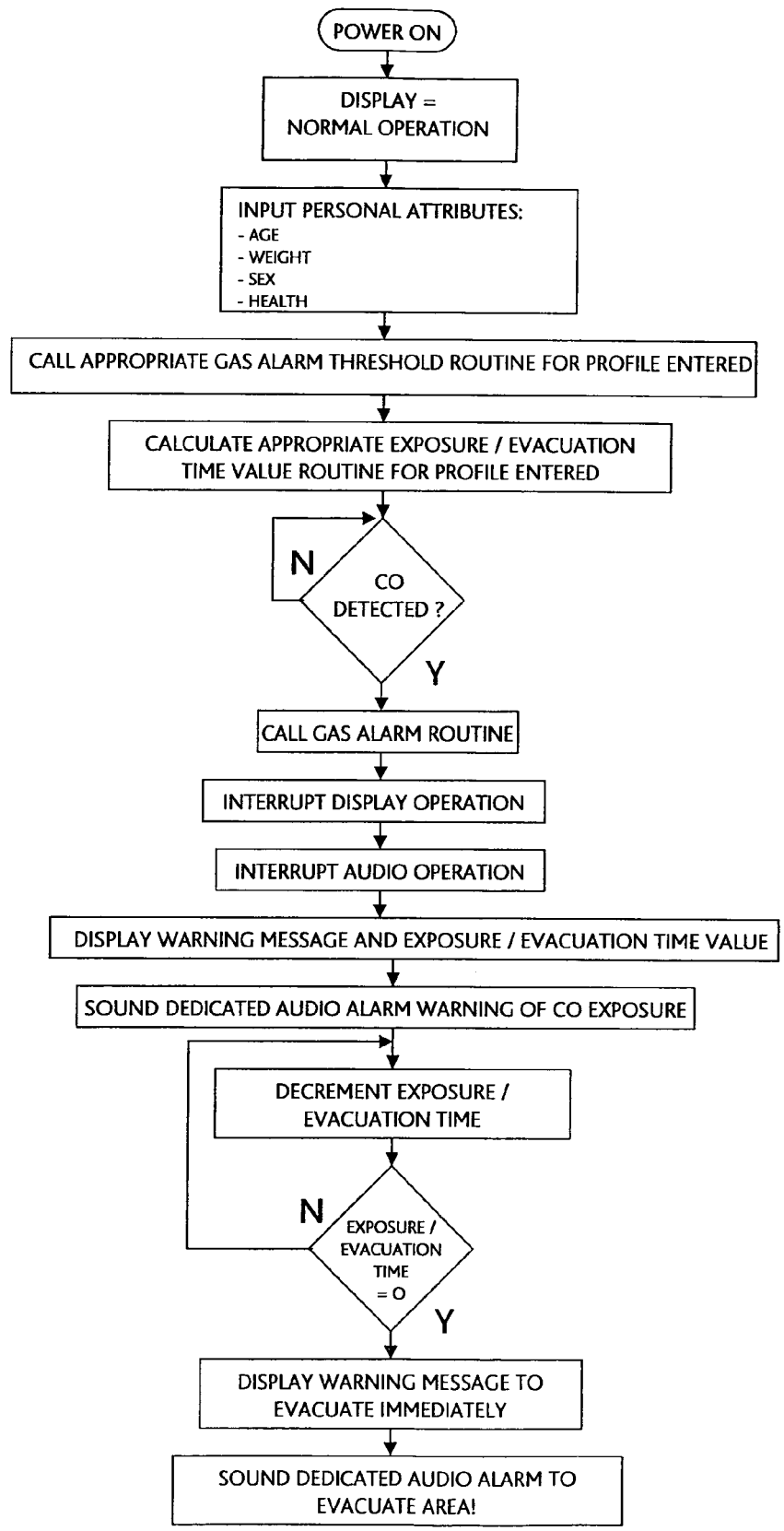
FIG. 2 shows a flow diagram representing the functionality of the air quality monitoring unit.

FIG. 2 shows a functional diagram for the embodiment shown in FIG. 1.

The device of FIG. 2 may activate the air quality monitor on "POWER ON".

Instead of inputting personal attributes, the device may be adapted to retrieve stored data or operate in default mode.

Instead of calling appropriate gas alarm threshold routine, the device may be adapted to calculate appropriate symptoms/harm parameters for a particular profile.

The device may also be adapted to detect or allow the input of other circumstances:
Activity levels (physical exertion or not; sleeping etc.);
Altitude, humidity, temperature, atmospheric pressure;
Smoker/non-smoker;
Other gases/pollutants;

Multiple countdown modes: one at least for the safe exposure period; and a second for the evacuation period; and Reminders; for example annual boiler check; annual sensor calibration.

The device may be adapted to display a symptom/harm profile.

The device may further be adapted to display the CO detected.

The device may further be adapted to display times for predicted symptom and/or harm exposure.

The device may further be adapted to display the above and prompt the user to pay attention.

If safe exposure time is exceeded then as a second mode of operation the device calls the gas alarm routine.

If the countdown is exceeded or not dealt with as a second mode of operation the device calls the gas alarm routine.

In a further embodiment, the following features are present in the monitoring device:

It is embedded within a host device;
Health inputs are facilitated such as medical conditions;
Activity levels (physical exertion or not; sleeping etc.);
Altitude, humidity, temperature, atmospheric pressure;
Other gases/pollutants;
Multiple countdown modes: one at least for the safe exposure period; and a second for the evacuation period; and
Reminders; for example annual boiler check; annual sensor calibration.

Figure 3:
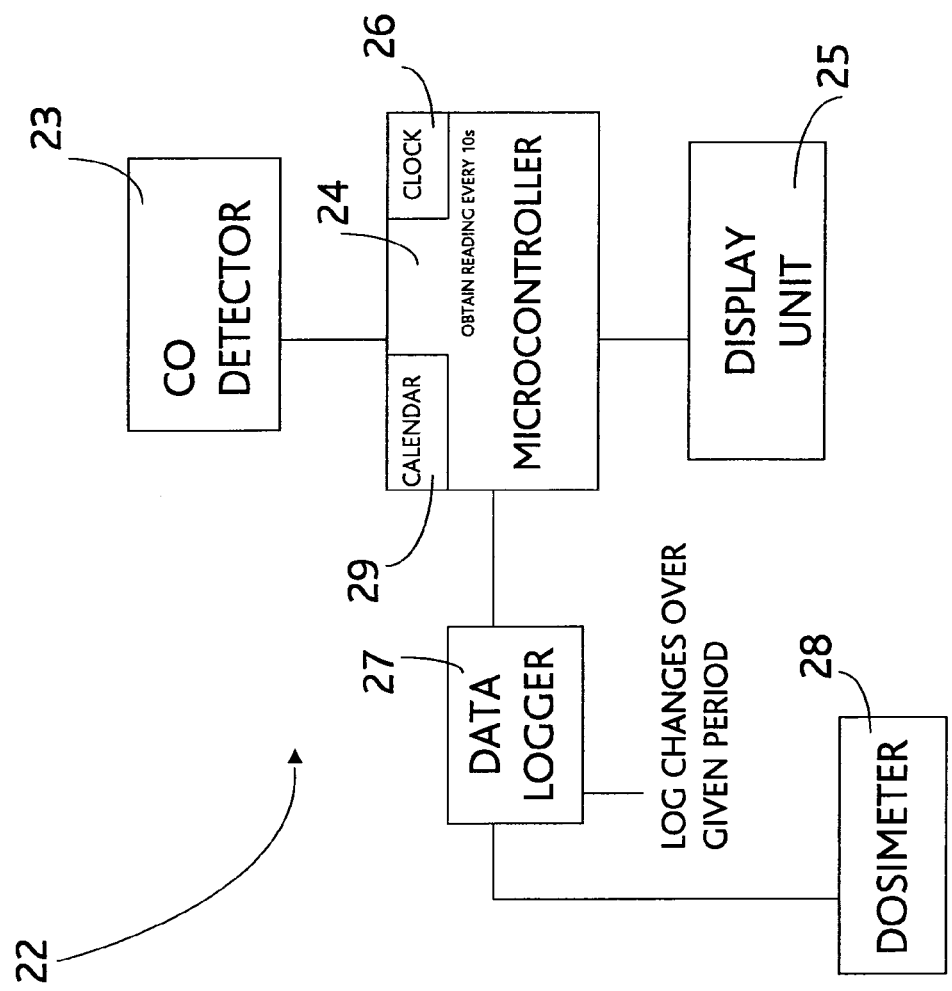
FIG. 3 shows a system block diagram representing the components of an air quality monitoring unit incorporating a data logging means.

FIG. 3 shows an alternative embodiment of the quality monitoring unit 22, which includes a CO detector 23, microprocessor 24 and display screen 25. The monitoring unit 22 also incorporates a clock module 26 within the microcontroller 24 and a data logger 27. The data logger 18 is shown to be located externally from the microcontroller 24. A dosimeter 28 is also shown to be located externally from the microcontroller 24.

The data logger 27 is a component that records data overtime. They are generally small and microprocessor based which incorporate data storage and sensors. However, they are also becoming available as functional module embedded within a microcontroller 24. Data loggers are normally interfaced with microprocessors and utilise dedicated routines to activate the data logger to analyse the collected data. The data may be analysed via a User interface device such as a Keypad or LCD. The data logger will automatically collect data when instructed. Upon activation the data logger will measure and record information for the duration of the monitoring period. This generates a comprehensive and accurate picture for the area being monitored.

The dosimeter 28 is a component that measures the overall exposure to CO over a given duration, in particular monitoring CO over long intervals of time. Since this is also microprocessor based, the dosimeter may be embedded as a functional module within the microcontroller 24.

The data logger 27 and dosimeter 28 log the CO levels at regular time intervals (typically every 10 seconds). Each log entry incorporates a CO measurement and time stamp.

When the CO level exceeds an appropriate threshold (e.g. de minimis/above normal), it initiates the relevant CO monitoring/exposure/alarm/evacuation alarm and initialises the following functions:

logs the exact moment of the hazard being detected and amount;
logs the measured changes over any given period;
meters the overall exposure to the CO contamination (the exposure level×duration) which provides a basic dosimeter function which indicates the amount of CO for a given period of time.

The microcontroller 24 incorporates a calendar function block 29, which stores monitored CO data in a day/date index for subsequent retrieval and processing by the microcontroller 24. The data within the data logger 27 may be retrieved by the microcontroller 24 for subsequent processing and transmission.

Figure 4:
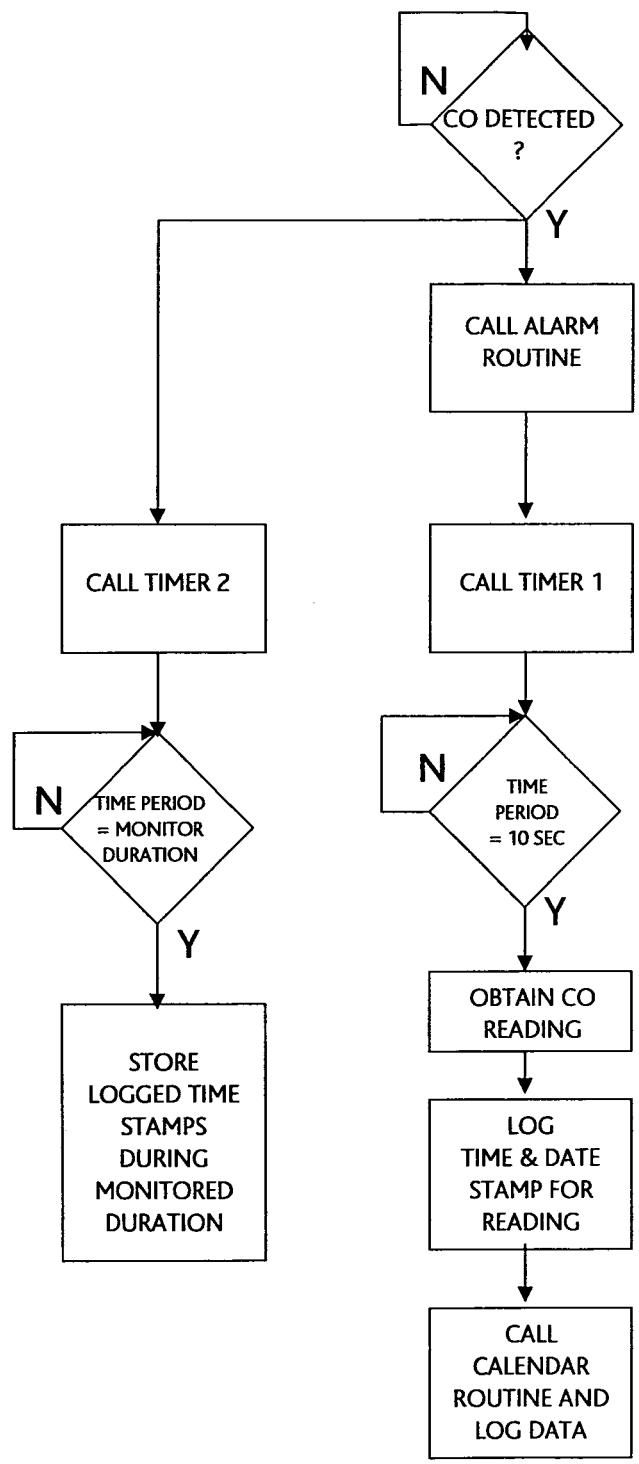
FIG. 4 shows a flow diagram representing the functionality of the air quality monitoring unit incorporating a data logging means.

FIG. 4 shows a functional diagram for the embodiment shown in FIG. 3.

Instead of "call alarm routine", the device may be adapted to prompt user for attention and/or launch a safe exposure routine.

Figure 5:
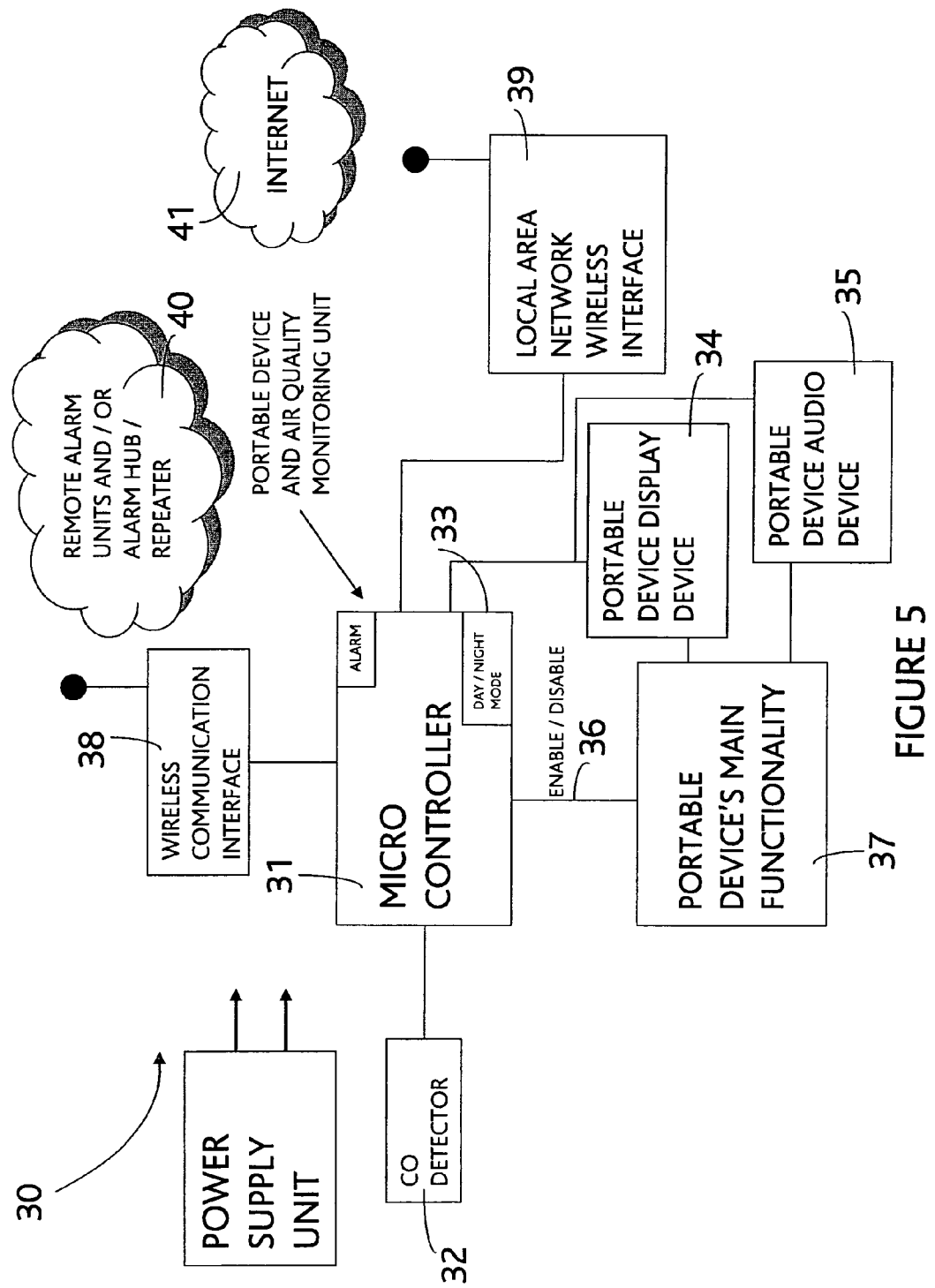
FIG. 5 shows a system block diagram representing the components of the air quality monitoring unit embedded within a portable device.

FIG. 5 shows an alternative embodiment of the air quality monitoring unit 30, which includes the monitoring unit embedded within a portable appliance. In an alternative embodiment, the monitoring unit is embedded in a fixed or fixed in use appliance and/or a mobile device. The portable appliance also incorporates a day/night mode functional module 33, a display device 34, an audio device 35 and an enable/disable control line 36 which is managed by the microcontroller 31. This enables the microcontroller 31 to enable/disable the portable device's main functionality 37. The microcontroller 31 is also coupled directly to a wireless communication interface 38 and a wireless local area network interface 39. The wireless communication interface 38 establishes wireless communication with peripheral devices such as additional alarm units and/or alarm hub/repeater units. The wireless communication would preferably be of a Personal Area Network (PAN) type, or alternatively or IEEE 802.11 communication protocols.

A PAN network is a computer based network used for communicating between computer devices, (typically used with mobile telephones and Personal Digital Assistants) close to one person. The broadcasting range of a PAN is typically a few meters. However, PANs can be used for communication among the personal devices themselves (intrapersonal communication), or for connecting to a higher level network and the internet. Wireless PAN networks are made possible with network technologies such as, IrDA, Bluetooth, UWB and Zigbee.

A blue tooth PAN is also known as a piconet and may incorporate up to 8 devices in a master-slave relationship. The first blue tooth device on the piconet is the master, and all the other devices are staves that communicate with the master device. A piconet typically has a range of 10 meters, although this may range up to 100 meters have been obtained under ideal circumstances.

When the CO sensor 32 detects the presence of CO, at a level which exceeds one of the preset alarm and/or monitoring thresholds, the micro-controller 4 activates disable/enable control line 36. This activation wilt interrupt the main functionality of the portable device. The microcontroller 31 then takes control of the portable device's display and audio units. The microcontroller 31 then determines whether it is night or day. This may be determined by calling a routine which calculates the time and day from an incorporated clock and calendar routines, or by utilising external components such as a photo diode for detecting light. During day operation, the portable display device is set to its highest luminescence level and initialises an audio alarm which ascends sufficiently quickly but simultaneously ensures that it captures the user's awareness without scaring or creating shock. During night operation, the portable display device is set to a lower luminescence level and initialises an audio alarm which ascends at a slower rate to give a gradual presence to user, without scaring them or causing shock.

When CO is detected at a level which exceeds one of the preset alarm thresholds, the microcontroller 31 will initiate the wireless communication interface 38. The microcontroller 31 wilt then broadcast an alarm signal from the wireless interface 38 to any remote alarm units and/or hub/repeater units 40 within its broadcasting range. Therefore, the portable device may be used within an area which is covered by a broadcasting hub and if the portable device detects the presence of CO it will trigger any remote alarm unit within range.

The microcontroller 31 will also initiate the local or wide area network wireless interface 39. The microcontroller wilt then broadcast an alarm signal from the local or wide area network interface 39 to a wireless router within its broadcasting range. Therefore, it enables the alarm information and any logged data to be uploaded onto the internet or network 41, to a dedicated web page or e-mail account for subsequent retrieval and analysis. Alternatively, when the alarm activation has been detected, web based cameras (web cams) are enabled to stream visual data from the incident area to enable a third party to monitor the situation safely from a remote location.

Typical portable devices into which this air quality monitoring unit could be embedded are:
Portable clocks;
Personal Digital Assistants (PDAs);
Global Positioning Systems (GPS);
Torches;
Breathing apparatus for emergency personnel;
Medical devices for medical personnel;
Baby monitors;
Barometers;
Thermometers;
Door chimes and/or doorbell systems;
Fire alarm systems;
Intruder alarm systems;
Dictation machines;
Diagnostic tools or equipment;
Attack alarms;
Power toots;
Travel items such as travel irons;
Calculators;
Boilers;
Bikes;
Personal entertainment units such as personal stereos and MP3 players;
The portable unit may be further enhanced by enabling a webcam or any monitoring surveillance system to be activated if the alarm is activated and therefore enabling a visual log to be taken of the circumstances.

Figure 6:
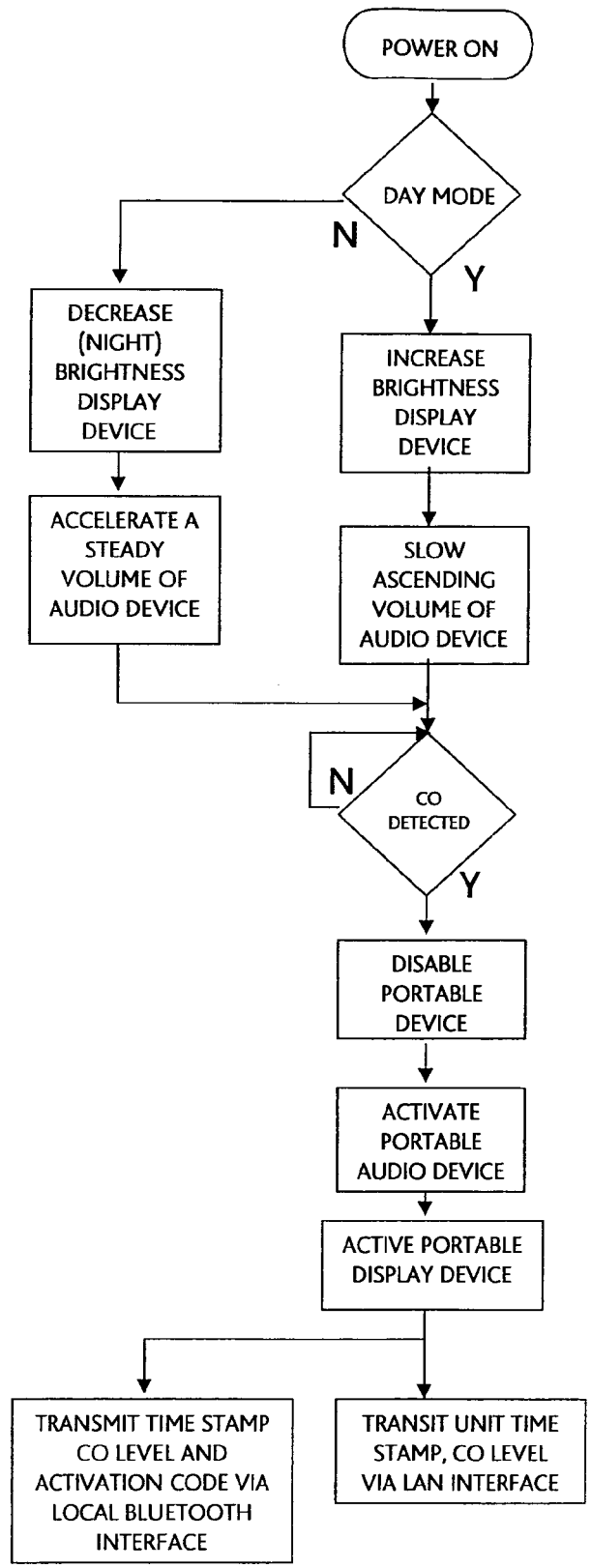
FIG. 6 shows a flow diagram representing the functionality of the air quality monitoring unit embedded within a portable device.

FIG. 6 shows a functional diagram for the embodiment shown in FIG. 5.

The device of FIG. 6 may be adapted to allow the input of personal data and to predict based on said personal data a safe threshold for monitoring CO. A countdown of the monitoring time before symptoms and harm occurs is also envisaged.

Figure 7:
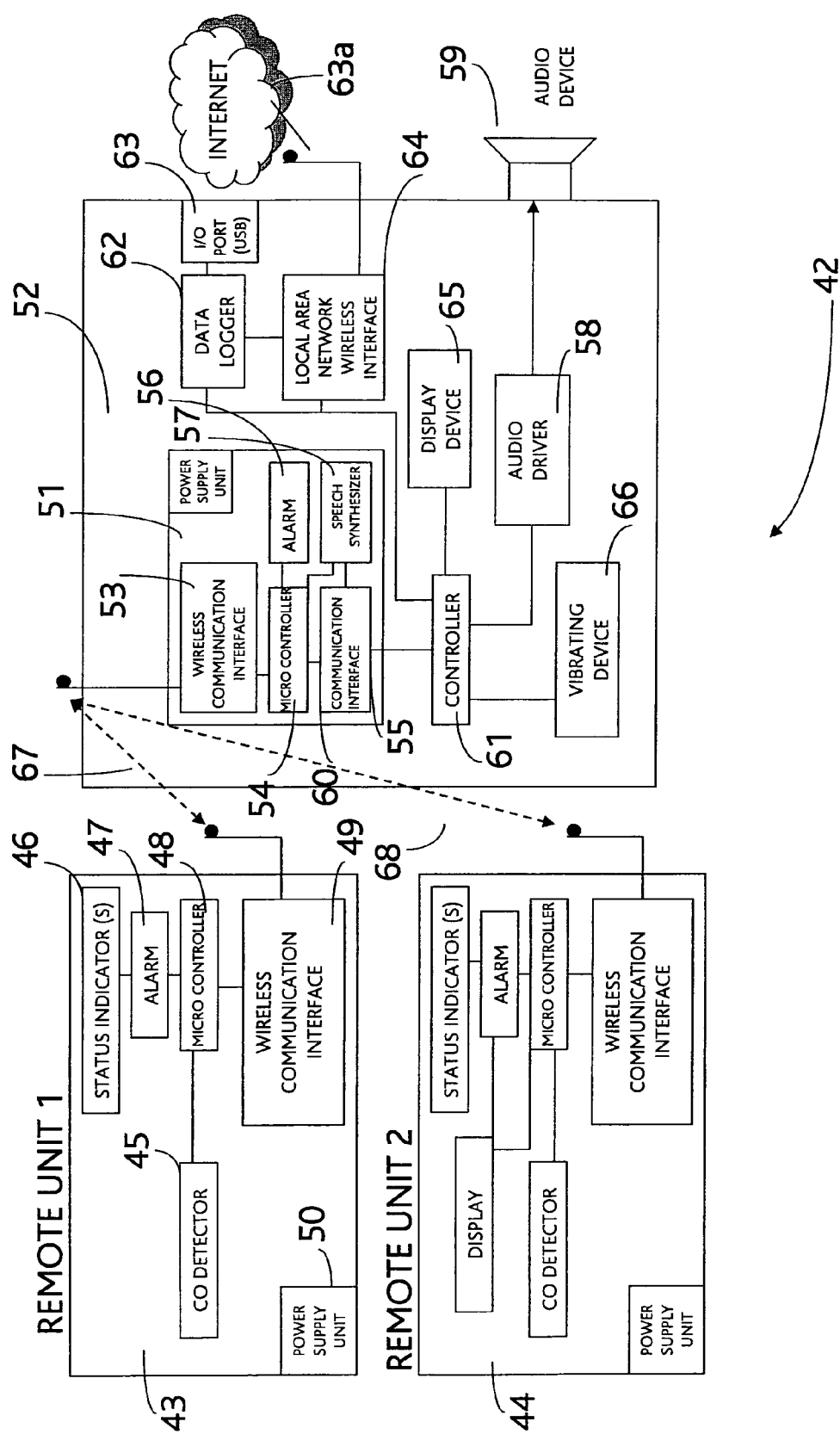
FIG. 7 shows an alternative system block diagram representing the components of the air quality monitoring unit embedded within a portable device.

FIG. 7 shows an alternative embodiment of the air quality monitoring unit 42. This embodiment incorporates two remote sensing units 43 and 44. Both units are identical and incorporate a CO detector or sensor 45, status indicator 46, alarm module 47, a microcontroller 48, a wireless communication interface 49 and a Local power supply 50. Wireless communication link 67 indicates a communication channel link between remote unit-1 43 and the hub unit 51 embedded within the portable device 52. Wireless communication link 68 indicates a communication channel link between remote unit-2 44 and the hub unit 51 embedded within the portable device 52

When one of the remote sensing units 43 and/or 44 detects the presence of CO, the micro-controller 48 activates the alarm module 47. The alarm module 47 then subsequently drives the status indicator 46. The status indicator may comprise green and red indicators which are mounted externally on the monitoring unit 42. The green indicator may represent an "OK" state for no CO gas present and the red indicator a "not OK" state for CO gas detected and present. The indicators also enable visual verification of a triggered alarm when investigating the source of CO emission. The microcontroller 48 will then transmit the remote sensing unit's alarm status at regularly timed intervals from the wireless communication interface 49 to the hub unit 42.

For this embodiment, the hub unit 51 is incorporated within a portable device 52, which is similar to the portable devices mentioned in FIG. 5. The hub unit 51 incorporates a wireless communication interface 53, a controller 54, communication interface 55, and an alarm module 56, and a speech synthesiser 57. On receiving a remote sensing unit's alarm status, via the hub unit's wireless communication interface 53, the alarm data is then extracted and communicated to the microcontroller 54. The microcontroller then activates alarm module 56 and speech synthesiser module 57. The processed alarm messages are stored within the alarm module 56. The microcontroller 48 utilises this data to monitor the alarm status of the installation. The microcontroller 54 communicates warning data to the speech synthesiser module 57. This data represents an audio voice message, which is then communicated to an internal communication interface 60. The communication interface 60 connects the internal hub to the portable device's circuitry, therefore enabling the warning data to be communicated to other non-hub unit components within the portable device 52. The warning data is communicated to the portable device's controller module 61. The device's controller 61 then communicates the warning message to audio driver module 58. The audio driver module then reprocesses the data to drive the audio device 59. The audio driver may reprocess the data to drive a digital audio device, or by converting the warning data into an analogue signal via a digital to analogue converter (DAC) if the audio device is a conventional analogue speaker. The audio driver module 58 then communicates the audio voice message to the audio device 59, which then broadcasts the warning message to the user. The hub unit's microcontroller 54 interrupts the portable device's controller 61 at regular time intervals (typically every 10 seconds) to communicate alarm data to the portable device's data logger 62. The alarm data incorporates the time stamp of the alarm and other alarm attributes. The data stored within the data Logger 62 may be retrieved via an input/output port (I/O port) 63, which is mounted externally on the monitoring unit 42. The I/O port may be typically a Universal Serial Bus Port (USB). The alarm data is also communicated to a local area network wireless interface 64. Therefore, connecting to the internet 63a via a wireless router within the broadcasting range of the wireless interface 64 to upload the data log to a dedicated webpage/e-mail account for remote access, subsequent retrieval and remote monitoring.

The hub unit's microcontroller 54 is indirectly attached to the portable unit's display device 65 and vibrating device 66. The vibrating device would be typically connected to the outer case of the monitoring device 42. Therefore, when the hub unit's microcontroller 54 processes a CO alarm event, it communicates the data, which represents a visual warning message on the portable unit's display device 65, via the portable device's controller 61. Alternatively, the hub unit's microcontroller 54 communicates data, which represents a visual warning message to a display device decoder which then converts the data into a visual warning which is then communicated to the display device 65. The visual and/or audio message will then inform the user to vacate the area immediately and if for some reason cannot see or hear the warning messages, and the portable device is located on the person, the vibrating device 66 will provide an extra sensory alert to the subject that communication is trying to established. Therefore, their attention is drawn to the display and/or audible devices located on the portable device.

Figure 8:
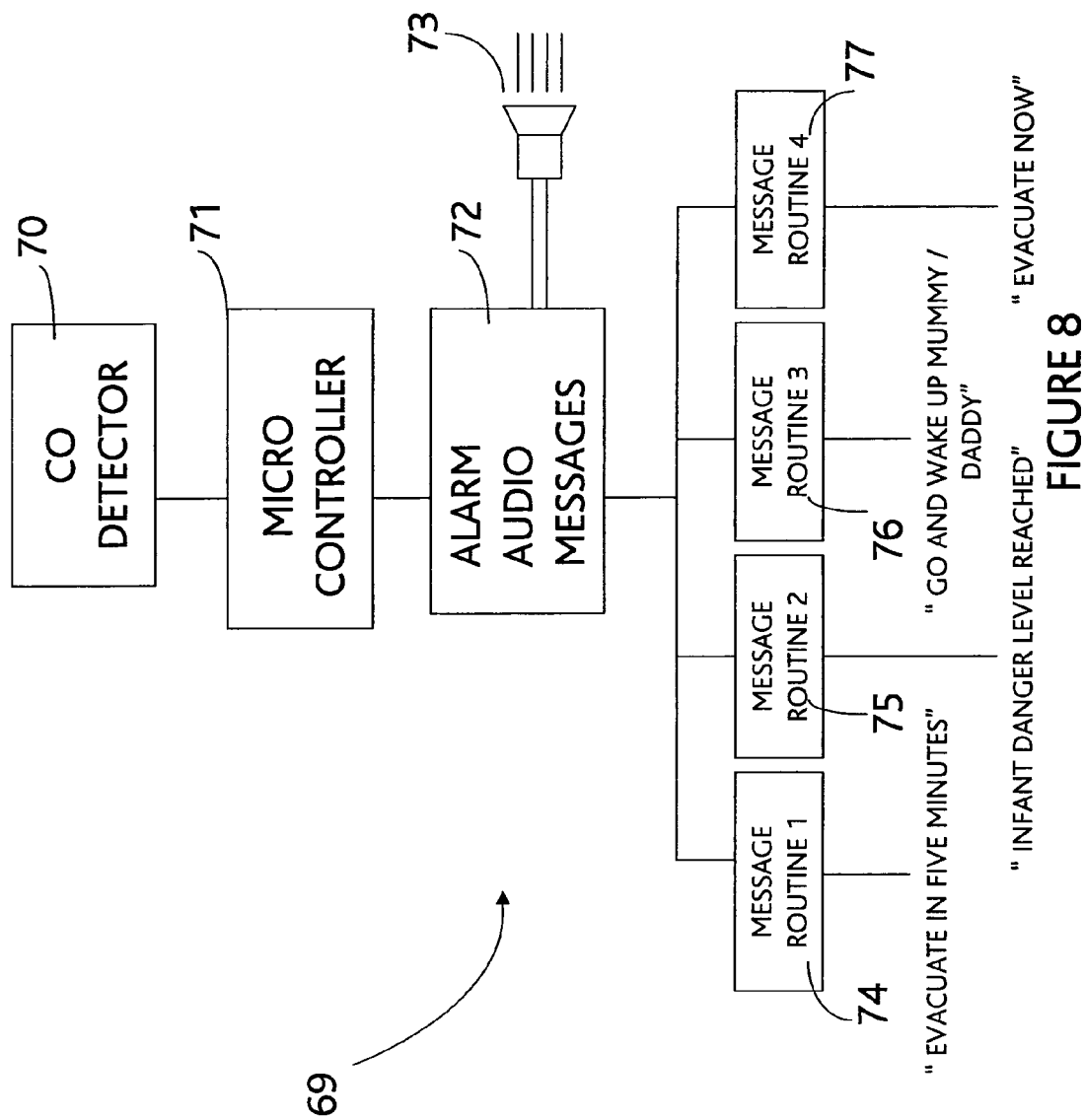
FIG. 8 shows a system block diagram representing the components of the air quality monitoring unit incorporating selectable alarm messages.

Typical portable devices for hosting this embodiment are:
Door chimes;
Clocks and/or Radios;
PDAs;
GPS;
Door chimes;
Boilers;
Thermometers;
Dictation machines;
Transport devices;
Personal entertainment units such as personal stereos and MP3 players;

FIG. 8 shows an alternative embodiment of the quality monitoring unit 69. This embodiment shows that when the CO detector 70 detects the presence of CO gas, the microcontroller 71 generates an audible warning message 72, which is then communicated to the user, via an audible device 73. The audible warning messages are stored within the microcontroller 71 as routines 74 to 77. Each warning is dedicated to a category of user. During an alarm event, the microcontroller 71 will call up the relevant message routine for the category of user. The category of user is determined by entering the user's personal attributes as shown in FIG. 1 The figure shows that message routine one 74 "evacuate in five minutes" is intended for evacuating an area of low CO contamination within a safe period. Message routine two 75 "Infant danger level reached" is intended for use where the CO level has reached a danger level for a young child. Message routine three 76 "go and wake up mummy and/or daddy" or "wake up mummy/daddy and call [999] for help!!" is intended to communicate an easy to understand message to a young child, instructing it to wake its mother and/or father during an alarm event. Message routine four 77 "evacuate now" is intended for use where CO levels are at a dangerous level within the immediate vicinity.

Figure 9:
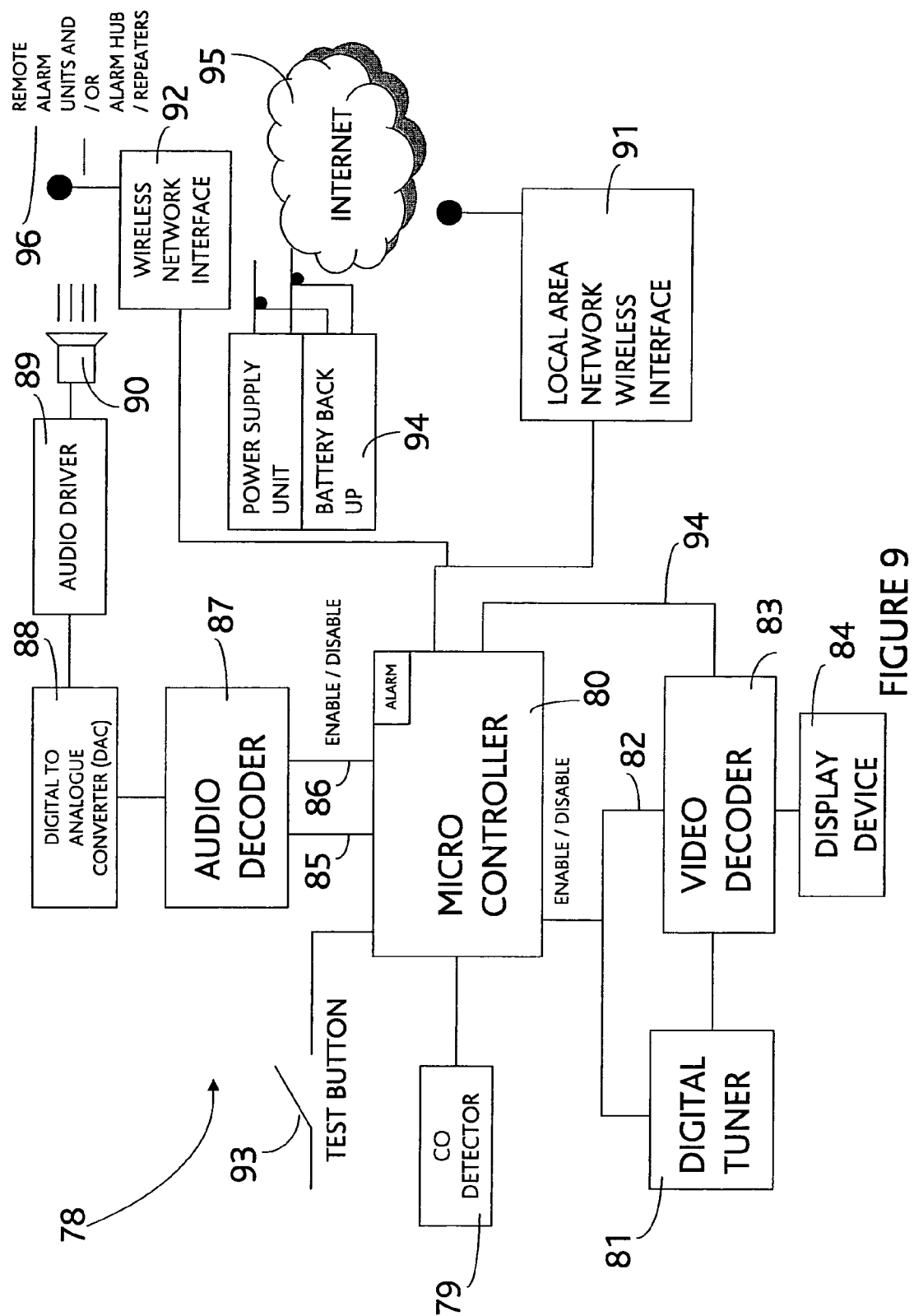
FIG. 9 shows a system block diagram representing the components of the air quality monitoring embedded within a television unit.

FIG. 9 shows an alternative embodiment of the air quality monitoring unit 78. This embodiment shows the monitoring unit 78 embedded within a visual device, such as a television unit or computer screen. The CO detector 79 is coupled to a microcontroller 80. The microcontroller is coupled to a digital tuner 81 via an enable/disable control line 82. The digital tuner 81 is coupled to a video decoder 83. The microcontroller 80 is coupled to the video decoder via the enable/disable control line 82. The video decoder 83 is coupled to a display device 84. The microcontroller 80 is coupled to an audio decoder 87 via a data coupling 85 and an enable/disable control line 86. The audio decoder 87 is coupled to a digital to analogue converter (DAC) 88. The DAC 88 is shown to be a component which is external to the audio decoder 87. However, the DAC 88 may be embedded as a functional module within the audio decoder 87. The DAC 88 is coupled to an audio driver 89, which subsequently drives an audio device 90. The microcontroller 80 is coupled to a local area network interface 91. The microcontroller 80 is also coupled to a wireless network interface 92. A test button 93 is coupled to the microcontroller 80.

The digital tuner 81 is the component that allows the television or computer (if fitted with a tuner card) to receive signals via broadcast airwaves, satellite or cable transmission. The signals are then translated into a signal, which the video decoder can process and display. The digital tuner 81 may also be used within digital radio units to tune into digital radio stations.

The audio decoder 87 is the component that compresses/decompresses digital audio data according to the audio file format or audio streaming format. This component is also known as an audio codec, due to the combination of the 'coder-decoder' functions. The audio decoder utilises an algorithm to represent the audio signal, with the minimum number of bits, while retaining quality. This reduces the storage space and the bandwidth required for the communication of the stored audio file.

The DAC 88 is the component that converts the digital audio data (binary code format) to an analogue signal (which comprises conventional current, voltage or electrical charge). The analogue signal, which represents the audio message, is communicated to the audio device 90 via an audio driver 90.

The video decoder 83 is the component that compresses/decompresses digital video. The compressing functionality employs lossy data compression techniques. The term lossy refers to a reduction in image quality due to digital data losses during the conversion process. This component is also known as a video codec, due to the combination of the 'coder-decoder' functions. The audio decoder utilises an algorithm to represent the audio signal, with the minimum number of bits, while retaining quality. This reduces the storage space and the bandwidth required for the communication of the stored visual/image file. The decoded digital video, which represents the visual message, is communicated to the display device 84.

This embodiment shows that when the CO detector detects the presence of CO gas, the microcontroller 80 generates both audible and visual warnings to alert the user of the presence of CO gas. The microcontroller 80 calls a routine, which activates the enable/disable control line 82 that disables the digital tuner 81. Disabling the digital tuner 81 blocks all the entertainment channels (television and/or radio), which would distract the user's attention away from the alarm message. Also, by activating the enable/disable control line 82, the microcontroller 80 enables the video decoder 83. The microcontroller 80 communicates the visual digital data to the video decoder 80 via a data coupling 94. The visual digital data is decoded into a digital format which is compatible with the display device 84. The display device would preferably be of a digital type, therefore enabling the decoded visual data to be directly coupled to it from the video decoder 83. The decoded visual data represents the alarm message that is to be displayed upon the display device, to inform the user of the presence of CO gas.

When the microcontroller 80 disables the digital tuner 81, it activates the enable/disable control line 86, which enables the audio decoder 87. The microcontroller 80 communicates the audio digital data to the audio decoder 87 via a data coupling 85. The audio digital data is decoded into a digital format, which is compatible with the DAC 88. The audio digital data is then converted into an analogue signal, which represents the audio alarm message. The analogue audio alarm message will not be sufficient to drive the analogue audio device 90. Therefore, the analogue audio alarm message is boosted/amplified by the audio driver component 89 to ensure it is at a sufficient level to drive the audio device 90. The analogue audio alarm message represents the alarm message to inform the user of the presence of CO gas.

Therefore, when CO gas is detected, the microcontroller 80 will log and upload the alarm event data to the internet 95, via the Local area network wireless interface 91. The alarm data will be uploaded to a dedicated website or control centre for observation and retrieval for subsequent analysis. The microcontroller 80 will transmit the alarm event, via the wireless network interface 92. The alarm event will be transmitted to other remote alarm units and/or alarm hub/repeaters 96. The wireless network interface would typically employ Bluetooth™ or IEEE 802.11 communication protocols. Therefore, it enables the air quality monitoring unit 78 embedded within a television/computer screen to interact with any CO remote alarm units and/or remote alarm hub/repeaters 96 to trigger an alarm system to alert users of the presence of CO gas.

Typical visual-audio devices for hosting this embodiment are:
Televisions;
Laptops;
Personal computers (PC) and PC monitor screens;
Gaming devices;
Personal entertainment units such as personal stereos and MP3 players;

Optionally, the test button 93, when depressed, will test the microcontroller 80 and associated circuitry, but not the CO detector itself. The power supply unit 94 is shown to incorporate a battery back up function module to ensure that the air quality monitoring unit's functionality is maintained when the host audio device is in a powered down state.

Figure 10:
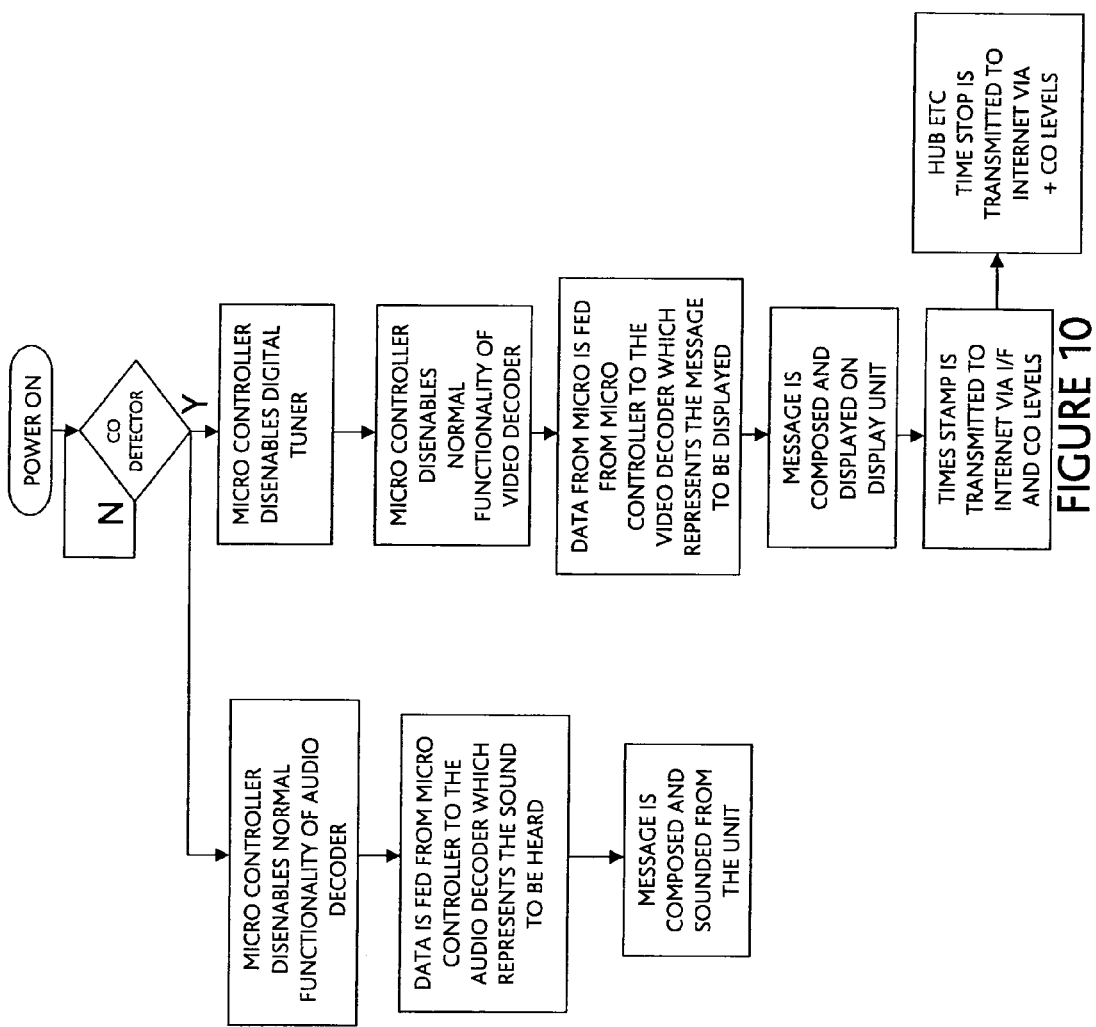
FIG. 10 shows a flow diagram representing the functionality of the air quality monitoring unit embedded within a television unit.

FIG. 10 shows a functional diagram for the embodiment shown in FIG. 9. Alternatively, the device of FIG. 10 may be adapted to also incorporate the following operational steps:
ON/Activated;
Default CO sensitivity profile.
User specific sensitivity profile (see examples above).
Calculate: a) symptom; b) harm; lines and/or thresholds;
CO sensed above normal?
Prompt the user for attention;
Predict/countdown safe exposure times;
Safe exposure times approaching {15-30 minutes};
Initiate traditional alarm sequence with device interrupts/audio/visual alarms/remote monitoring/alarm/appliance switch off etc.

Figure 11:
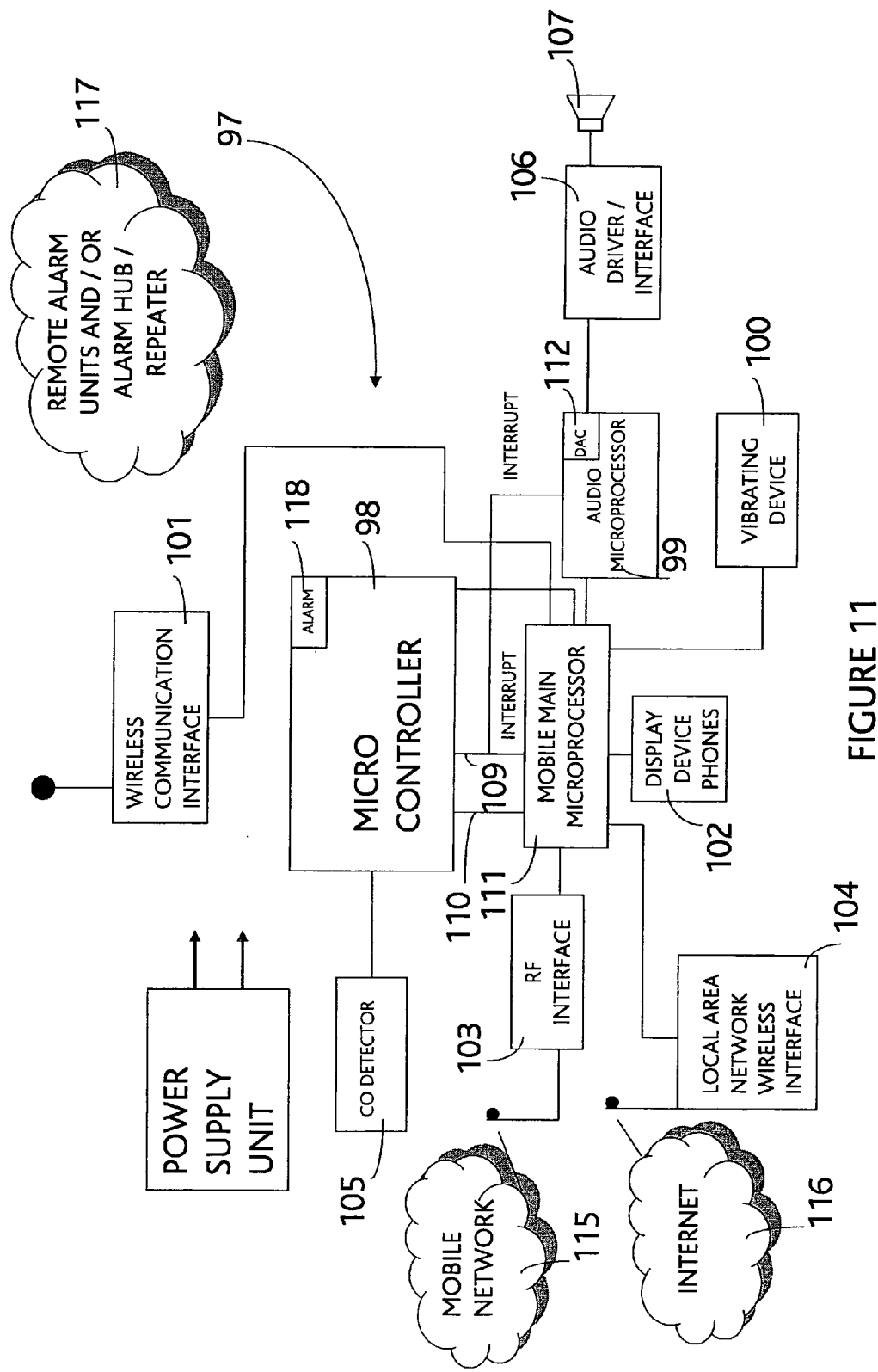
FIG. 11 shows a system block diagram representing the components of the air quality monitoring embedded within a mobile phone.

FIG. 11 shows an alternative embodiment of the air quality monitoring unit 97. This embodiment shows the monitoring unit 97 embedded within a mobile phone or any other communication device. The microprocessor 98 is coupled to the mobile phone's main processor 111. The mobile phone's main microprocessor 111 is coupled to a display device 102, an audio microprocessor 99, a vibrating device 100, a Radio Frequency (RF) interface 103, a local area network wireless interface 104 and a wireless communication interface 101. The audio microprocessor 99 is coupled to an analogue interface 106. The analogue interface 106 is then subsequently coupled to audible devices, such as a speaker 107 or microphone 108.

The vibrating device 100 is the component that provides a means of communicating an alarm event by feel. The two primary uses for a vibrating alert are when the user cannot hear the audible device, or when the user requires a more discreet notification of an alarm event. The vibrating device 100 typically comprises a small electric motor connected to eccentric (unbalanced) weight. Vibrating device 100 is helpful for those suffering from a hearing impediment.

This embodiment shows that when the CO detector 105 detects the presence of CO gas, the microcontroller 98 calls a routine, which activates the interrupt control line 109 that interrupts the normal operation of the mobile phone's main microprocessor 111. The microcontroller 98 then communicates the alarm data to the mobile phone's main microprocessor 111 via a data coupling 110. The microcontroller 98 then takes control of the mobile phone's main microprocessor 111 and manages the processing of the alarm data to the display device 102, Vibrating device 100, local area network wireless interface 104, RF interface 103, audio microprocessor 99 and wireless communication interface 101. The alarm data to the display unit 102 represents the alarm warning to be displayed to the user. The alarm data to the audio microprocessor 99 represents the alarm warning to be broadcasted to the user. The audio microprocessor 99 converts the alarm data into an analogue form, which is then communicated to an audio driver interface 106. The audio driver interface 106 boosts/amplifies the analogue alarm to enable it to drive the mobile phone's speaker 107. The microprocessor 98 activates the vibrating device 100 during an alarm event, for communicating to the user that an attention request is required. The RF interface 103 converts the alarm data into short message service (SMS) format, which is then transmitted across a mobile network 115 to a dedicated number for informing a remote user that an alarm event has occurred. SMS also enables the alarm data to be stored remotely for subsequent retrieval and analysis. The mobile phone's main processor 111, via the display unit 102, displays all functional data, alarm and text messages transmitted to the user. The local area network wireless interface 104 enables the microcontroller 98 to access the internet 116, via the mobile phone's main processor 111. The alarm data is uploaded to a dedicated webpage/e-mail address for remote monitoring, remote storage and/or subsequent analysis. The wireless communication interface 101 enables the microcontroller 98 to establish communication with remote alarm units and/or alarm hub repeaters 117, via the mobile phone's main processor 111. The alarm data is transmitted to the remote alarm units and/or alarm hub repeaters 117. The wireless network interface would typically employ Bluetooth™ or IEEE 802.11 communication protocols. Therefore, enabling the air quality monitoring unit 78 embedded within a mobile phone or pager device to interact with any remote alarm units and/or remote alarm hub/repeaters 96 to trigger an alarm system to alert users of the presence of CO gas.

Once the CO detector 105 detects CO gas in the local proximity of the mobile phone, the microcontroller 98 then activates an internal monitoring module 118, which interrupts both the mobile phone's main microprocessor 111 and audio microprocessor 112. While the interrupt is activated, both the mobile phone's main microprocessor 111 and audio microprocessor 112 are managed by the microcontroller 98. The microcontroller 98 generates display and sound warnings to the user; activate the vibrating device as an extra sensory alarm warning to the user. During the alarm event the alarm data will be transmitted over a wireless communication interface 101 to enable peripheral devices within the broadcasting range of the interface 101. During the alarm event the microcontroller 98 may also call a stored/emergency number with an automatic SMS message and/or voice message, via mobile network 115 to inform the user of the alarm event. The microcontroller 98 would be able to send warning messages to remote web pages, which log and store data for subsequent data retrieval and analysis. Therefore allowing third parties to monitor the situation and activate remote webcams for streaming visual data to enable them to remotely monitor the situation.

Typical communication devices for hosting this embodiment are:
Emergency radio sets (TETRA compatible);
Mobile phones;
Personal digital assistants (PDAs);
Global positioning systems (GPS).

The air quality monitoring unit 97 may be embedded within the mobile phone's main microcontroller 98; thereby eliminating the requirement for discrete quality monitoring unit components.

Figure 12:
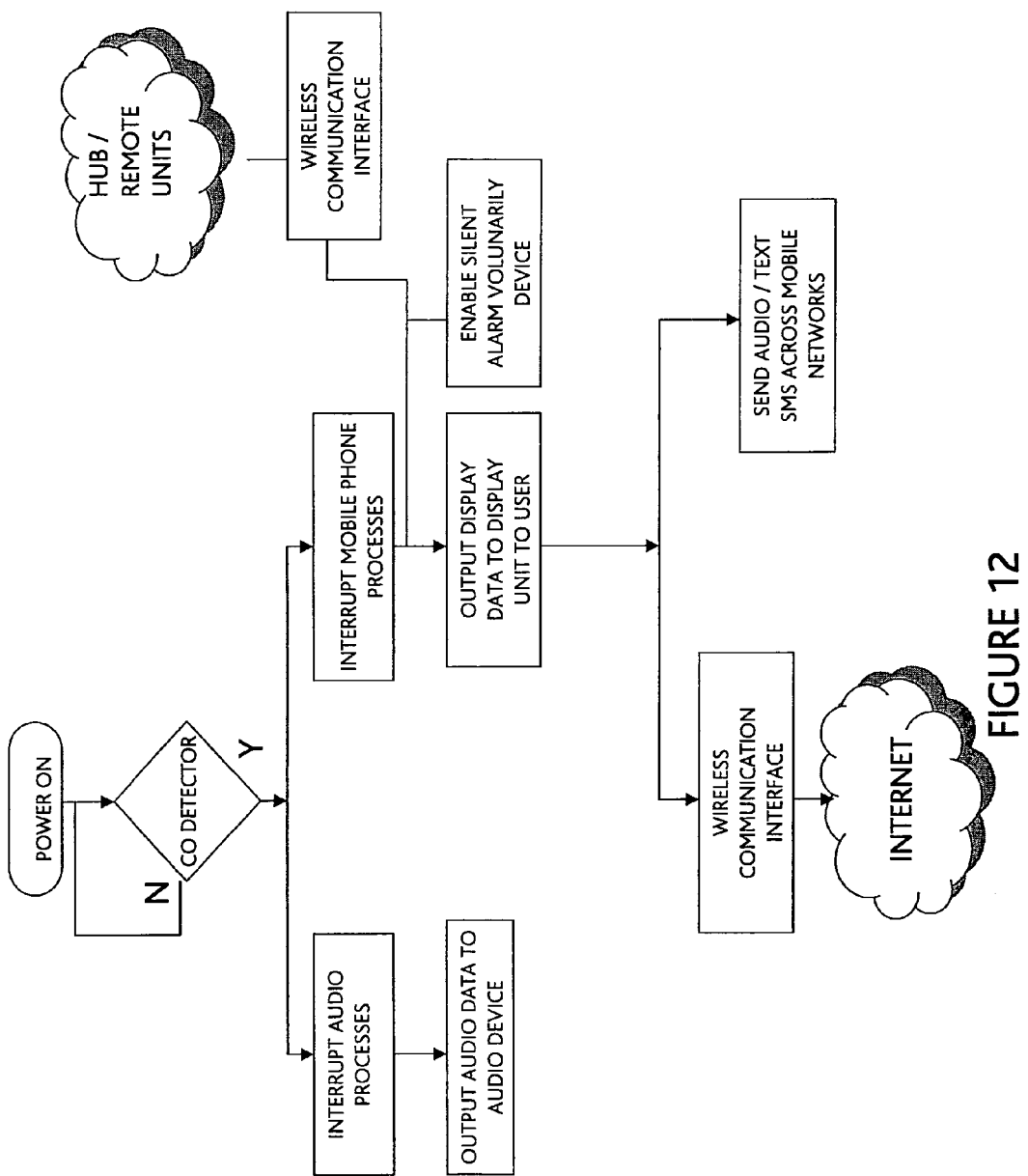
FIG. 12 shows a flow diagram representing the functionality of the air quality monitoring unit embedded within a mobile phone.

FIG. 12 shows a functional diagram for the embodiment shown in FIG. 11.

Alternatively, the following operational steps are envisaged in the embodiment of FIG. 12:
  ON/Activated;
  Default CO sensitivity profile.
  User specific sensitivity profile (see examples above).
  Calculate: a) symptom; b) harm; lines and/or thresholds;
  CO sensed above normal?
  Prompt user for attention;
  Predict/countdown safe exposure times;
  Safe exposure times approaching {15-30 minutes};
  Initiate traditional alarm sequence with device interrupts/audio/visual alarms/remote monitoring/alarm/appliance switch off etc.

Figure 13:
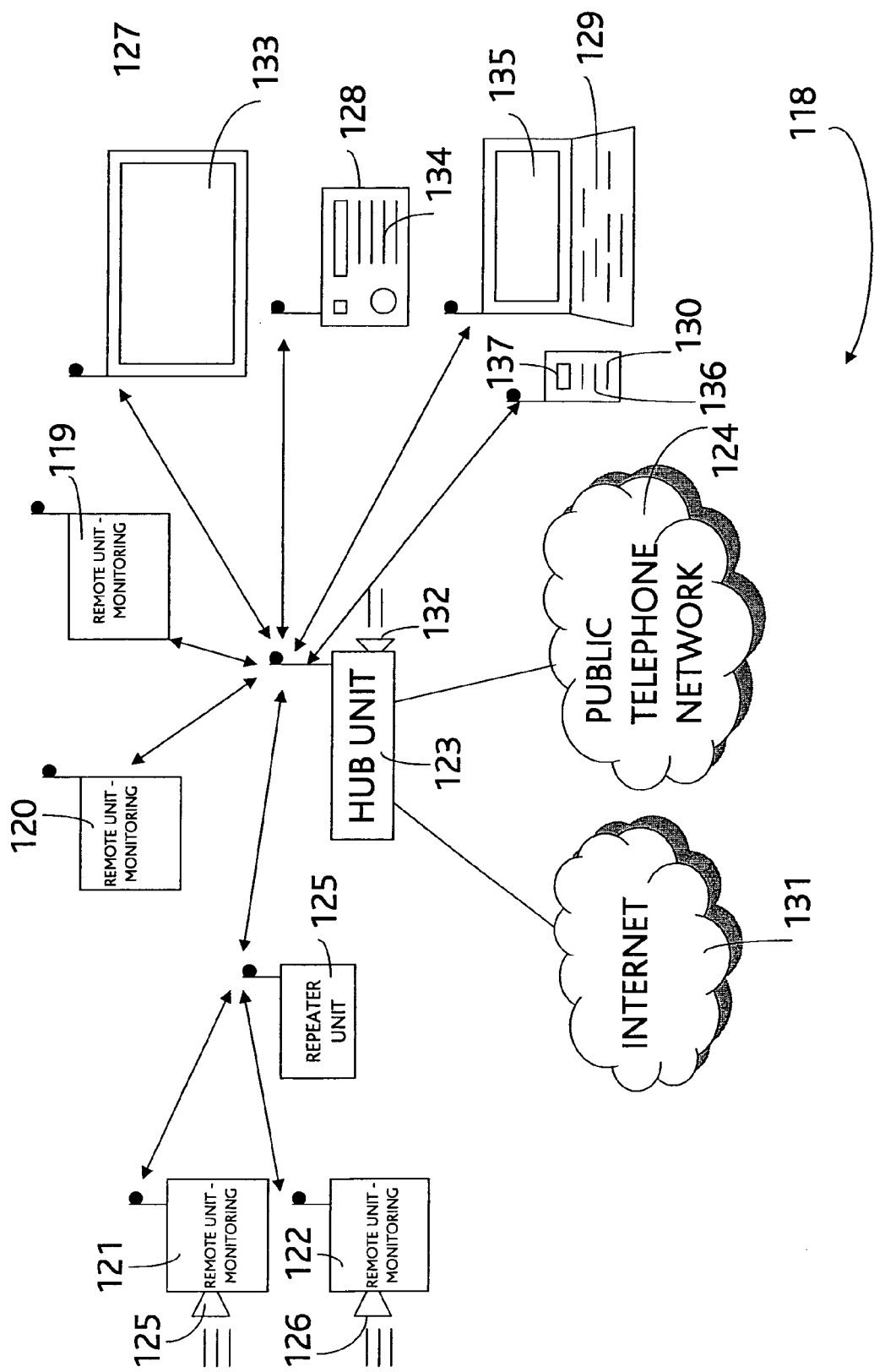
FIG. 13 shows a system block diagram of an air quality monitoring unit configured in a hub network.

FIG. 13 shows a number of air quality monitoring units 119 to 122 implemented in an air quality monitoring system 118. The monitoring system 118 is configured around a central hub unit 123. The hub unit 123 provides the monitoring system 123 with an interface to the public telephone network 124 for transmitting alarm event data to a remote site for subsequent retrieval, further analysis on or off site and enabling remote monitoring means such as cameras, surveillance equipment etc. The hub unit provides an interface to the internet 131 for uploading alarm event data to a dedicated webpage for subsequent retrieval and further analysis enabling remote monitoring means such as web cams. The hub unit is shown to be connected in two way communication with the remote monitoring units 119 to 122, via wireless links typically Bluetooth™ or IEEE 802.11. The hub unit 123 is shown to be in two way communication with a repeater unit 125, which enables the remote monitoring units 121 and 122 to be located beyond the broadcasting range of the hub unit 123. The remote monitoring units 121 and 122 are shown to incorporate audible devices 125 and 126. The hub unit 123 is shown to be in two way communication with air quality monitoring circuits embedded in a number of host appliances, such as a television 127, a radio 128, a computer/laptop computer 129 and a mobile phone 130. The hub unit is shown to incorporate an audio device 132.

When the monitoring system 118 detects the presence of CO within the local proximity of an air quality monitoring unit, an alarm event message is transmitted to the remote monitoring units 119 to 126. Communication with remote monitoring units 125 and 126, which are beyond the broadcasting range of the hub unit 123, is maintained by repeater unit 125. The audible warning message to the user is broadcasted from all the audible devices 125, 126 and 132. The visual warning message to the user is displayed to the user from display units on the remote monitoring units 119 to 126 and hub unit 123. The remote monitoring units may incorporate a single coloured indicator, typically red, to indicate which remote monitoring unit 119 to 126 detected the presence of CO gas. The transmitted alarm event data triggers a visual and or audio warning message to the user via the television's screen 133 and speaker. The transmitted alarm event data triggers an audio warning message to the user via the radio's speaker. 134. The transmitted alarm event data triggers a visual and or audio warning message to the user via the computer's screen 135 and speaker. The transmitted alarm event data triggers a visual and or audio warning message to the user via the mobile phone's screen 137 and speaker 136.

The monitoring system may incorporate alarm zone functionality, wherein a dedicated alarm event message from the hub unit would activate remote monitoring units within a predetermined zone; thereby enabling other users to function within other detection zones, without any interference from an activated zone.

The following operational steps are envisaged in a further embodiment of the invention:
  ON/Activated;
  Default CO sensitivity profile.
  User specific sensitivity profile (see examples above).
  Calculate: a) symptom; b) harm; lines and/or thresholds;
  CO sensed above normal?
  Prompt user for attention;
  Predict/countdown safe exposure times;
  Safe exposure times approaching {15-30 minutes};
  Initiate traditional alarm sequence with device interrupts/audio/visual alarms/remote monitoring/alarm/appliance switch off etc.

The following embodiments are envisaged:

Integrated Detector

Incorporating the air quality monitoring unit into a portable device has at least the following benefits:
  Increased usage through portability, utility (particularly when incorporated into a travel clock function) and availability;
  Allows keeping next to sleeping/family so that the detection range may be smaller and similarly, the alarm response may be less than a typical 85 decibels;
  The alarm mode is preferably an ascending volume mode;
  An activator may be provided on the unit to switch the unit on and off so that the detection facility may be switchable to conserve battery life during less risky periods; for example whilst the monitoring unit is packed in a suitcase or during daylight hours;
  It also allows selling at retail outlets for time pieces at points of travel; the number of these points of travel far exceed outlets for conventional detector devices which are not considered travel necessities but largely DIY (do it yourself) or home improvement products.

An air quality monitoring unit incorporates a sensor which may sense air quality by assessing the presence of one or more of the compounds selected from the group comprising: gas, carbon dioxide, carbon monoxide, smoke, methane, particulate pollution, ground-level ozone, sulphur oxides, nitrogen oxides, lead, hydro carbons, petrol vapour, ammonia, butane, hydrogen/acetylene, chlorine, ethylene oxide, hydrogen, hydrogen chloride, hydrogen cyanide, hydrogen sulphide, oxygen, ozone, sulphur dioxide, flammable gases, toxic gases, and any pollutants.

Advantageously, the air quality monitoring unit is an integral part of a portable/mobile device. The air quality monitoring unit may advantageously be an integral part of one at least of the articles selected from the group comprising: travel clocks, mobile phones, personal digital assistants (PDA), satellite navigational systems, torches (such as those used by fireman and rescue workers), portable breathing/medical devices (for example respirators etc) baby monitors, barometers, thermometers, doorbell chimes, dictation machines, diagnostic tools, attack alarms, power tools, travel irons, and calculators.

Integrated Fixed Devices

The air quality monitoring unit is particularly advantageous when incorporated in an article selected from the group comprising: clocks, barometers, thermometers, doorbell chimes, in a home, an office, a garage, a mobile home, a recreational home, vehicles, a bike, a boat, a car, a caravan, a truck, a car radio/information display system. The invention is particularly advantageous when the air quality monitoring unit is incorporated into road going vehicles when the sensor is selected to be for detecting the exposure to carbon monoxide, smog, or other pollutants which are present on modern streets. A bike would be particularly advantageous when incorporating a carbon monoxide/smog monitoring unit for displaying values of the sensed air quality. An aircraft system would also be particularly advantageous when incorporating as part of one of its information displays, a display of the exposure of carbon monoxide, smog, or other pollutants.

The air quality monitoring unit may also be incorporated within a conventional CO detector for enhancing the detector's functionality. The air quality monitoring unit may also be incorporated with in a home security system which provides the means to record, log and alert the user to the presence of gas.

The benefits of integrating an air quality monitoring unit into a fixed device include at least the following:
- Opportunity for hanging in prominent locations such as for example kitchen, entrance, bedroom, children's bedroom, offices, hotel room;
- Opportunity to present critical information to a user at a convenient level.

General Benefits

An air quality monitoring unit of the kind in question which comprises a sensor exposed to air, an activator for activating the unit, a controller, a communication channel for communicating signals representative of said sensed air quality from said sensor to said controller, and an alarm which is triggered by said controller dependent upon the signals received from said sensor has the following benefits:
- An increased option of detection units generally since they do not necessarily require mounting on a wall or connecting to the electrical mains supply;
- Increased user interaction/familiarity with the units; for example when incorporated in a clock, a user would constantly refer to the clock and to the sensed air quality reading which would therefore lead to a rapid response from a user even before a critical threshold is breached;
- Safer when deployed as a personal unit because of greater confidence in correct use, proper and regular testing and care;
- The air quality monitoring unit optionally incorporates both an indicator for air quality at an acceptable level or not;
- A carbon monoxide detector or other similar hazard detector which incorporates processing means adapted to tell the time, control the sounding of an alarm, allow the variation of a mode of operation, incorporate a calendar, organiser and a reminder system (for example to organise the annual boiler service or other activities);
- A processor or controller incorporating means for recording date and time of a test before setting the date and time for a subsequent test;
- Facilitates intelligent and measured responses. This is particularly important in the context of a carbon monoxide sensor incorporated into the air quality monitoring unit because unlike smoke, carbon monoxide can range from moderate to severe exposure and symptoms from chronic to acute. A few moments spent in a car garage during work daily is potentially in breach of the health and safety recommended levels. A defective flue for a gas appliance in breach of health and safety recommended levels but in a far shorter time scale;
- In an air quality environment where carbon monoxide is present at 50 parts per million, the air would be safe according to the United Kingdom's Health and Safety Executive;
- At a level of 200 parts per million or in certain circumstances at a level of 70 parts per million, an individual would develop a slight headache within 2 to 3 hours;
- In an environment of 400 parts per million, an individual would develop a frontal headache within 1 to 2 hours which would become wide spread in 3 hours;
- With an environment of air with 800 parts per million, an individual would develop dizziness, nausea, convulsions within 45 minutes and be entirely insensible in 2 hours;
- The processing means and/or the controller and/or the storage means of the air quality monitoring unit is or are configured to record the time the hazard having been detected; to record the measured changes over any given interval; and to compute the overall exposure time;
- Since 5 parts per million can be dangerous for infants and a level of 70 parts per million would necessitate immediate evacuation, the unit incorporates means for varying the sensitivity of the unit so that the threshold for a given alarm may be lowered or raised dependent upon the intended mode of use;
- The display portion of the unit may display exposure/evacuation time before serious bodily harm occurs; for example 2 hours or 20 minutes dependent upon the level detected; this function is achievable when both the hazard detection is recorded and the associated time during which the safety level has been breached;
- The unit operating by monitoring both time and hazard would allow rescue workers and/or military personnel to determine the appropriate management of a given situation;
- An indicator may be provided as part of a user interface on for example a clock; this may take the form of a graphical representation for displaying the threat level; this may be for example an exposure meter;
- The display may be of a graphical kind which is readily understood by individuals which may be poisoned and therefore in a confused state and therefore not necessarily simply a reading of a given level of parts per million;
- The unit controller may be employed to constantly change the readout in order to provide a user with a visual confirmation that the unit is functioning properly; the constantly changing readout feature is a far more accurate test measure because conventional test buttons in detector units only test the circuitry not the detector component itself;
- A user interface and appropriate processing means are envisaged to enable a user to set sex, weight, age, health for units to aid critical exposure/evacuation on time dependent upon the characteristics of an individual;
- This would allow criteria to be tailored to for example child's room; and to tailor the alarm mode to generate a more rapid response from the child as well as from his or her guardian;
- The air quality monitoring unit optionally incorporates a vocal alarm and a guidance system particularly tailored for certain age groups; this may take the form of 10 loud beeps and instruction such as "wake up. danger" or for example "please leave the room and get help quickly";
- The air quality monitoring unit optionally incorporates a vocal alarm; means for recording a personalised alarm; and means for sounding the alarm;

The air quality monitoring unit may optionally incorporate a remote loud speaker to raise an alarm outside of a room for example and a local loud speaker to raise an alarm inside the room; the alarm inside the room would preferably be tailored to the individual being detected; for example in the case of a child it ought to be intelligible for a child of as young as 2 to 3 years with some training;

The air quality monitoring unit optionally incorporates a switchable alarm between a full alarm and/or an ascending alarm; this would be particularly advantageous when employed in devices which are destined to be used in close proximity to a user when for example an immediate alarm blast at 85 decibels may not be sensible or desired; an alarm response, in line with the critical exposure countdown would be more sensible;

A vibrator may optionally be provided or a strobe guard which would be particularly useful for the hearing impaired;

The air quality monitoring unit advantageously incorporates a transmitter for transmitting an alarm signal wirelessly for example through Bluetooth technology;

The air quality monitoring unit in its portable form may be located on a bedside table and therefore may not be positioned in an optimal position for monitoring air quality; in this situation a holder which may be in the form of a telescopic arm or a flap which can foldout or swivel out in order to space the sensor away from the main portion of a unit is envisaged so that the main portion of the unit is located in close proximity to a user and the sensor is located in an optimum position for monitoring air quality;

It may enclose each of the components of the various aspects of this invention in a single housing with one or more recesses to allow it to be wall mounted on a single picture hook for enhanced detection;

Other releasable attachment means are envisaged such as a filamentary touch to close pad on the unit or a magnetic strip for attachment onto a fridge or other material suitable for magnetic attachment;

If the option of a recess is selected an A or W recess shaped recess is preferred which may be located at the centre of the back of a travel clock.

The unit may incorporate an auto protect function for night time operation; this may be provided by combining the detection unit with a time keeping device so that for example during a period defined as night time it would have extra sensitivity and/or a different response profile for example by employing a more rapidly ascending alarm volume than daytime operation.

The unit may incorporate means for being compatible with a wireless network; this would allow intelligent investigation of the hazard source, the communication of a recommended evacuation route, without a requirement for an external computer; the units could compute which detected a hazard first and then monitor spread patterns; a red LED could indicate immediate proximity to a hazard and an amber/green could indicate relative safety of an evacuation route; a master unit may be provided with increased memory;

It is also envisaged for the units to have one or more ports such as: USB, memory card, and other suitable medium for computation of data on a personal computer;

The unit may also be water proof or splash proof;

The units may also incorporate means to enhance the rate of which air is taken into the unit; such means may be for example a series or a single vent or pump located in the clock or other devices. The vents would preferably be located underneath the clock/devices;

The unit would incorporate processing means for event time stamping, which would facilitate triangulation of current threat, tracing of the source of threat, and determining fastest route to evacuate where multiple units are fitted (and/or networked);

Critical exposure countdown (for example: "two hours until exposure seriously hazardous", or "evacuate immediately");

Means for winding up the unit to charge a battery in order to avoid battery replacements;

The units in question can also incorporate a so-called "pack-me" function which is a travel packing assisting system which is fully described in an application filed by the same applicant on the same day as the present application; in its broadest sense the "pack-me" function comprises means for communicating a warning signal to a user which is specific to one or more articles to be packed; and a controller which during a period preceding a user's change of location triggers the communication of said signal to a user of said system in order to remind a user to pack said article.

Figure 14:
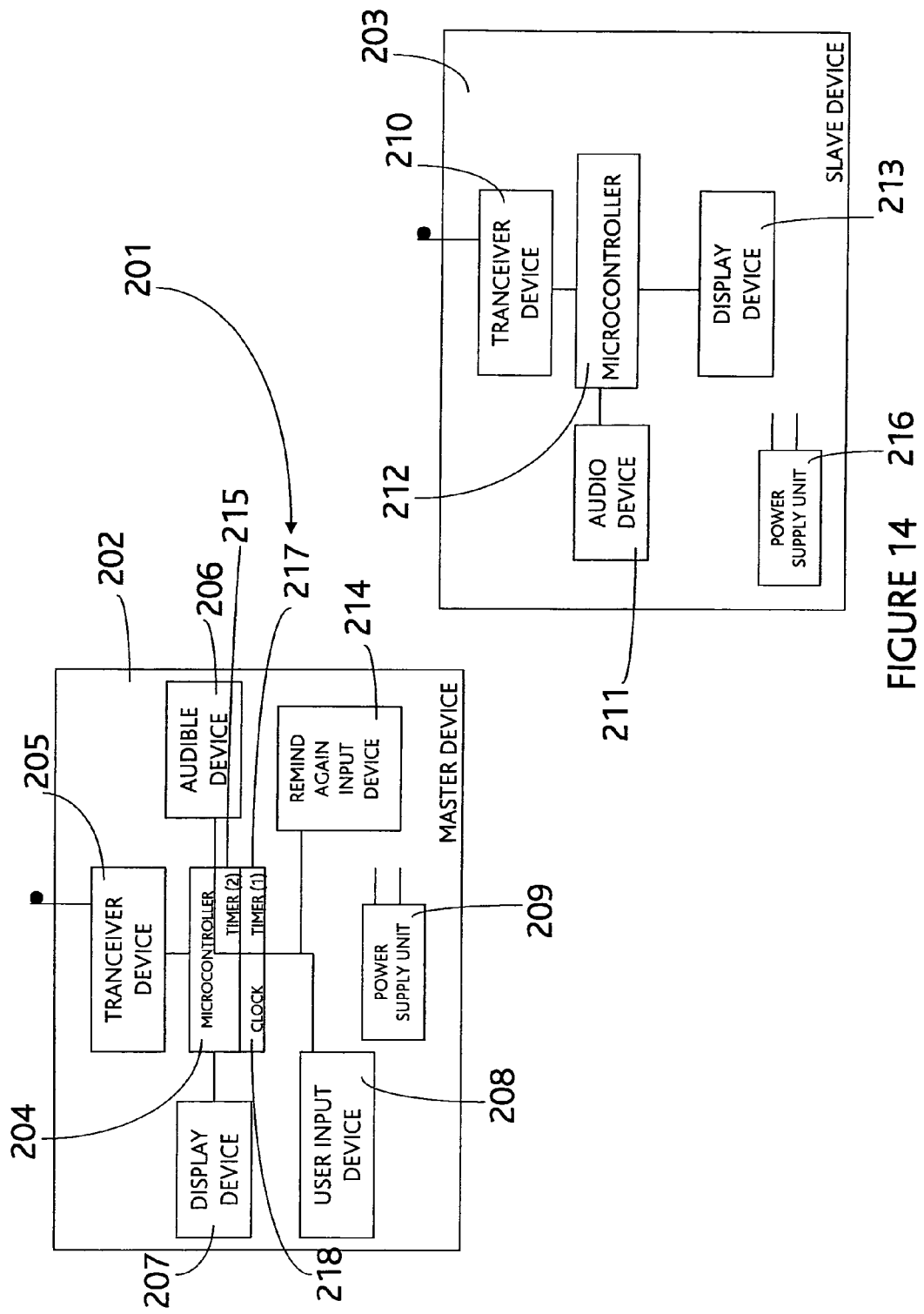
FIG. 14 shows a system block diagram representing the components of a master device incorporating the travel packing assisting system and an associated slave device.

FIG. 14 shows a system block diagram of a master device 202 and an associated slave device 203. Both devices are constituent components of an overall travel packing assisting system 201, which is also referred to as "Pack-Me". The master device 202 incorporates a microcontroller device 204, a transceiver device 205, an audible device 206, a display device 207, a user input device 208, a power supply unit 209. The slave device 203 incorporates a receiver device 210, an audio device 211, a microcontroller 212, a display device 213, a remind again input device 214 and a power supply unit 216.

The master device 202 is a portable device, which may be used or carried by the user when travelling. The portable device is typically one of the following types of devices: mobile phones, portable TV's, personal digital assistants (PDA's), laptops, game consoles, handheld toys, watches/clocks, music players, binoculars, camera's, camcorders, two-way radio's, portable DVD players, computer peripherals (Mice), MP4 players, headsets, portable navigational needs such as satellite navigation systems or GPS (global positioning systems), bike computers, golf computers, fitness watches, shavers, electric/electronic games, puzzles etc, electric instruments and keyboards. The associated slave device 203 is typically peripheral or secondary equipment dedicated to the master device 202. The associated device is typically one of the following devices: mobile phone chargers, portable device chargers, cables, power packs, antennas, cards (smart), accessories which have the risk of being overlooked and left behind in the room, after the user has packed and vacated the facility.

The microcontroller 204 is powered by the power supply unit 209. The power supply may also be the power supply of the master device 202 in which the Pack Me system is incorporated. The microcontroller 204 is connected to a display device 207, a transceiver device 205, an audible device 206, and a user input interface 208.

The master device 202 may automatically, or manually, detect if it is in a mode of travel by monitoring one or more sensory inputs. When the master device 202 has detected that it is in a mode of travel, the microcontroller 204 will call an "Enter Reminder" routine. The "Enter Reminder" routine prompts the device's user to enter the data attributes required to create a subsequent reminder event, via the display device 207. The data attributes may be in the form of:

Hotel Name;
Hotel Room;
Departure Date;
Departure Time;
Activation period (Pre-departure time);
Select Device;
Reminder Narrative.

The data attributes are entered via the user input device 208. For example, the device user will enter the following data attributes to ensure that he does not leave his mobile phone charger behind after vacating his hotel room:

Hotel Name=BABYLON;
Hotel Room=408;
Departure Date=Jul. 7, 2008;
Departure Time=09:00;
Activation period (Pre-departure time)=08:00;
Select Device=MOBILE PHONE CHARGER;
Reminder Narrative=DON'T FORGET MOBILE PHONE CHARGER.

The generated reminder event will be activated at 08:00 hrs, which is one hour, prior to the entered departure time of 09:00 hrs. The reminder event will activate the Pack-Me circuitry incorporated within the slave device 203, while concurrently displaying the reminder narrative to the device user via the display device 207, which in this case is to inform him not to forget his mobile charger. The logging of the hotel name and room number provides an accurate record of the user's accommodation, which may be retrieved at a later date. The reminder event is intended to for use with one or more selected devices and their associated narratives. The reminder event is also intended for use with multiple activation periods, for multiple devices, for an entered departure date and time.

Once the reminder event has been generated and logged within the master device 202, the microcontroller will continuously monitor the current date and time via the microprocessor's internal clock 218. The microcontroller 204 will compare all the reminder events with the current date and time to determine if a reminder event is due. If a reminder event is detected and activated, the microcontroller will call an "acknowledge slave devices" routine. The "acknowledge slave devices" routine will detect the presence of any slave devices within close proximity to the master device 202. The master device will ping all the slave devices, which are within the broadcasting range of transceiver 205. All slave devices receiving the ping signal will respond to the master device by transmitting a combined identification and status signal. The master device 202 will receive the response signals from the slave devices to determine if the relevant slave device is present. If the relevant slave device is present, the microcontroller will activate the Pack-Me circuitry incorporated within the slave device 203. Therefore alerting the user to the presence of the slave device and preventing it from being left behind when the user vacates the facility.

When the slave device 203 has been activated, the microcontroller 204 will start to decrement an internal timer (1) 217, which has been initially set with a value, which equates to the active period initially set by the user. The slave device 203 is active only while the timer (1) 217 is decrementing this value. When the timer value is decremented to zero, the microcontroller 204 will then initiate audio and visual warnings to the user via the display device 207 and audio device 206, therefore increasing the intensity of attracting the user's attention. The master device 202 has a "Remind Again" Function which when activated, resets the timer back to its initial value and initiates a second timer (2) 215 that counts down automatically. Once the second timer (2) 215 has decremented to zero (timed out) the microcontroller 4 will then initiate the decrementing of timer (1) 217. Timer (2) 215 is a type of snooze timer which will allow a set period of time (which may be entered by the user) to expire before reinitiating the reminder event. The "Remind Again" Function is intended to be similar to the conventional "snooze" function of an alarm clock.

The master device has an "alarm cancel" function, which deactivates the reminder event by deactivating the Pack-Me circuitry embedded within the slave device 203.

A typical application for the Pack-Me system is a mobile phone (master device) and its associated battery charger (slave device), which is required for charging the mobile phone. A mobile phone, which incorporates a Pack-Me system, will activate the alarm devices within the mobile phone's associated battery charger, at a predetermined time interval before the user is due to checking out of a hotel. The activation of the slave devices will attract the user's attention, therefore preventing the slave devices from being left behind by the user. In a further example of a typical application for the Pack-Me system is a mobile phone (master device) and an associated safety device such as Carbon Monoxide (CO) detector (slave device), which is required by the user to monitor CO levels within the room. The Pack-Me system prevents a safety conscious user from accidentally leaving behind the Carbon Monoxide detector. In a further example of a typical application for the Pack-Me system is a laptop, which incorporates the Pack Me system that communicates with associated devices such as a battery charger, a mouse, a printer, and a mouse mat upon the user's departure.

In another further example of a typical application of the Pack-Me system, the system devices are incorporated with a "paging" functionality. The "paging" function requires each of the slave devices to be incorporated with a self contained power supply. Typically in the form a battery or rechargeable battery, which enables the slave devices to remain powered, to ensure that they receive a page/wake up signal originating from the master device. For example, a mobile phone incorporating the Pack-Me function, combined with an additional paging function, which when activated will locate its associated mobile charging device (slave device). If the mobile charging device incorporates a rechargeable battery, the battery may be recharged when the charging device is connected to the mains electricity supply. The master device may be in the form of another device such as a laptop computer, which will enable the user to select a slave device from a number slave devices and page it to discover its physical location.

The system devices may also be incorporated with a paging function which exist in isolation from the Pack-Me system. Therefore, a TV manufacturer may not require the Pack-Me features, but may wish to incorporate a dedicated "paging" feature between the TV and its associated remote control device.

Figure 15:
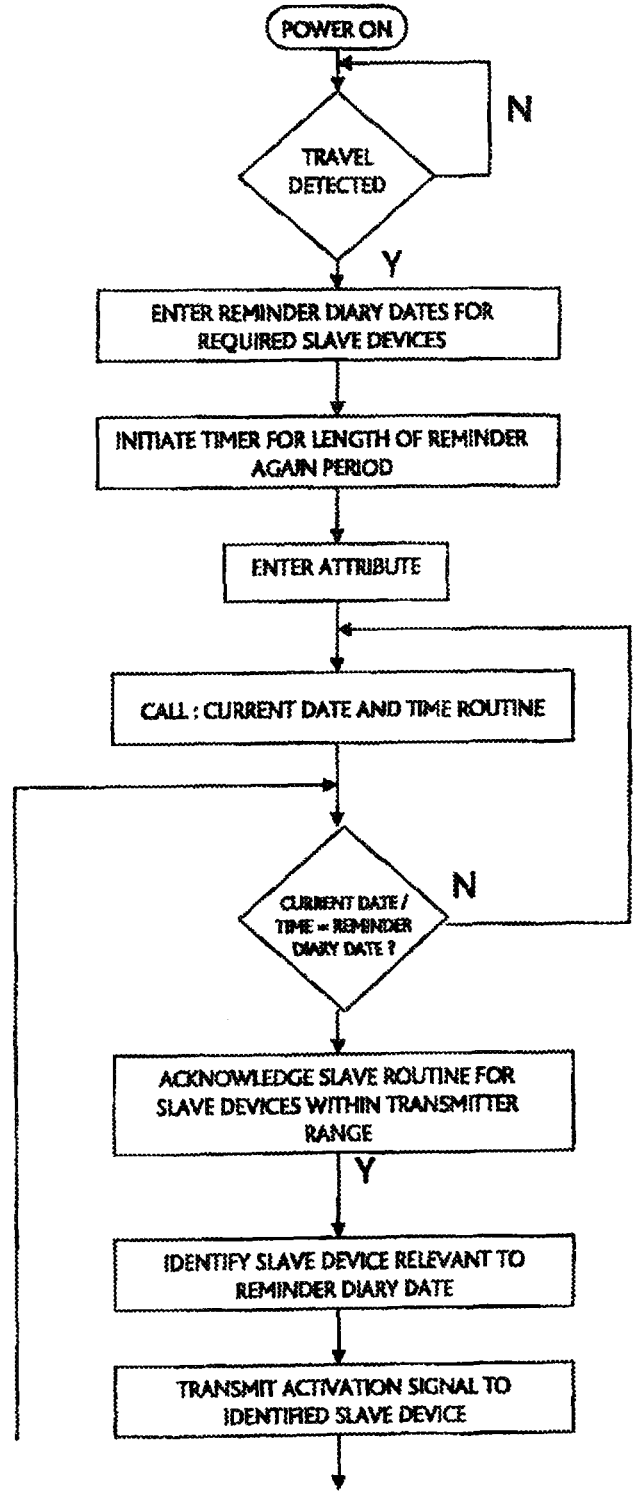
FIGS. 15A and B shows a flow diagram representing the functionality of the master device incorporating the travel packing system.
Figure 15B:
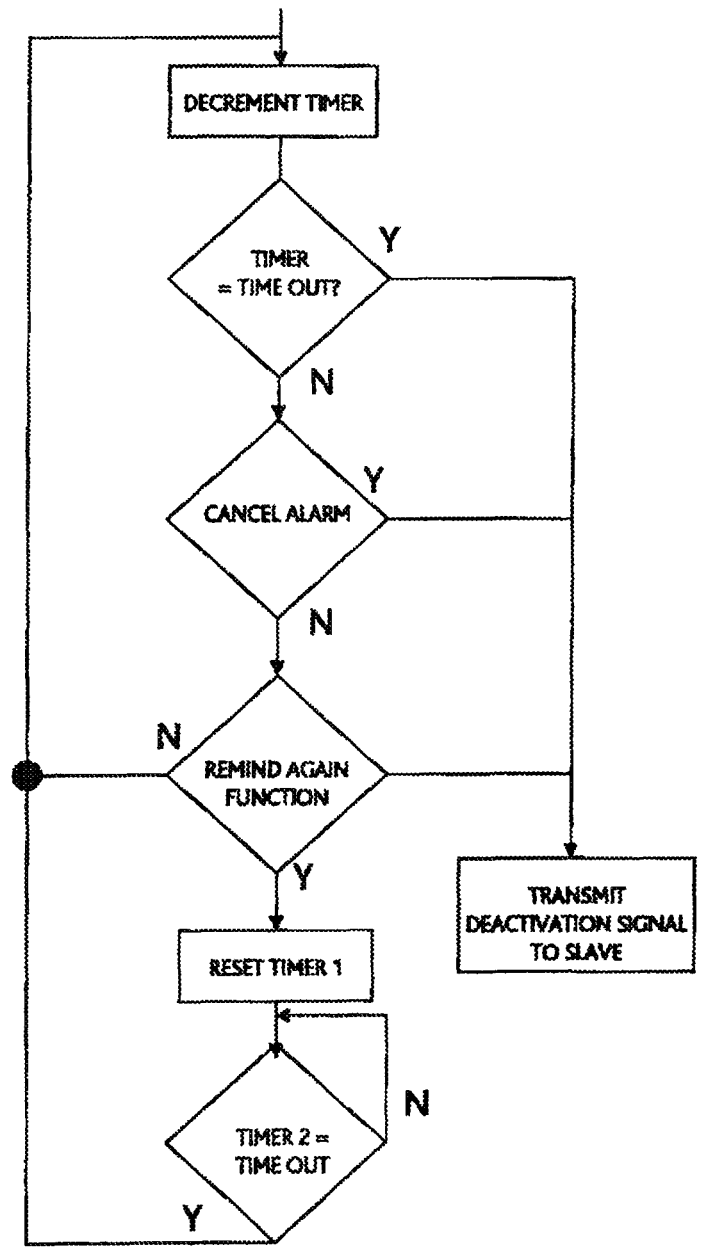

FIGS. 15A and 15B shows a functional diagram for the master device embodiment shown in FIG. 14.

Figure 16:
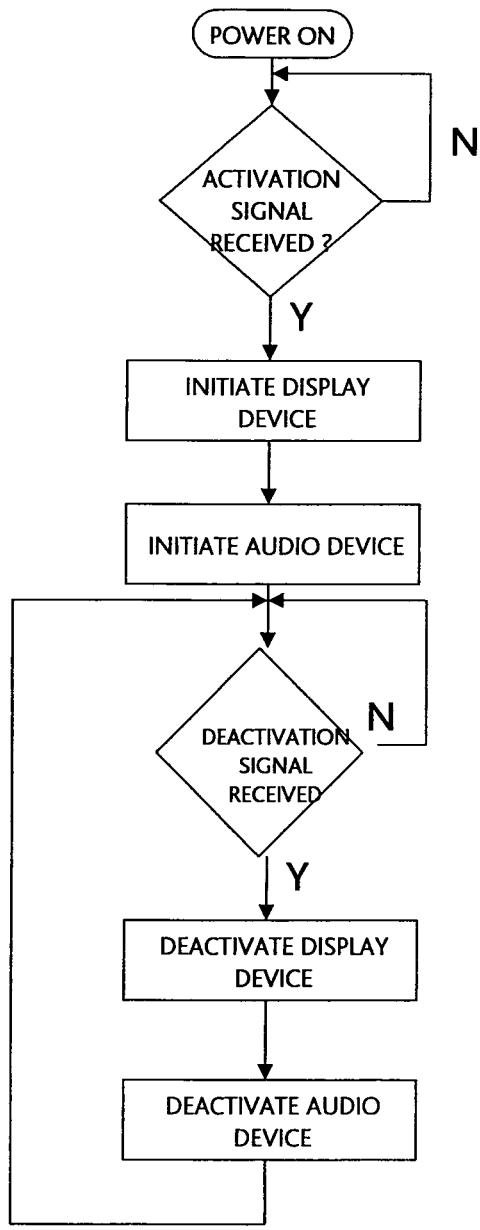
FIG. 16 shows a flow diagram representing the functionality of the associated slave device incorporating the travel packing system.

FIG. 16 shows a functional diagram for the slave device embodiment shown in FIG. 14.

Figure 17:
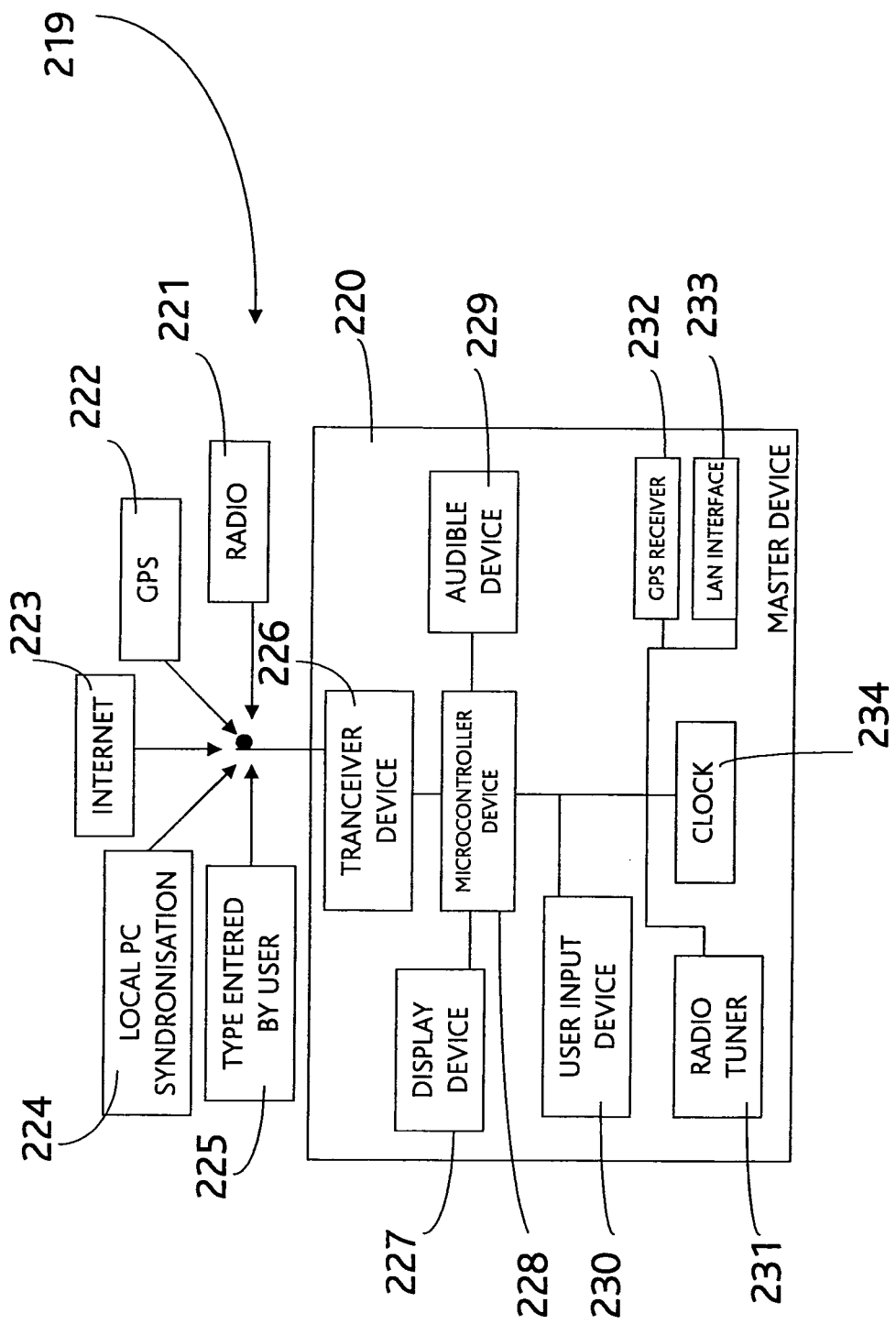
FIG. 17 shows a system block diagram representing the components of a device, which are triggered by monitoring local time.

FIG. 17 shows an alternative embodiment of the Pack-Me system 219, a user input device 230, a radio tuner 231, a GPS receiver 232, a LAN interface 233, and an internal clock 234.

The radio tuner 231 is a component, which extracts the time data embedded within a radio signal 221 that is typically broadcasted from a commercial radio station. The radio station broadcasts the time in both audible and machine-readable time code form which can be used as references for radio clocks and radio controlled watches.

The Global Positioning System (GPS) receiver 232 is a component, which extracts the time data embedded within a satellite signal. Most clocks are synchronised to coordinated universal time (UTC), the atomic clocks incorporated within satellites are set to GPS time. The difference between the two systems is that GPS time is not corrected to match the rotation of the earth; therefore it does not contain leap seconds or any other corrections, which are periodically added to the UTC. GPS time was set to match coordinated universal time UTC in 1980, but has since diverged. The lack of corrections means that GPS time remains at a constant offset (19 seconds) with the International atomic time (TAI). Periodic time corrections are performed on the satellite onboard clocks to correct relativistic effects and keep them synchronised with ground clocks. The GPS navigation message includes a difference between the GPS time and the UTC, which as of 2006 is 14 seconds, due to the leap year, added to the UTC on Dec. 31, 2005. Receivers subtract this offset from GPS time to calculate UTC and specific times and values. New GPS units may not show the correct UTC time until after receiving the UTC offset message. The GPS/UTC offset field can accommodate 255 Leap seconds (8 bits), which out of the current rate of change of the earth's rotation, which is sufficient to last until the year 2330.

The LAN interface 233 is a component that extracts the time signal from a PC local area network (LAN) configuration, therefore enabling the master device 220 to be synchronised to a local PC network.

The microcontroller 228 wilt call a "Get time" routine, which enables the master device 220 to obtain the local time. The local time value may be extracted from a number of time sources, such as local radio networks 221, GPS satellite network 222, the Internet 223, synchronisation from a PC LAN 224, or a manually entered time value 225 via the user input device 230. Once the local time has been obtained, it is then compared against the last known time value stored within the microcontroller 228. If the two time values are not identical it may be due to the master device 220 being located within a new time zone. This will action will cause the microcontroller 228 to detect that it is in a mode of travel and will activate the Pack-Me system.

Figure 18:
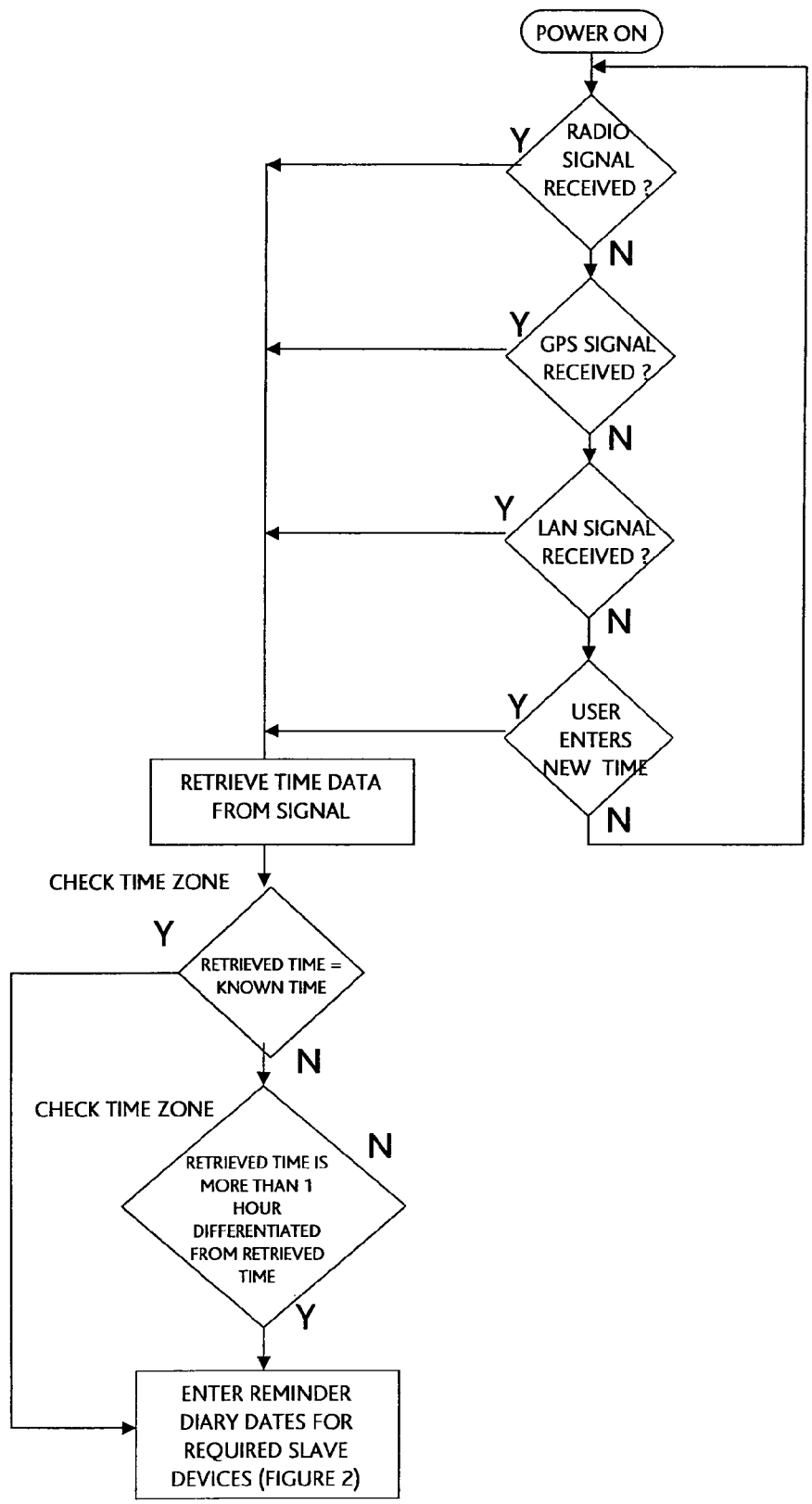
FIG. 18 shows a flow diagram representing the functionality of a device, which is triggered by monitoring the local time.

FIG. 18 shows a functional diagram of the embodiment shown in FIG. 17, which represents the travel detected decision block shown in FIGS. 15A and 15B.

Figure 19:
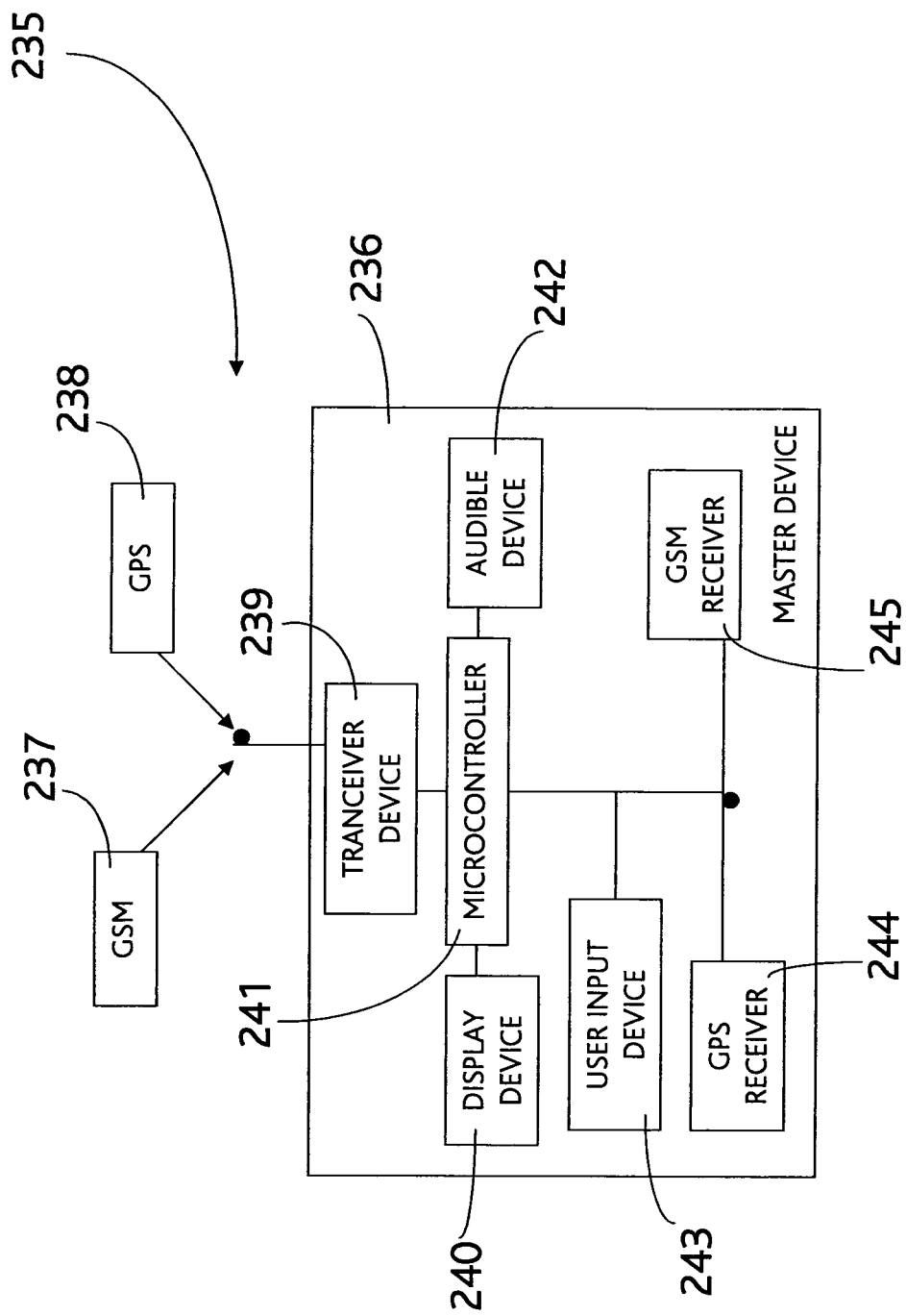
FIG. 19 shows a system block diagram representing the components of a device, which are triggered by monitoring its physical location.

FIG. 19 shows an alternative embodiment of the Pack-Me system 235, which includes a master device 236, which is shown to be in communication with a mobile network (GSM) 237 and/or a satellite network (GPS) 238 to determine the master device's geographic location. The master device 236 incorporates a transceiver device 239, a display device 240, a microcontroller 241, an audible device 242, a user input device 243, a GPS receiver 244 and a GSM receiver 245.

The GPS receiver 244 is a component that calculates its actual position by carefully timing the signal sent via the constellation of GPS satellites, which orbit the earth. Each satellite continually transmits messages containing the time the message was sent, a precise orbit for the satellite sending the message (the ephemeris) and the general system health and rough orbits for all the GPS satellites (the almanac). The GPS receiver uses the arrival time of each message to measure the distance to each satellite, from which it determines the position of the receiver using geometry and trigonometry (trilateration). The resulting coordinates are converted to more user-friendly forms of data such as latitude and longitude, or a location on a map and then displayed to the user. Three satellites are required to solve a position, as space has three dimensions. However, a three satellite solution requires a time to be known to a nanosecond or so, far better than any non-laboratory clock can provide. Using four or more satellites allows the receiver to solve the time as well as geographic position, eliminating the need for a super accurate clock.

The GSM receiver 245 is a component, which uses multi-lateration to determine the location of GSM mobile phones, usually with the intent to locate the user. There are three types of GSM localisation; these are network types, handset types and hybrid types, which are a blend of the two previous types. Network based techniques utilise the service provider's network structure to identify the location of the handset. The advantage of the network-based techniques is that they can be implemented non-intrusively, without affecting the handsets. The accuracy of network-based techniques varies, with cell identification as the least accurate and triangulation as the most accurate. The accuracy of network-based techniques is closely dependant upon the concentration of base station cells, with urban environments, which can achieve the highest possible accuracy. Handset-based technology requires the installation of client software on the handset to determine its location. This technique determines the location of the handset by computing its location by cell identification, signal strengths of the home and neighbouring cells or latitude and longitude, if the handset is equipped with a GPS module. The calculated location is then sent from the handset to a location server. The key disadvantage of this technique is a necessity of installing software on the handset. It requires active cooperation of the mobile subscriber as well as software that must be able to handle the different operating systems of the handsets. Typically only a smart phone such as ones based upon mobile operating systems such as Symbian's Epoch™ and Microsoft's Windows Mobile™, will be able to run such software. Hybrid-based techniques use a combination of network-based and handset-based technologies for location determination. One example will be assisted-GPS, which uses both GPS and network information to compute the location. Hybrid-based techniques give the best accuracy of the three forms of localisation, but inherit the limitations and challenges of network-based and handset-based technologies.

The microcontroller 241 extracts the data representing the physical location of the master device 236 from a mobile network (GSM) 237 and/or a satellite network (GPS) 238. The microcontroller 241 will call up a "get position" routine, which extracts the positional data from the connected networks and compares this data with the last known positional data of the master device 236. If the obtained positional data has a value, which is different from the microcontroller's previously stored positional date; the microcontroller 241 will determine the master device is in a state of travel and will activate the Pack-Me system.

Figure 20:
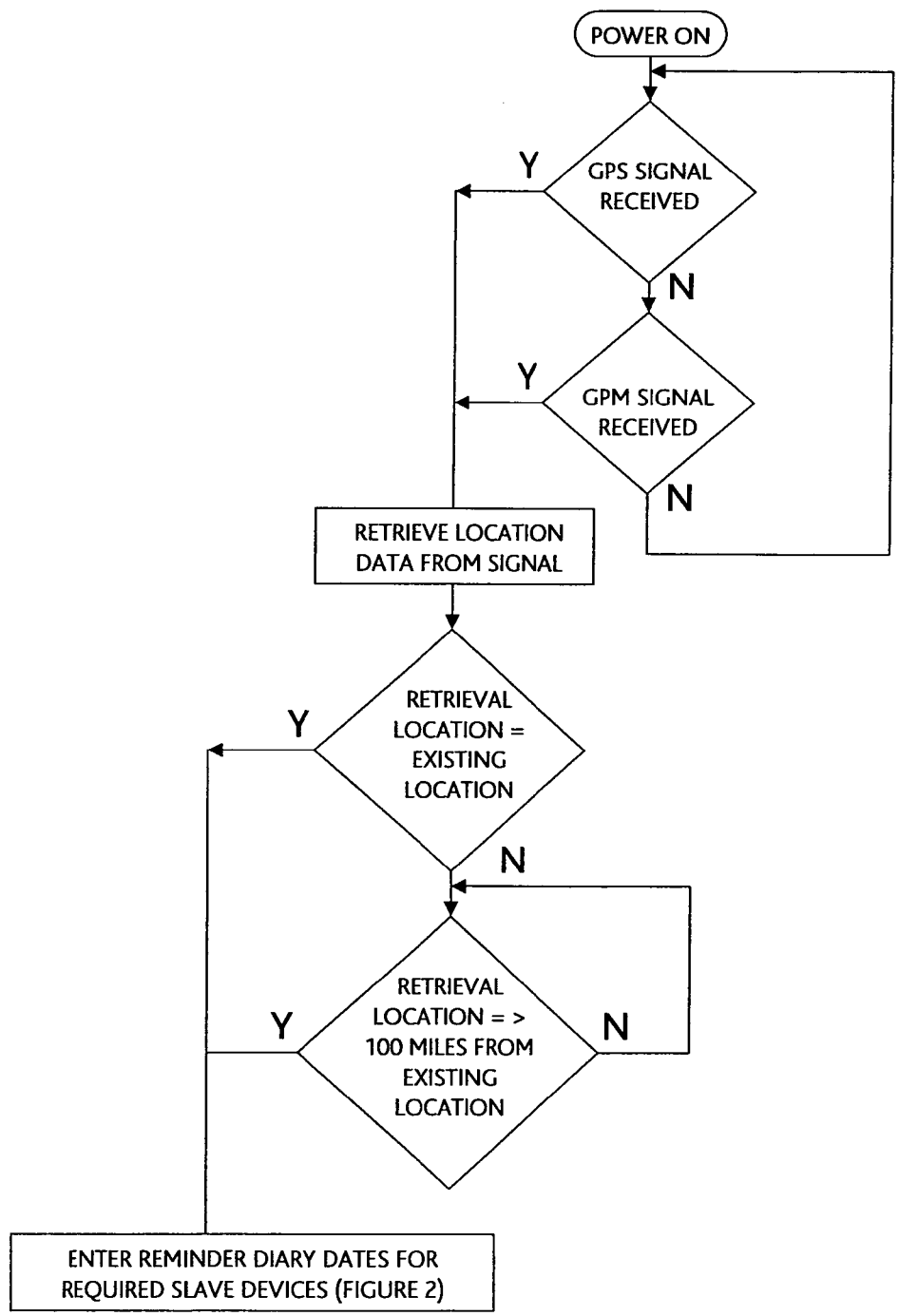
FIG. 20 shows a flow diagram representing the functionality of a device, which is triggered by monitoring its physical location.

FIG. 20 shows a functional diagram for the embodiment shown in FIG. 19, which represents the travel detected decision block shown in FIGS. 15A and 15B.

Figure 21:
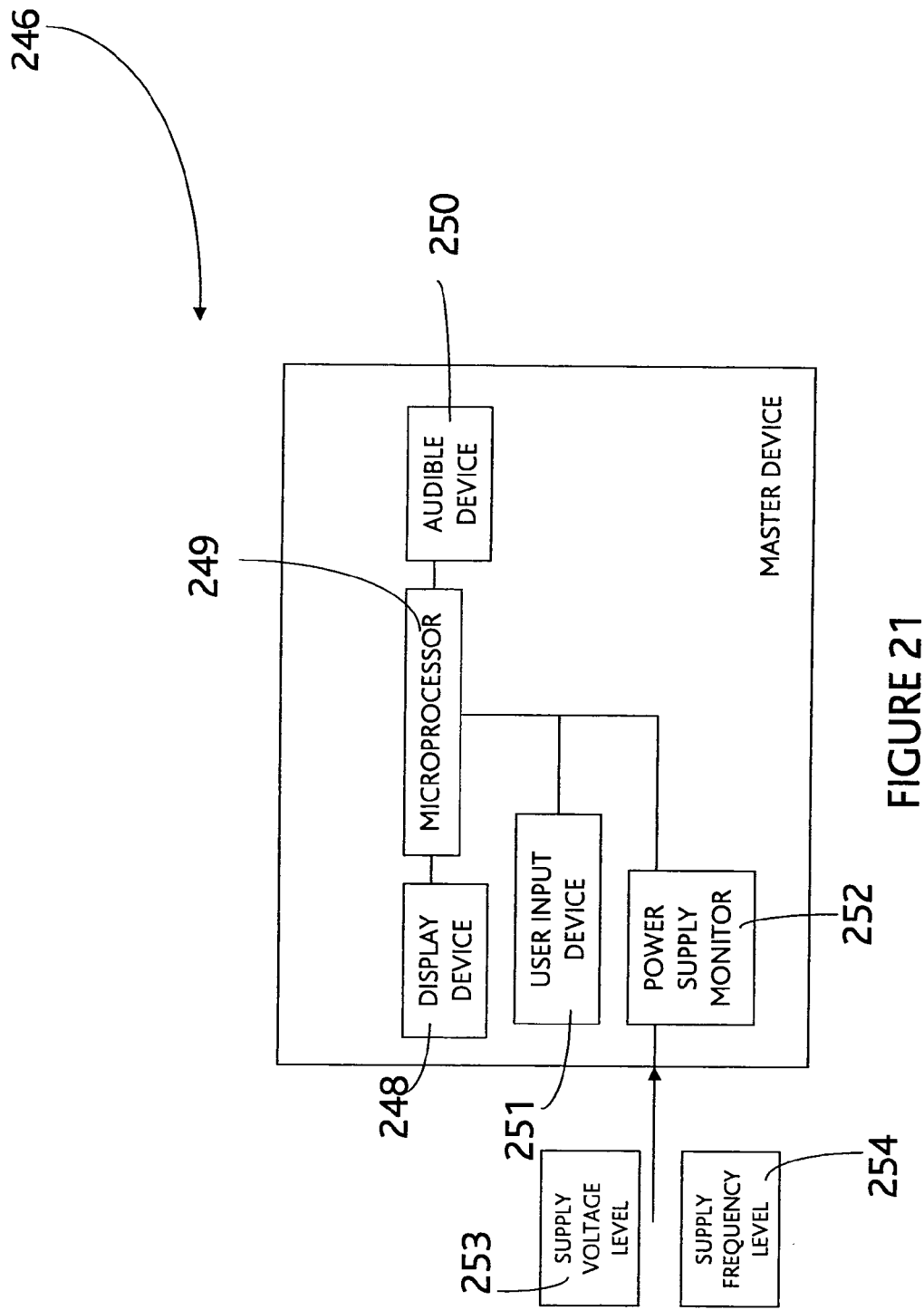
FIG. 21 shows a system block diagram representing the components of a device, which are triggered by monitoring the mains voltage supply.

FIG. 21 shows an alternative embodiment of the Pack-Me system 246, which detects if the device is in a travel mode by monitoring the mains voltage supply. The monitoring of the mains supply voltage incorporates monitoring of the mains voltage level and mains voltage frequency. The master device 246 incorporates a display device 248, a microcontroller 249 an audible device 250, a user input device 251 and a power supply monitor 252.

The power supply monitor 252 is a component which monitors the mains electricity supply to determine if the master device has changed location. A number of states have differing supply voltages and supply frequencies, which are distinctive from another state.

The microcontroller 249 within the master device 246 will store data which represents the mains voltage level and mains frequency when the master device 246 is connected to a mains electricity supply. The microcontroller 249 will determine that it is in a state of travel, if the data for the supply voltage level and supply frequency is different from the data acquired when the master device 246 was previously connected to a mains electricity supply. The microcontroller 249 will initiate the Pack-Me system if it determines a state of travel. The voltage levels are generally in the range of 100 to 240 volts (always expressed as the route–mean–voltage). The supply voltage frequency is normally either 50 Hz or 60 Hz. For example, the UK uses a mains supply voltage level of 230 volts, at a frequency of 50 Hz. Therefore, if the mains electrical supply monitored, has a large differential from this known voltage level and frequency, it could be used as a means of detecting a mains electrical supply of another state. If the microcontroller determines a large differential between the actual mains electrical supply being monitored and the known values for a given voltage level and frequency, it will determine that it is in a state of travel and will activate the Pack-Me system.

Figure 22:
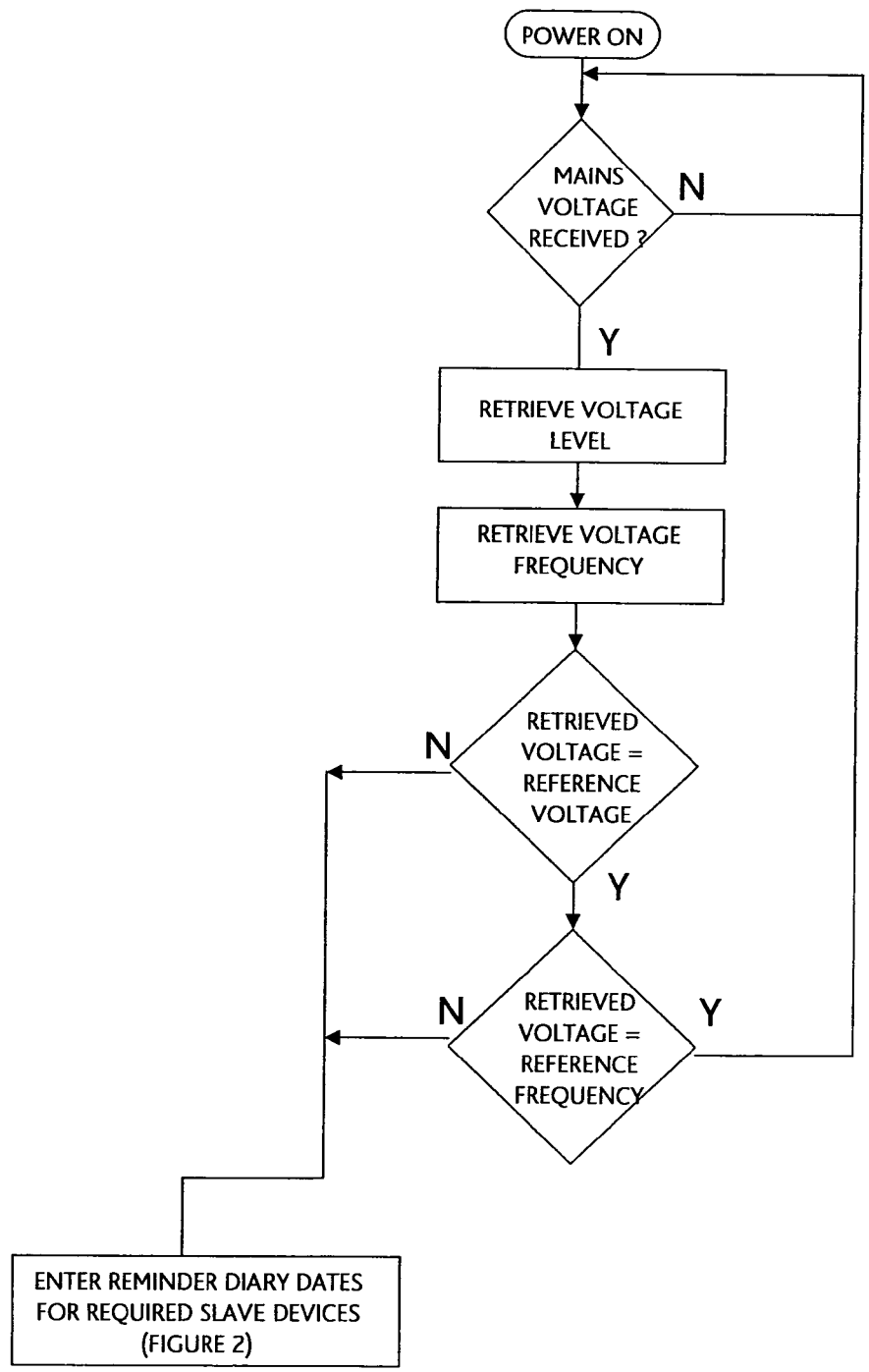
FIG. 22 shows a flow diagram representing the functionality of a device, which is triggered by monitoring the mains voltage supply.

FIG. 22 shows a functional diagram for the embodiment shown in FIG. 21, which represents the travel detected decision block shown in FIGS. 15A and 15B.

Figure 23:
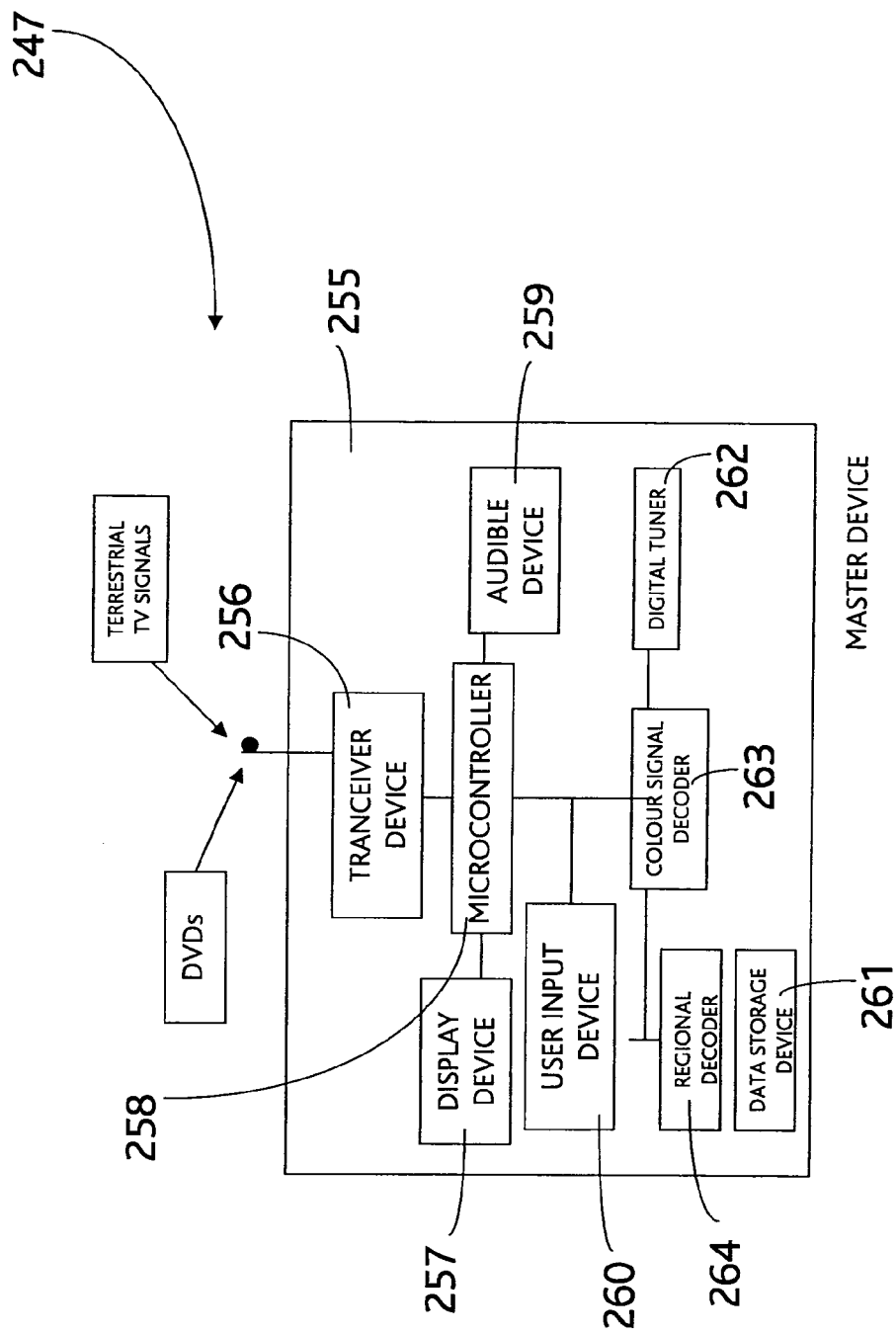
FIG. 23 shows a system block diagram representing the components of a device, which are triggered by monitoring the regional data embedded within multimedia.

FIG. 23 shows an alternative embodiment of the Pack-Me system 247, which includes a master device 255, which determines a travel mode by retrieving the regional colour encoding signal originating from data storage devices such as Digital Versatile Disk (DVD) or Terrestrial TV signals. The master device 255 incorporates a transceiver device 256, a display device 257, a microcontroller 258, an audible device 259, a user input device 260, a data storage device decoder 261, a TV tuner decoder 262, a colour signal decoder 263 and regional decoder 264.

The colour signal decoder 263 is a component which decodes the colour signal embedded within a TV signal. There are three main types of colour encoding systems which are, Phase Alternating Line (PAL), National Television System Committee (NTSC) and séquentiel couleur á mémoire (SECAM). More than 120 countries and territories use or have used the terrestrial PAL colour encoding system, the UK being one of those countries. More than 61 countries are using or have used NTSC colour encoding system. The most popular areas for using this system are North America, Central America and the Caribbean, South America, ASIA and US territories and Pacific Island Nations, the main user being the United States. More than 60 countries are using or have used SECAM colour encoding system for broadcasting their national television broadcasting system. The most popular areas for using this system are Africa, ASIA, Pacific Islands, Europe (mainly France), former USSR and the Americas. The colour signal decoder 263 decodes the colour signal embedded within the television signal. The decoded information is then communicated to the microcontroller 258, which then determines the type of the colour encoding signal embedded within the television signal.

If the microcontroller 258 determines that the colour encoded signal data is different from the data of a known signal, the microcontroller 258 will determine that it is in a state of travel and the master device 255 is physically located within a television network of another state. The microcontroller 258 will then activate the Pack-Me system.

The data storage device 261 would typically be an optical storage device such as a DVD, or any other newer innovations, i.e. "Blue-ray" discs. All pre-recorded DVD's incorporate an embedded regional code, which restricts the DVD to a geographic area within the world where they can be played. DVD discs without a regional code are known as all region 0 discs. The commercial DVD player specification requires that a player to be sold in a given place does not play discs encoded for a different region (region 0 discs are not restricted). This is mainly for the purpose to allow motion picture studios to control aspects of a release including content release date and especially price of a file according to a region. There are 10 regional codes, these range from 0 to ALL, these are defined as:

Regional code 0: informal term meaning (worldwide), region 0 is not an official setting; discs that bear the region 0 symbol have either no flag set or have region 1-6 flags set;

Regional code 1:—Canada, United States, US territories and Bermuda;

Regional code 2:—Europe, Western Asia, Kingdom of the Netherlands, Egypt, Japan, Lesotho, South Africa, Swaziland, British overseas territories, French overseas territories, Greenland and United Kingdom;

Regional code 3:—South East Asia, South Korea, Hong Kong, Macau and Taiwan;

Regional code 4:—Oceania, Central and South America, Caribbean and Mexico;

Regional code 5:—Africa, Central and South Asia, Bellerose, Mongolia, North Korea and Ukraine;

Regional code 6:—Main land China;

Regional code 7:—reserved for future use (found in use on protected screener copies of MPAA-related DVDs and "media copies" of press releases in ASIA);

Regional code 8:—International venues such as aircraft, cruise ships etc;

Regional code ALL:—regional ALL discs have 8 flags set, allowing a disc to be played in any local on any player within the world.

The data storage device 261 communicates stored data to the regional decoder device 264. The regional decoder device 264 extracts a regional code from the received data and communicates the regional code data to the microcontroller 258. If the microcontroller 258 determines that the regional code data is different from data of a known regional code, the microcontroller 258 will determine that it is in a state of travel and the master device 255 is physically located with another regional code jurisdiction. The microcontroller 258 will then activate the Pack-Me system.

Figure 24:
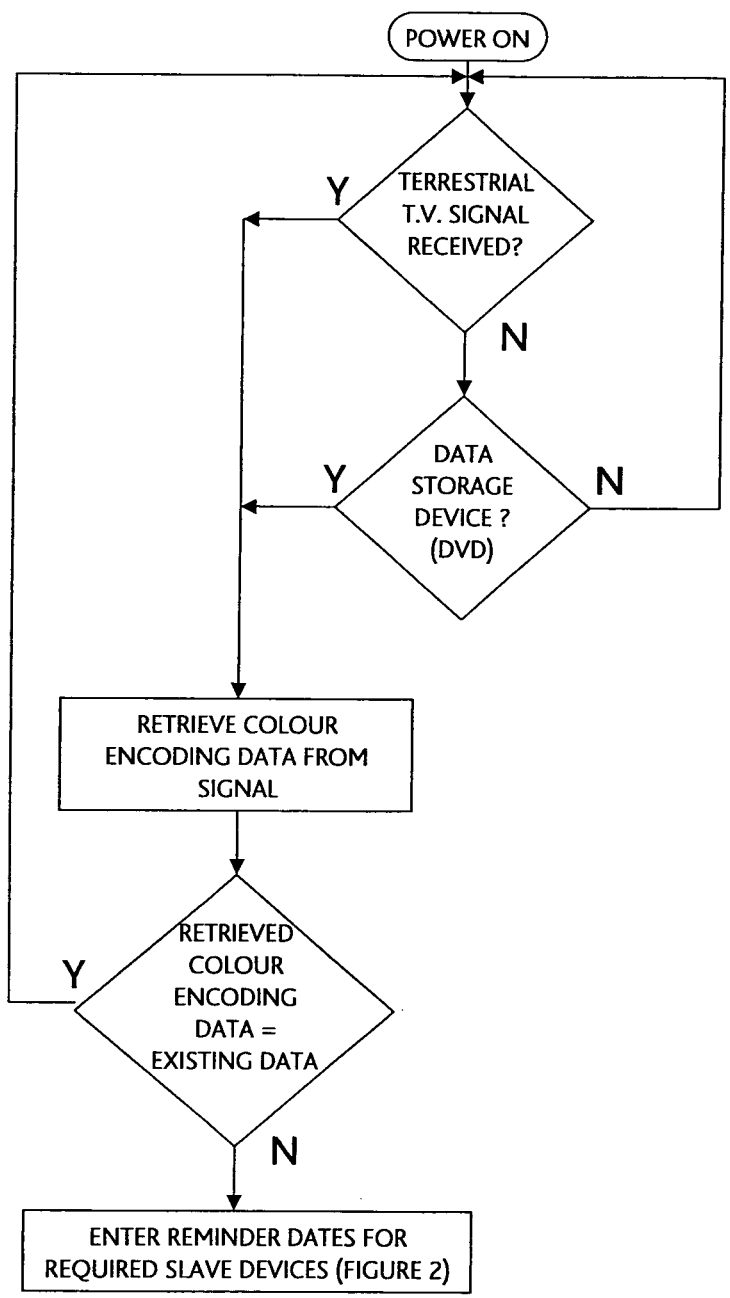
FIG. 24 shows a flow diagram representing the functionality of a device, which is triggered by monitoring the regional data embedded within multimedia.

FIG. 24 shows a functional diagram for the embodiment shown in FIG. 23, which represents the travel detected decision block shown in FIGS. 15A and 15B.

Figure 25:
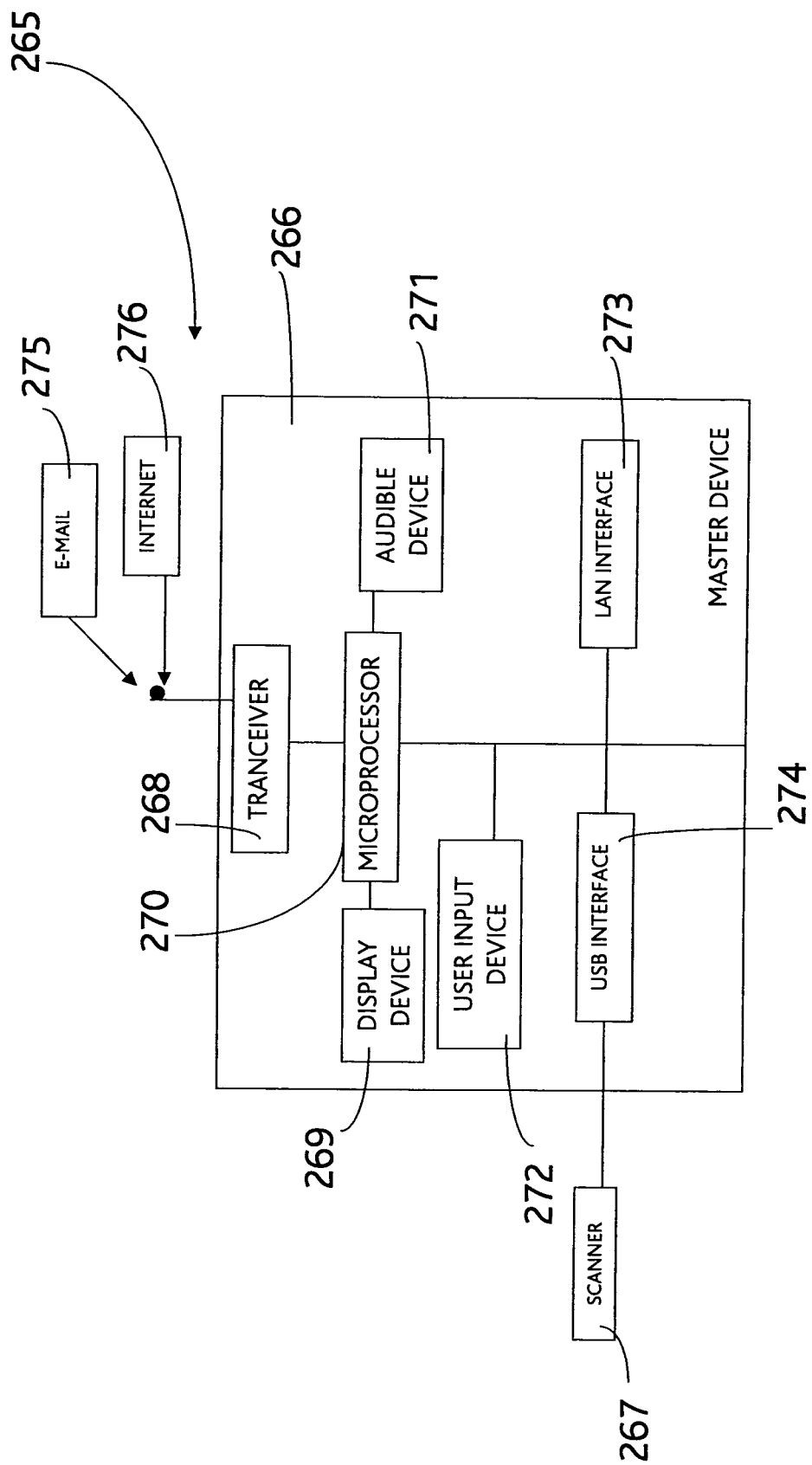
FIG. 25 shows a system block diagram representing the components of a device, which are triggered by monitoring textual representations.

FIG. 25 shows an alternative embodiment of the Pack-Me system 265, which includes a master device 266, which determines a travel mode by analysing the text of a document via a scanner device 267, an email 268, the contents of a webpage on the Internet 269. The master device 266 incorporates a transceiver device 268, a display device 269, a microcontroller 270, an audible device 271, a user input device 272, a LAN interface 273, and a universal serial bus (USB) interface 274.

The scanner device 267 is a component which optically scans images, printed text, handwriting or an object and converts it to a digital image. Typical examples are desktop (flatbed) scanner where the document is placed on a glass window for scanning. Hand held scanners where the device is moved by hand and mechanically driven scanners that move the document are typically used for large-format documents, where the flatbed design would be impractical. Modern scanners use a charge coupled device (CCD) or a contact image sensor (CIS) as the image sensor. A rotary scanner used for high-speed document scanning is a type of drum scanner, using a CCD array instead of a photomultiplier. Other types of scanners are planetary scanners, which rake photographs of books and documents and 3D scanners for producing three-dimensional models of objects.

The universal serial bus (USB) interface 274 is a component which drives a serial data bus to other interface devices. The USB was designed to allow many peripherals to be connected using a single standardised interface socket and improve the plug and play capabilities by allowing devices to be connected and disconnected without rebooting the computer (known as hot swapping). Other USB features include providing power to low-consumption devices without the need for an external power supply and allowing many devices to be used without requiring manufacturer specific device drivers to be installed.

The Scanner device 267 will convert the text within a document in to a digital image. The digital image data will then be communicated to the master device 266 via the USB interface device 272, which in turn communicates the digital data to the microcontroller 270. The microcontroller 270 will then compare the acquired digital data from the scanner with known data which represents other languages. If the two types of data do not compare, the microcontroller 270 will then determine that it is in a state of travel. The microcontroller 270 will then activate the Pack-Me system.

Figure 26:
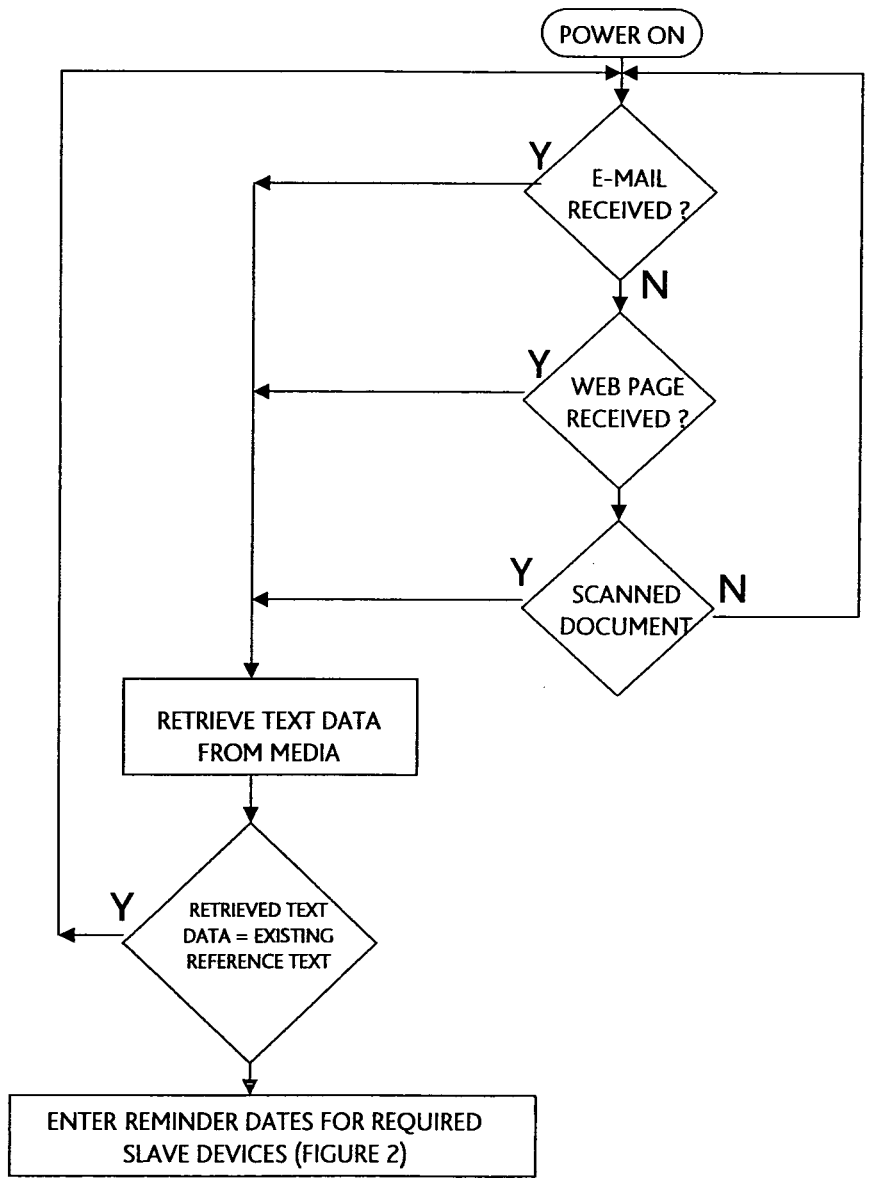
FIG. 26 shows a flow diagram representing the functionality of a device, which is triggered by monitoring textual representations.

FIG. 26 shows a functional diagram for the embodiments shown in FIG. 25, which represents the travel detected decision block shown in FIGS. 15A and 15B.

Figure 27:
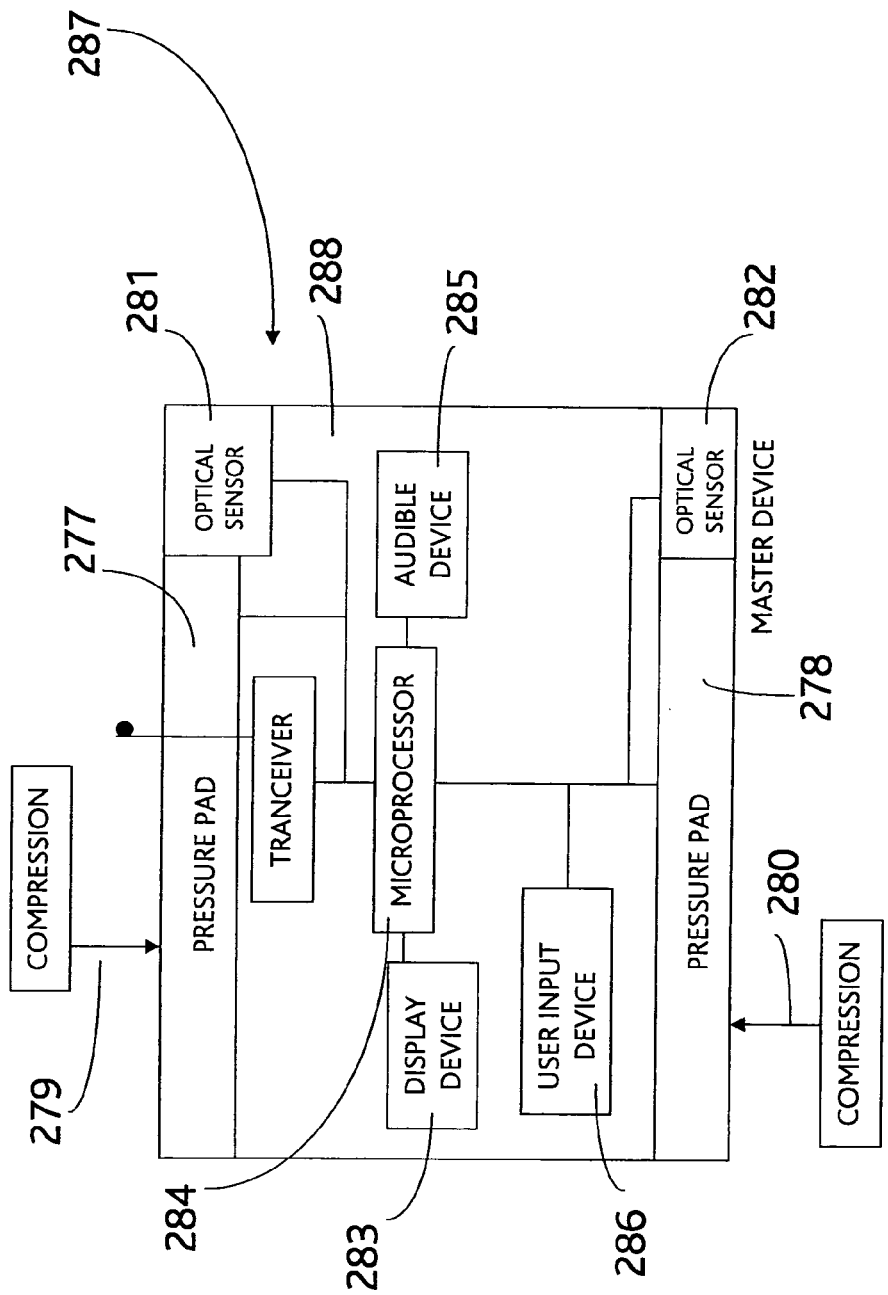
FIG. 27 shows a system block diagram representing the components of a device, which are triggered by monitoring its surrounding environment.

FIG. 27 shows an alternative embodiment of the Pack-Me system 287, which includes a master device 288, determines if it is in a travel mode by detecting pressure upon the master devices outer surface via pressure pads 277 and 278 The pressure pads 277 and 278 communicate the pressure pad data to microcontroller 284. The external pressure onto the master device is indicated by arrows 279 and 280. The pressure pads 277 and 278 detect the outer pressure applied to the master devices outer surface as a way of determining a state of travel. The applied pressure is indicative of the master device 288 being packed within a suitcase or another luggage item. The master device 288 also incorporates two optical sensors 281 and 282, which detect the presence of tight (or the lack of light) upon the master device's outer surface. The microcontroller 284 receives the illumination data communicated from optical sensors 281 and 282 to determine whether or not the master device has been packed within a suitcase and/or other luggage item. If the microcontroller 284 receives data which represents no light on the master devices outer surface, it will determine that it is a state of travel. The microcontroller 284 will then activate the Pack-Me system. The master device 276 also incorporates a display device 283, a microprocessor 284, an audible device 285 and a user input device 286.

Figure 28:
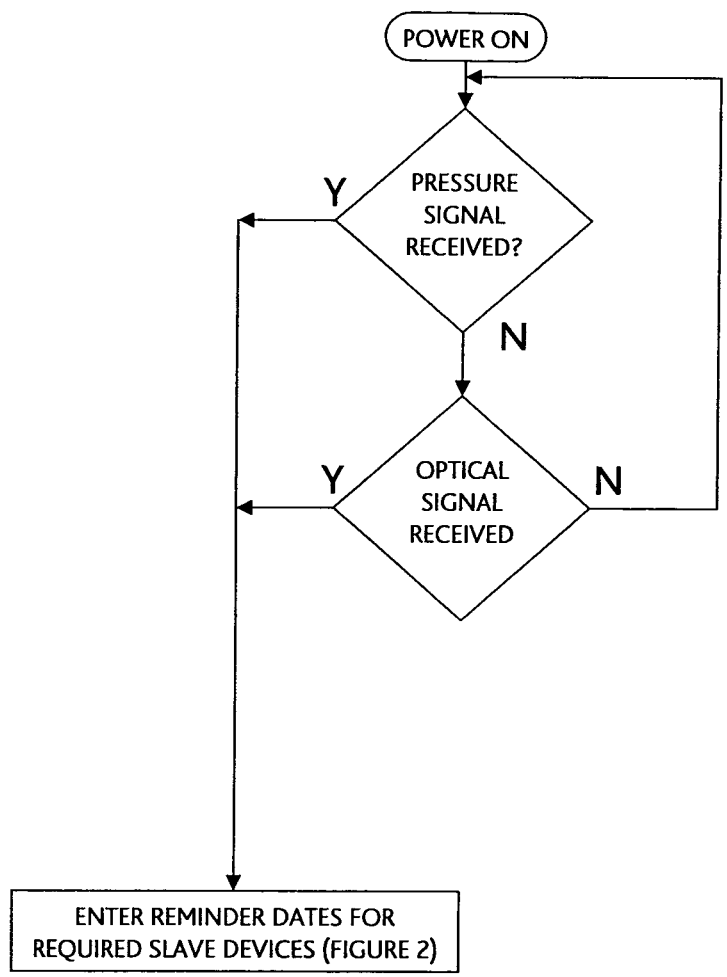
FIG. 28 shows a flow diagram representing the functionality of a device, which is triggered by monitoring its surrounding environment.

FIG. 28 shows a functional diagram for the embodiments shown in FIG. 27, which represents the travel detected decision block shown in FIGS. 15A and 15B.

Figure 29:
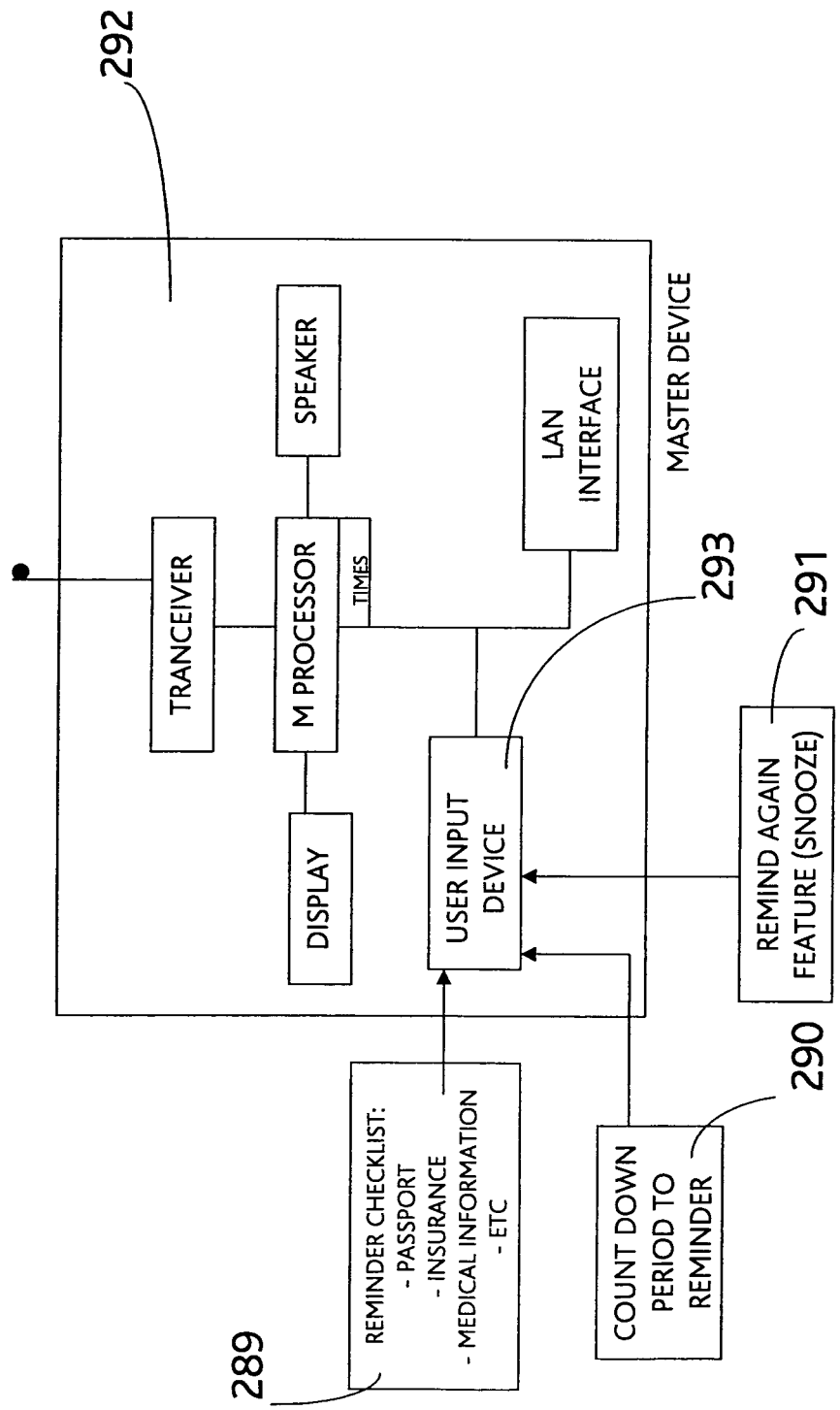
FIG. 29 shows a system block diagram representing the components of a device, which communicates to the device's user during the reminder process.

FIG. 29 shows some examples of typical data attributes, which the user enters into the master device 289 via a user input device 293. Dialogue box 289 details the data attributes for a short reminder checklist, which informs the user to remember selected items on their departure from a hotel. Dialogue box 290 details the data attributes for the time of period in which to activate the Pack-Me system prior to the user's departure time. Dialogue box 291 details the data attributes for the remind again feature, which is similar to a snooze feature on a typical alarm clock. This will reset the Pack-Me system to re-launch again after a predetermined time period 290 has lapsed.

Figure 30:
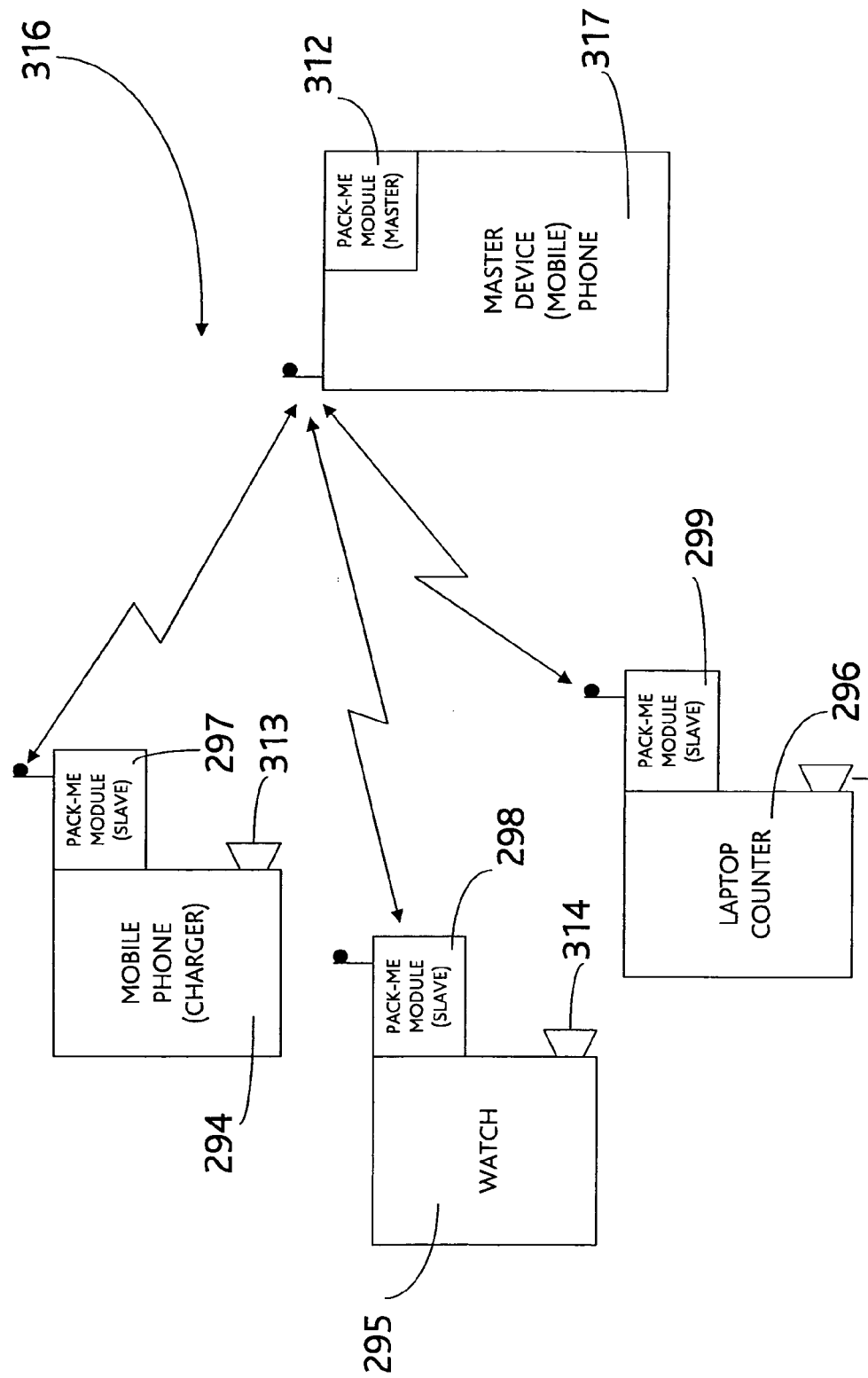
FIG. 30 shows a system block diagram representing the components of a device, which communicates with associated network elements.

FIG. 30 shows an alternative embodiment of the Pack-Me system 316 which incorporates a master device in form of a mobile phone 317. The mobile phone 317 is shown to be in communication with three associated slave devices, which are a mobile phone charger 294, a watch 295 and a laptop computer. All the slave devices 294-296 incorporate an audio alarm device 313-315 for communicating to the user when activated. The Mobile phone 317 is shown to incorporate a Pack-Me master module 312 and the stave devices 294 to 296 are shown to incorporate Pack-Me slave modules 297 to 299.

Figure 31:
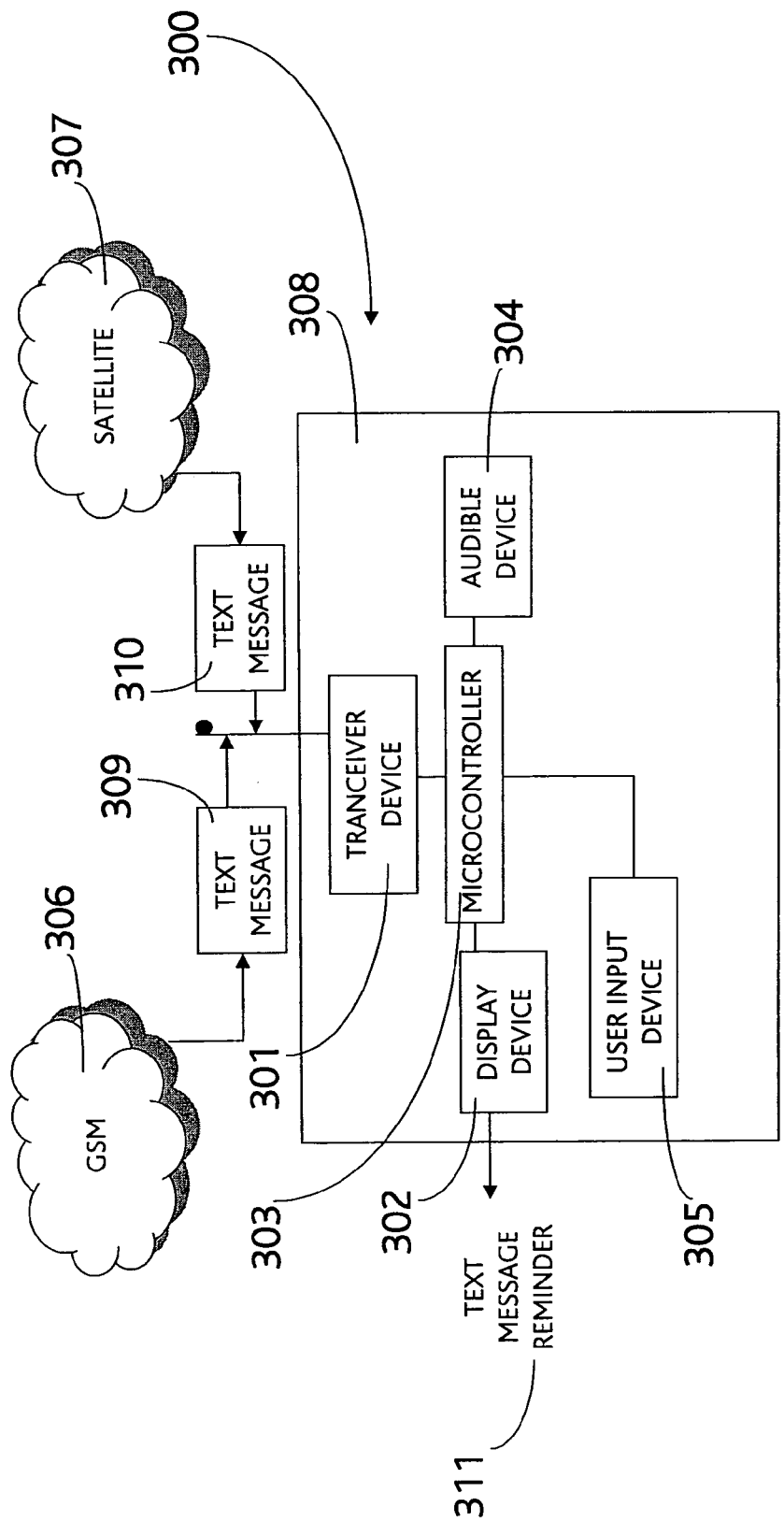
FIG. 31 shows a system block diagram representing the components of a device, which communicate with external communication systems.

FIG. 31 shows an alternative embodiment of the Pack-Me system 300, which includes a transceiver device 301, a display device 302, a microcontroller 303, an audible device 304 and a user input device 305. This embodiment of the Pack-Me system togs the reminder entered by the user on to an external network, such as a GSM mobile network 306 and/or a satellite network GPS 307. Once the reminder event has been logged on the relevant network, the network will communicate a message to the user via the master device 308. The message will be received by the transceiver device 301. The communication message may be in the form of a conventional SMS message, otherwise known as a text message 309 and 310, which is then received by the transceiver device 301. The message is then processed by the microcontroller device 303 and displayed to the user as a reminder message via the display device 302.

The following illustrates a travel packing assisting system also referred to as "Pack-Me":

Pack Me - sets reminder to pack unit and accessories (chargers, cables, powerpacks, antennas, cards, accessories, etc.) once function triggered, e.g. change in:
Being switched on
time zone (whether manually or through radio, satellite, PC synchronisation
roaming status
voltage change
format change e.g. PAL-NSTC)
if charger unplugged (e.g. on way to holiday, meeting etc.) (This feature could be switched off when in home territory, but useful for daily checkins into different hotels etc)
Monitoring key words, e.g. translations, depart, arrive, flight, train, taxi, etc.
Placed in a place without light (ie packed)
Under compression (in luggage)
Manual switch on/rapid set through hard or soft button as a convenient countdown timer
Pack-me could be user configured to provide additional checklists of items to remember e.g. passports, insurance, medical information,
Could provide a 'remind again' function similar to snooze on an alarm clock.
Could be loaded with a database of hotel chains and their check in/out times, contact numbers, airline confirmation numbers.

-continued

Note "pack me" could operate at network level, eg GSM, or satellite once roaming user detected in which case the network could send out a text or voice message with the appropriate reminder instead of it being generated in the unit.
Could incorporate battery, energy back up so the alarm works even if unit switched off.
Possibility of networking. A laptop, for example, can automatically set alarm on mobile or watch which you are more likely to have with you at all times. Likewise, all devices with Pack-me can receive alarm instructions from another device, eg P.C.
Possible uses:
Games consoles, esp hand helds
Toys
Watches/clocks
Music players
Binoculars, Cameras, Camcorders
2 way radios
Organisers
PDAs
DVD players (e.g. portable)
TVs (e.g. portable/hand held)
Laptop
Computer peripherals (mice) etc
MP4 players
Headsets
Road angels (detect speed cameras etc)
GPS systems
Bike computers
Golf computer
Fitness watches
Shavers
Electric games, puzzles etc
Electric instruments, key boards etc.

ZONEGARD & PACK-ME

| Item | Notes | Action Point |
|---|---|---|
| | Concept | |
| Integrated CO detector Achieved through embedding one or more sensors (e.g. a sensor array). The term 'sensor' in the following to be taken as singular or plural. | The concept could be extended to: any other airborne hazards; and to practically any kind of consumer electronics | |
| | Phased Development | |
| Phase 1 Embodiment | Travel clock Principal advantages: Virtually all components shared Points of sale for travel accessories &/or clocks vastly outnumber those for DIY product alone. More likely to be bought eg in airports, department stores, pharmacies, along with other travel items. Can be deployed next to user's bedside Larger screen can facilitate a more intelligent response than a plain 'ppm' read out, eg critical evacuation count down. | |
| Phase II | Module/PCMCIA/type version containing sensor, only for insertion into domestic consumer accessories such as TV. Principal advantages are: Most components shared Often more than 1 TV in a home Large display facilitates more information to convey to user Overall cost would represent mere 1-5% of unit cost. Module could be replaced or removed for testing without affecting rest of TV etc | |

-continued

ZONEGARD & PACK-ME

| Item | Notes | Action Point |
|---|---|---|
| Phase III embodiment | Possibility of Zonegard being charged up by host device to provide operating power during periods of absence. Miniaturisation of sensor only for incorporation into mobile phones. Principal advantage: most components shared 1 billion units sold annually usually more than 1 mobile per home usually kept next to sleeping people Would represent 5-10% of unit cost | |
| Future embodiments | Further possible permutations: Kitchen appliances Dictation machines* Diagnostic tools/pdas etc* Attack alarms Power tools* Baby monitors GPS units Automobile Info displays Aviation/nautical info displays | |

Overall Benefits

| | | |
|---|---|---|
| Intelligent | Intelligent monitoring, response, and alarm systems which can vary the units operating mode (eg depending in the user's health condition) or the unit's state (e.g. during sleep hours) | |
| Increase utilisation | Increase adoption of detection units to at least 1 per household, and in many cases more | |
| User interaction/awareness | Increase user interaction/familiarity with units. E.g. a clock, calendar, organiser is constantly referred to throughout the day and more accessible. | |
| Increase personal responsibility for CO hazards | Personal units lend greater confidence in unit's correct use, testing and care. Note, significant quantities of detectors have been recalled at various times which make it less safe to rely on units other than your own. Also, Note Dr Neil Hampson study of 79 victims of CO poisoning in Seattle of which 58 were from ethnic minorities so personal protection units are more likely to overcome language barriers. | |
| Testing | Facilitate easy and PROPER testing (current detectors only test circuitry and not the sensor itself). This is the main reason Phase II (incorporation in large items such as TVS is 'mudular') so that only the module needs to be removed and tested. | |

Functional Specification
Basic Functions

| | | |
|---|---|---|
| Basic CO hazard detector/Portable travel clock which . . . | 1. tells the time & date<br>2. has an alarm with snooze<br>3. has a calendar<br>4. has a reminder function<br>5. has illumination<br>(as close to an organiser interface as possible) | |
| Basic CO Hazard detection facility | 1. monitors ambient co levels<br>2. displays ambient co levels<br>3. logs ambient CO levels at appropriate intervals<br>4. Raises an alarm at the appropriate threshold eg:<br>After April 2006 the only valid standard across Europe will be EN50291.<br>E.g. Functionality could include allowing users to 'switch' between one international standard or another such as:<br>EN 50291 thresholds<br>UL 2034 thresholds | |

-continued

ZONEGARD & PACK-ME

| Item | Notes | Action Point |
|---|---|---|
| | Main alarm requirements (taken from EN 50291): at 30 ppm CO, the alarm must not activate for at least 120 minutes at 50 ppm CO, the alarm must not activate before 60 minutes but must activate before 90 minutes at 100 ppm CO, the alarm must not activate before 10 minutes but must activate before 40 minutes at 300 ppm CO, the alarm must activate within 3 minutes BS/EN 50291     Intelligent CO Functions | |
| Real time changing CO readout | Provides visual confirmation that the unit is functioning properly. Note, the test button on existing units only tests the circuitry NOT the sensor component itself. | |
| Intelligent monitoring and threat evaluation | Log the exact moment of the hazard being detected Log the measured changes over any given period Meter the overall exposure to CO (exposure level × duration) i.e. basic dosimeter function. compute and indicate the CRITICAL EXPOSURE/EVACUATION TIME before serious bodily harm occurs) (This information would be vital to rescue workers and military personnel working in known hazardous areas where NOT being able to operate there is not really viable, but at the same time, knowledge of the critical exposure levels would facilitate optimal management of the situation). Note also. This information presented as a countdown would also be useful for a pilot in gauging how to deal with detected presence of any toxic gas (Zonegard patent claims cover main toxic gasses and pollutants). This could be achieved by calculating or predicting carboxyhaemoglobin levels form any given environment for a particular user's characteristics and using mathematical prediction models including but not limited to the whole or modified versions of: Coburn RF, Forster RE, & Kane PB (1965) Considerations of the physiological variables that determine the blood carboxyhemoglobin concentration in man. J Clin Invest, 44: 1899-1910. (1965), and/or Stewart et al (Stewart RD, Peterson JE, Baretta ED, Bachand RT, Hosko MJ, & Herrmann AA (1910) Experimental human exposure to carbon monoxide. Arch Environ Health, 21: 154-164; Stewart, R. D., Peterson, J. E., Fisher, T. N., Hosko, M. J., Baretta, E. D., Dodd, H. C., Herrmann, A. A., Experimental human exposure to high concentrations of carbon monoxide, Arch. Environ. Health, 26, 1-7, 1973); and/or Singh et al, Selvakumar S, Sharan M, & Singh MP (1993) A mathematical model for the elimination of carbon monoxide in humans. J Theor Biol, 162: 321-336; Singh MP, Sharan M, & Selvakumar S (1991) A mathematical model for the computation of carboxyhemoglobin in human blood as a function of exposure time. Philos Trans R Soc Lond Biol Sci, B334: 135-147; and/or Selvakumar S, Sharan M, & Singh MP (1993) A mathematical model for the | |

ZONEGARD & PACK-ME

| Item | Notes | Action Point |
|------|-------|--------------|
| Ability to input sex, weight, age, general health, and whether user belongs to an especially vulnerable group. Or any of the other variables from the mathematical models listed in the previous section such as in Coburn Foster Kane. | elimination of carbon monoxide in humans. J Theor Biol, 162: 321-336. E.g. fetuses, infants, people who have anaemia, heart or lung diseases, or a high rate of metabolism (caused by certain conditions such as hyperthyroidism) may be susceptible to as little as 5 ppm as opposed to the usual 50 ppm at which most alarms would trigger. This data would also be essential to compute an appropriate CRITICAL EXPOSURE/EVACUATION TIME (see above) | |
| Intelligent threat representations | The user interface available should facilitate graphical or easily intelligible representations of the threat level. Note one of the side effects of CO poisoning is confusion so saying "200 ppm as current units do may not be very useful in a confused state. | |
| Auto protect at night time | Again, a feature only available by combining the detection unit with a time keeping device. E.g. Night time may trigger Extra sensitivity and/or a Different response profile (more rapidly ascending alarm volume, for example) Alternatively, a lesser state of readiness may be preferable to conserve battery life during less risk periods. E.g. daylight hours, or whilst packed in a suitcase, etc | |

Intelligent Alarm

| Item | Notes | Action Point |
|------|-------|--------------|
| Switchable full/ascending alarm | As both the fixed and mobile units are likely to be situated closer to users, an immediate alarm blast at 85 db may not be sensible or desired. An alarm response, in line with the CRITICAL EXPOSURE COUNTDOWN would be more sensible except during night time hours where the response could be accelerated. | |
| Vocal alarm and guidance for children aged 2+* | 10 loud beeps and "Wake up. Danger. Please leave the room and get help quickly". Designed to raise alarm outside and inside the room and to be intelliable to children as young as 2-3 years (with some training). Possibility of choosing their own alarm download from a website following online safety training presentation e.g. male female, fireman, policeman etc. Possibility of downloading health specific alarm to guide emergency workers. | |
| Integrated/optional vibration/strobe guard | For sight/hearing impaired. | |

Reminder Functions

| Item | Notes | Action Point |
|------|-------|--------------|
| Snooze | Appropriate snooze maximum permitted for co detection | |
| Incorporates Pack-Me ™ | See Pack-Me Functional Spec below. | |
| Annual Boiler/Appliance reminder function | User can input date of boiler or other appliance undergoing a service or test so that the unit can display the same when requested and set a reminder for 12 month's time. Annual reminder to include sample contact info for Appliance Servicing company | |
| Can record date of test and set a reminder for next one | User can input date that the unit itself was tested/calibrated so that the unit can display the same when requested and set a reminder for 12 month's time. | |

Physical Features

| Item | Notes | Action Point |
|------|-------|--------------|
| Remote/satellite sensor unit | Linked wirelessly. Esp useful for Phase II where the Display Device can act as a central console from which to manage/review all remote sensors. A TV in one room could therefore act as a central console/interface for a number of satellite sensors placed around the premises. | |

-continued

ZONEGARD & PACK-ME

| Item | Notes | Action Point |
|---|---|---|
| Telescopic sensor unit | Especially useful for portable device as would be placed on table with minimal air flow from below. E.g. Fold out/swivel sensor like mobile phones | |
| Wall mountable | A or W shaped recess in centre at the back of the travel clock enabling it to be wall mounted on a single picture hook for either enhanced detection, or on a more permanent basis. Phase I Travel Clock likely to be utilised by end users when they return home so should be designed so easily wall mountable as an attractive clock. | |
| | Networking Features | |
| Wireless networking with other similar or master units | Use of logged data for: Intelligent investigation of hazard source; Recommended evacuation route (without need of external computer. E.g. the units could compute which detected a hazard first, and then monitor spread patterns. | |
| Wireless alert | Possibility for the unit to send wireless alert/message to a remote monitoring unit or station or network (e.g. to a mobile network) to raise and alarm either automatically or if the user fails to provide a required response to an alert situation as expected. | |
| Other networking | USB, memory card, for access, transfer of logged data on a pc or central monitoring station. Useful to allow downloads of: Patches Software upgrades User selectable alarms including health related alarms. | |

PACK-ME

| Item | Notes | Action Point |
|---|---|---|
| | Concept | |
| Function | Pack-Me is a utility which sits within electronic devices and detects when they are likely to be in a state of travel i.e. away from home. Once it detects this, it asks the user to set a "Pack-Me" reminder which could be in the next few minutes or at hotel check out in 2 weeks time. | |
| Purpose | The utility is designed to keep consumers, their devices, and their associated accessories, cables, and chargers together. The utility could be incorporated into a whole host of consumer electronics eg: Mobile phones Travel clocks Gps units Pdas Medical equipment such as blood pressure/insulin monitoring kits | |
| | Overall Benefits | |
| Inconvenience & safety | Imagine forgetting your mobile, pda, or laptop charger either at home or whilst travelling. Or, a cable for your laptop and LCD projector which you needed for your presentation. Hotels have drawers full of chargers which people have left behind. And | |

-continued

PACK-ME

| Item | Notes | Action Point |
|---|---|---|
| | where people increasingly use their devices for their contacts and appointments, it could be hugely inconveniencing and embarrassing to find you cannot access that key presentation you have been working on, an essential phone number, log in details, traveller cheque numbers etc. | |
| Cost benefits | Chargers and peripherals are often very expensive. I had to replace a Dell battery charger once which I left on holiday and it cost £70. That's probably about a third of the value of the laptop itself at that time which was 4 years old. Similarly, I almost had to replace a charger for my Nikon camera. Once again, it was £45 and this time, over half of the value of my camera at that time. | |
| Environmental benefits | The environmental impact of having to manufacture, distribute, support, and ultimately dispose of hundreds of millions of unnecessary replacement and spare stock should not be ignored. For example, mobile phones alone account for 1 billion annual units of sale. If 10% of people have a "spare" charger, that's an extra 100 million chargers ultimately destined for disposal. Clearly, mobile phones represent only one segment of the overall consumer electronics environment. | |

-continued

PACK-ME

| Item | Notes | Action Point |
|---|---|---|
| *Functional Specification* | | |
| Device Condition | Being powered up Being powered down if charger unplugged Manual Switch on through hard or soft 'Rapid Set' button as a convenient countdown timer. | |
| Travel Detect | Change in the following: Current time zone (whether manually or through radio, satellite, PC synchronisation roaming status voltage change format change e.g. PAL-NSTC) Monitoring key words, e.g. "translation", "departure", "arrival", "flight", "train", "taxi", etc. Placed in a place without light (ie packed) Under compression (in luggage) | |
| User configurability | Pack-me could be user configured to provide additional checklists of items to remember eg passports, insurance, medical information, Could be loaded with a database of hotel chains and their check in/out times, contact numbers, airline confirmation numbers. | |
| Snooze Function | Could provide a 'Remind again' function similar to snooze on an alarm clock. | |
| Networking | Possibility of networking. So laptop for example, can automatically set alarm on: mobile or watch which you are more likely to have with you at all times or the associate charger or accessory itself equipped with a radio transceiver, power supply, controller and small beeper or visual aid such as an led in a manner akin to 'paging' the peripheral. Likewise, all devices with Pack-me can receive alarm instructions from another device, eg pc so all can beep at a certain time. Pack-Me could operate at network Level, eg gsm, or satellite once roaming user detected in which case the network could send out a text or voice message with the appropriate reminder instead of it being generated in the unit. | |
| Power back up | Could incorporate a rechargeable/battery or energy store so the alarm works even if unit switched off. | |
| Possible Uses | Games consoles, esp hand helds Toys Watches/clocks Music players Cameras, Camcorders 2 way radios Organisers Pdas Dvd players (eg portable) TVs (eg portable/hand held) Laptop Computer peripherals (mice) etc Mp4 players Headsets Road angels (detect speed cameras etc) GPS systems Bike computers Golf computer Fitness watches Shavers Electric games, puzzles etc Electric instruments, key boards etc. | |

Further Notes for Zonegard:
Ability for Zonegard to be designed as a module to fit inside and be ejected from host devices.
Feature that the module is charged up by host device, so that CO protection would be available even when host device would be switched off (TV during holidays). The specific implementation is not implicitly disclosed and must therefore be part of a "top-up" application in order to have a fall back position for this specific version.
A specific kitchen appliance incorporating Zonegard such as an oven and/or a dishwasher would also depart from the state of the art. Incorporating zonegard in aviation/nautical instrumentation; automobile instrumentation would also depart from the state of the art.
The ability of inputting data dependent upon a specific list of groups.
A device with extra sensitivity or a different response profile.

Further Notes for Pack-Me
The paging function marks a complete departure from the state of the art; it incorporates in a device such as a mobile phone a wireless transmitter; whilst a wireless receiver is incorporated into a peripheral device such as a remote control, headphones, microphone, or charger which when an appropriate signal is received causes an audio, and/or visual, and/or vibration-based alarm to be produced.
Non portable medical devices incorporating pack-me are also envisaged.

The invention claimed is:

1. A mobile electronic communication unit comprising a processor for operating said unit; said processor being configured to operate said unit in a first mode of operation during which a) monitoring of carbon monoxide levels occurs and a level of carbon monoxide is assessed against predetermined levels; and b) communication to and from the unit is activated provided an acceptable category of pre-determined levels is identified; wherein said communication unit incorporates an ambient carbon monoxide monitoring sensor integral with said unit: and said processor is configured to operate said unit in a second mode of operation during which a) monitoring of said carbon monoxide occurs and an alarming level of carbon monoxide is assessed against predetermined levels; and b) said processor interrupts the communication of said first mode of operation once a level of ambient carbon monoxide is assessed to warrant the user's attention; and c) an alarm routine is launched;
wherein during said first mode of operation, said processor evaluates the level of harm of exposure to a detected carbon monoxide level; and assesses the length of time for arriving at said alarming level at said detected exposure level; said unit further comprising a display for displaying a countdown of said length of time which said carbon monoxide level is tolerable prior to reaching said alarming level; said processor counting down said time until either potentially reaching said alarming level; at which point said alarm routine is launched during said second mode of operation; or an acceptable level of air quality is reached.

2. A unit according to claim 1, wherein the unit further comprises a communication interface for inputting signals representative one of characteristics selected from the group comprising: sex, weight, age, physical activity levels and health of an individual; and a plurality of predetermined operational modes corresponding to said characteristics; said length of time of tolerable exposure is determined in accordance with said user inputted characteristics together with said detected carbon monoxide level; whereby countdown is tailored to a particular user whilst exposed to a particular carbon monoxide level.

3. A unit according to claim 1, wherein said unit further comprises a mode of operation during which said processor obtains signals representative of said sensed carbon monoxide level at a plurality of points in time; a storage for storing a plurality of alarm signals; and a display for displaying an indication of level of carbon monoxide dependent upon the evolution through time of said signals representative of said sensed carbon monoxide level.

4. A unit according to claim 1, wherein said unit further comprises a communication interface for inputting signals for triggering a future mode of operation; and a trigger for triggering a mode of operation dependent upon the reaching of a predetermined time.

5. A unit according to claim 1, wherein said unit further comprises a recorder for recording signals representative of a change in operational mode during a period of time.

6. A unit according to claim 1, wherein said unit further comprises an indicator for indicating a carbon monoxide level, said processor being configured to obtain signals representative of said sensed carbon monoxide level at a plurality of points in time, and a display for displaying fluctuations in determined carbon monoxide levels.

7. A unit according to claim 1, wherein said unit further comprises a vibrator alarm for causing the unit to vibrate provided a harmful category of pre-determined levels is identified.

8. A unit according to claim 1, wherein said unit further comprises a light acting as a visual alarm provided a harmful category of pre-determined levels is identified.

9. A unit according to claim 1, wherein said unit incorporates a wireless transmitter for sending a signal representative of the unit's status to a wireless receiver.

10. A unit according to claim 1, wherein said unit further comprises a housing incorporating said processor and a sensor holder which allows the sensor to be held at a variable spaced apart distance from said housing.

11. A unit according to claim 1, wherein said unit further comprises a wireless communication interface in communication with one or more remotely located sensors.

12. A unit according to claim 1, wherein said unit incorporates at least one of the following further sensors: altitude, atmospheric, pressure, humidity, and/or temperature sensor; and said processor is configured to adjust the assessment of level of carbon monoxide in accordance with values derived from said sensor in addition to values derived from said carbon monoxide sensor.

13. A unit according to claim 1, wherein said unit incorporates a single microprocessor which incorporates said sensor.

14. A unit according to any of claim 1, wherein said unit incorporates a calendar function which stores a date and carbon monoxide level for subsequent retrieval and processing.

15. A unit according to claim 1, wherein said unit incorporates a first alarm routine suitable for triggering an alarm which is perceptible during an operator's sleep when in the vicinity of said unit and a second alarm routine suitable for triggering an alarm which is perceptible whilst the operator is active when in the vicinity of said unit.

16. A unit according to claim 1, wherein said unit further comprises an alarm for communicating a warning signal to a user which is specific to at least one articles to be packed; and a processor which during a period preceding a user's change of location triggers the communication of said signal to a user of said system in order to remind a user to pack an article.

17. A unit according to claim 8, wherein a sensor for detecting the location of the unit and a processor for controlling the timing of a warning signal generation dependent upon a location.

18. A unit according to claim 1, wherein said sensor is exposed to air.

19. A unit according to claim 1, wherein said unit incorporates means for inputting a user's activity level and for selecting a response level dependent upon both said detected carbon monoxide level and said selected activity level.

20. A unit according to claim 1, wherein said unit incorporates an alarm routine which varies in decibels dependent upon the activity of said user.

21. A unit according to claim 1, wherein the unit further comprises a communication interface for inputting signals representative of the health characteristics of an individual; and a plurality of predetermined operational modes corresponding to said health characteristics; said length of time of tolerable exposure is determined in accordance with said user inputted characteristics together with said detected carbon monoxide level; whereby countdown is tailored to a particular user whilst exposed to a particular carbon monoxide level.

22. A mobile electronic communication unit comprising a processor for operating said unit; said processor being configured to operate said unit in a first mode of operation during which a) monitoring of carbon monoxide levels occurs and a level of carbon monoxide is assessed against predetermined levels; and b) communication to and from the unit is activated provided an acceptable category of pre-determined levels is identified; wherein said communication unit incorporates an ambient carbon monoxide monitoring sensor integral with said unit: and said processor is configured to operate said unit in a second mode of operation during which a) monitoring of said carbon monoxide occurs and an alarming level of carbon monoxide is assessed against predetermined levels; and b) said processor launches an alarm routine;

wherein during said first mode of operation, said processor evaluates the level of harm of exposure to a detected carbon monoxide level; and assesses the length of time for arriving at said alarming level at said detected exposure level; said unit further comprising a display for displaying a countdown of said length of time which said carbon monoxide level is tolerable prior to reaching said alarming level; said processor counting down said time until either potentially reaching said alarming level, at which point said alarm routine is launched; or an acceptable level of air quality is reached.

23. A mobile electronic communication unit comprising a processor for operating said unit; said processor being configured to operate said unit in a first mode of operation during which a) monitoring of carbon monoxide levels occurs and a level of carbon monoxide is assessed against predetermined levels; and b) communication to and from the unit is activated provided an acceptable category of pre-determined levels is identified; wherein said communication unit incorporates an ambient carbon monoxide monitoring sensor integral with said unit: and said processor is configured to operate said unit in a second mode of operation during which a) monitoring of said carbon monoxide occurs and an alarming level of carbon monoxide is assessed against predetermined levels; and b) said processor launches an alarm routine;

wherein during said first mode of operation, said processor evaluates the level of harm of exposure to a detected carbon monoxide level; and assesses the length of time for arriving at said alarming level at said detected exposure level; and wherein the unit further comprises a communication interface for inputting signals representative of the health characteristics of an individual; and a plurality of pre-determined operational modes corresponding to said health characteristics; said length of time of tolerable exposure is determined in accordance with said user inputted characteristics together with said detected carbon monoxide level.

24. A mobile electronic communication unit comprising a processor for operating said unit; said processor being configured to operate said unit in a first mode of operation during which a) monitoring of carbon monoxide levels occurs and a level of carbon monoxide is assessed against predetermined levels; and b) communication to and from the unit is activated provided an acceptable category of pre-determined levels is identified; wherein said communication unit incorporates an ambient carbon monoxide monitoring sensor integral with said unit: and said processor is configured to operate said unit in a second mode of operation during which a) monitoring of said carbon monoxide occurs and an alarming level of carbon monoxide is assessed against predetermined levels; and b) said processor launches an alarm routine;

wherein during said first mode of operation, said processor evaluates the level of harm of exposure to a detected carbon monoxide level; and assesses the length of time for arriving at said alarming level at said detected exposure level; and wherein said unit incorporates an alarm routine which varies in decibels dependent upon the activity of said user.

* * * * *